(12) United States Patent
De Maria

(10) Patent No.: US 8,865,637 B2
(45) Date of Patent: Oct. 21, 2014

(54) VARIANTS OF A LYSOZYME AND POLYNUCLEOTIDES ENCODING SAME

(75) Inventor: Leonardo De Maria, Frederiksberg (DK)

(73) Assignee: Novozymes Als, Bagsvaerd (DK)

( * ) Notice: Subject to any disclaimer, the term of this patent is extended or adjusted under 35 U.S.C. 154(b) by 50 days.

(21) Appl. No.: 13/521,538

(22) PCT Filed: Feb. 25, 2011

(86) PCT No.: PCT/EP2011/052812
§ 371 (c)(1),
(2), (4) Date: Jul. 11, 2012

(87) PCT Pub. No.: WO2011/104339
PCT Pub. Date: Sep. 1, 2011

(65) Prior Publication Data
US 2012/0288490 A1 Nov. 15, 2012

Related U.S. Application Data

(60) Provisional application No. 61/309,065, filed on Mar. 1, 2010.

(30) Foreign Application Priority Data

Feb. 25, 2010 (EP) .................... 10154756

(51) Int. Cl.
| | | |
|---|---|---|
| C11D 3/395 | (2006.01) | |
| C12N 9/36 | (2006.01) | |
| C12N 1/20 | (2006.01) | |
| C12N 15/00 | (2006.01) | |
| C07H 21/04 | (2006.01) | |
| A61Q 11/00 | (2006.01) | |
| A61Q 19/00 | (2006.01) | |
| A23C 19/11 | (2006.01) | |
| C11D 3/386 | (2006.01) | |
| A61Q 1/06 | (2006.01) | |
| A61K 8/66 | (2006.01) | |
| A23K 1/165 | (2006.01) | |
| A23L 3/3571 | (2006.01) | |
| A61Q 1/04 | (2006.01) | |
| A61Q 17/00 | (2006.01) | |

(52) U.S. Cl.
CPC ............ *C11D 3/38636* (2013.01); *A61Q 11/00* (2013.01); *A61Q 19/00* (2013.01); *C12N 9/2462* (2013.01); *A23C 19/11* (2013.01); *A61Q 1/06* (2013.01); *A61K 8/66* (2013.01); *A23K 1/1653* (2013.01); *C12Y 32/01017* (2013.01); *A23L 3/3571* (2013.01); *A61Q 1/04* (2013.01); *A61Q 17/005* (2013.01)
USPC ..... 510/226; 435/206; 435/252.3; 435/320.1; 536/23.2

(58) Field of Classification Search
CPC ...................................................... C12N 9/2465
USPC ............ 435/183, 200, 252.3, 320.1; 536/23.2
See application file for complete search history.

(56) References Cited

U.S. PATENT DOCUMENTS

| | | |
|---|---|---|
| 4,355,022 A | 10/1982 | Rabussay |
| 5,041,236 A | 8/1991 | Carpenter et al. |

FOREIGN PATENT DOCUMENTS

| | | |
|---|---|---|
| EP | 0 425 016 B1 | 5/1991 |
| WO | 00/21381 A1 | 4/2000 |
| WO | 20041017988 A1 | 3/2004 |
| WO | 20041026334 A1 | 4/2004 |
| WO | 20051080559 A1 | 9/2005 |
| WO | 20081124764 A1 | 10/2008 |

OTHER PUBLICATIONS

Sequence alignment between Accession No: A1C415 & Applicants' Seq ID No. 3, 2007 (embedded in the Office Action).*
Written Opinion, ISA—(2011).*
Fedorovo et al., UniProt Accession No. A1DBU6 (2007).
Fedorovo et al., UniProt Accession No. A1C415 (2007).
Fedorovo et al., UniProt Accession No. BOY9F1 (2008).
Hughey et al., Applied and Environmental Microbiology, vol. 53, No. 9, pp. 2165-2170 (1987).
Korczynska et al., Acta Crystallographica Section F, Structural Biology and Crystallization Communications, vol. 66, No. 9, pp. 973-977 (2010).
Martinez-Fleites et al., Carbohydrate Research, vol. 344, No. 13, pp. 1753-1757 (2009).

* cited by examiner

*Primary Examiner* — Tekchand Saidha
(74) *Attorney, Agent, or Firm* — Elias Lambiris

(57) ABSTRACT

The present invention relates to variant lysozymes. The present invention also relates to polynucleotides encoding the variant lysozymes and to nucleic acid constructs, vectors, and host cells comprising the polynucleotide.

28 Claims, 26 Drawing Sheets

```
                    10         20         30         40         50
               1234567890 1234567890 1234567890 1234567890 1234567890
SEQID3         LPSQPEARAT TVQGFDISNH QKSVNFEAAK KDGAQFVMIK ATEGTTYKDT
SEQID4         LPSQPEARAT TVQGFDISNH QKSVNFEAAK KDGAQFVMIK ATEGTTYKDT
SEQID5         LPSQPEARAT TIQGFDISNH QKSVNFEAAK KDGAQFVMIK TTEGTTYKDT
SEQID6         LPSQSEAHAS TVQGFDISNH QKTVDFEAAK KDGAQFVMIK ATEGTTYKDT
SEQID7         .......... ....FDISNH QATVDFKAAY NDGARFVMIK ATEGTTFTDK
SEQID8         .........D TVQGFDISNH QGSVDFAAAY NAGARFVMIK SSEGTSYSDP
SEQID9         .......... TVQGFDISHY QANVNFAAAY NSGARFVMIK ATESTTYTDP
SEQID10        .......... AVQGFDISHY QSNVNFAAAY NSGARFVMIK ATESTTYTDP
SEQID11        .......... AVQGFDISNY QSSVNFASAY SSGARFVMIK ATEGTTYTDP
SEQID12        .......... AVQGFDISHY QSSVNYAGAY NSGARFVMIK ATEGTTYTDP
SEQID13        .......... TVQGFDISSY QPNVNFNAAY SAGARFVIIK ATEGTTYIDS 60         70         80         90        100
               1234567890 1234567890 1234567890 1234567890 1234567890
SEQID3         VFNSHYTGAT KAGLLRGGYH FARPDKSTGS TQAKFFLKNG GGWSDDNRTL
SEQID4         VFNSHYTGAT KAGLLRGGYH FARPDKSTGS TQAKFFLKNG GGWSDDNRTL
SEQID5         VFNSHYTGAT KAGLLRGGYH FARPDKSTGS TQAKFFLKNG GGWSNDNRTL
SEQID6         TFNSHYTGAT KAGLIRGGYH FARPDKSSGS TQATYFVKNG GGWSDDKMTL
SEQID7         VFSSHYQGAT DAGLIRGGYH FALPDSSSGA EQAEFFLKNG GGWSKDGITL
SEQID8         SFSSHYTGAT DAGFIRGGYH FALPDASSAA DQVSYFISHG GGWSKDGITL
SEQID9         AFSSHYTGAT NAGFIRGGYH FAIPNDSSGA AQAKYFLAHG GGWSNDGITL
SEQID10        SFSSHYTGAT NAGFIRGGYH FAIPNASSGA AQAKYFLAHG GGWSNDGITL
SEQID11        TFSSHYIGAT NAGLIRGGYH FAIPSSSGA TQAKYFISHG GGWSADGITL
SEQID12        SFSTHYTGAT NAGLIRGGYH FARPDTSSGA VQANYFLKHG GGWTSDGITL
SEQID13        TFSNHYIGAT NAGFIRGGYH FAHPSVSSGA TQAKYFIAHG GGWSGDGITL 110        120        130        140        150
               1234567890 1234567890 1234567890 1234567890 1234567890
SEQID3         PGMLDIEYNP YGATCYGLSH SQMVAWIHDF VNEYHHATSR WPMIYTTADW
SEQID4         PGMLDIEYNP YGATCYGLSH SQMVAWIHDF VNEYHHATSR WPMIYTTADW
SEQID5         PGMLDIEYNP YGATCYGLSH SQMVAWIHDF VDEYHHATSR WPMIYTTADW
SEQID6         PGMLDIEYNP YGATCYGLSH SAMVSWIKEF VDEYHSATKR YPMIYTTADW
SEQID7         PGMLDIEYNP YGATCYDKSA EDMVAWIKDF VDTYQKATGV YPLIYSTADW
SEQID8         PGMLDIEYNP YGDTCYGLSA SDMVAWIQEF VDEYHSATGV YPMLYTTADW
SEQID9         PGMLDIEYNP YGATCYGLSA SQMVSWISDF VNTYKSSTGR YPMIYTTADW
SEQID10        PGMLDIEYNP YGATCYGLSA SQMVSWISDF VNTYKSSTGR YPMIYTTADW
SEQID11        PGMLDIEYNP YGATCYGLSA SQMVAWIKDF ANTYKASVGR YPMIYTTNDW
SEQID12        PGMLDIEYNP YGATCYGLSA SSMVSWISDF VETYKSAVGR YPMIYTTANW
SEQID13        PGMLDIEYNP NGATCYGLSA SQMVSWIHDF VNTYYASEGV YPMIYTTNDW 160        170        180        190        200
               1234567890 1234567890 1234567890 1234567890 1234567890
SEQID3         WNRCTGNAKG FGDKCPLVLA AYSSSPPKTI PGDWKTWTIW QNSDKYKHGG
SEQID4         WNRCTGNAKG FGDKCPLVLA AYSSSPPKTI PGDWKKWTIW QNSDKYKHGG
SEQID5         WNRCTGNAKG FGDKCPLVLA AYSSSPPKTI PGDWKTWTIW QNSDKYEHGG
SEQID6         WNRCTGNAKG FGDKCPLVLA AYSSTAPKTI PGDWKTWTIW QDSDKYKHGG
SEQID7         WKTCTGNAGG FGSTCPLVLA AYSDSAPSTI PGDWATYTIW QNSDSYKHGG
SEQID8         WSTCTGNASG FGDKCPLVLA AYSSSAPSTI PGDWATYTMW QNSDSYEYGG
SEQID9         WNTCTGNSKS FT.ECPLVLA RYSSS.VGTI PGGWPYQSFW QNSDSYTYGG
SEQID10        WNTCTGNSKS FT.DCPLVLA RYSSS.VGTI PGGWPYQSFW QNSDSYTYGG
SEQID11        WNTCTGNSQA FT.DCPLVLA RYSSS.AGTI PGGWPYQSFW QNSDSYTYGG
SEQID12        WSTCTGNSAA FT.DCPLVLA RYSSS.VGTI PGGWPYQSIW QNSDSYAYGG
SEQID13        WTTCTGDSTA FSTTCPLVLA RYASS.PGTI PGGWGYQTIW QNTDSYAYGG
```

Fig. 1

```
                              210        220
                       1234567890 1234567890
           SEQID3      DSDKFNGPMT QLRKLASG..
           SEQID4      DSDKFNGPMT QLRKMPSK..
           SEQID5      DSDKFNGPMT QLRKLASG..
           SEQID6      DSDKFNGPMT QLKKLASG..
           SEQID7      DSDIFNGGYE QLQKIAKAE.
           SEQID8      DSDIFNGPFE SLQKIANAA.
           SEQID9      DSDIWNGSLN NLKTFAKG..
           SEQID10     DSEIWNGSLD NLKKFAKG..
           SEQID11     DSDIWNGSLD NLKKFAATAA
           SEQID12     DSDIWNGDEA GLSRFAKG..
           SEQID13     DSDVFNGALS QLKAIALG..
```

Fig. 1 cont.

```
ATOM    1   N    ALA    9    -34.323   -8.869  42.352  1.00 00.00
ATOM    2   CA   ALA    9    -32.947   -9.451  42.367  1.00 00.00
ATOM    3   C    ALA    9    -32.663  -10.013  43.755  1.00 00.00
ATOM    4   O    ALA    9    -33.371   -9.675  44.741  1.00 00.00
ATOM    5   CB   ALA    9    -31.907   -8.395  41.991  1.00 00.00
ATOM    6   N    THR   10    -31.649  -10.881  43.840  1.00 00.00
ATOM    7   CA   THR   10    -31.304  -11.516  45.135  1.00 00.00
ATOM    8   C    THR   10    -29.814  -11.418  45.473  1.00 00.00
ATOM    9   O    THR   10    -29.017  -11.005  44.641  1.00 00.00
ATOM   10   CB   THR   10    -31.749  -13.006  45.226  1.00 00.00
ATOM   11   CG2  THR   10    -33.229  -13.190  44.814  1.00 00.00
ATOM   12   OG1  THR   10    -30.890  -13.819  44.411  1.00 00.00
ATOM   13   N    THR   11    -29.465  -11.795  46.702  1.00 00.00
ATOM   14   CA   THR   11    -28.073  -11.822  47.162  1.00 00.00
ATOM   15   C    THR   11    -27.671  -13.184  47.802  1.00 00.00
ATOM   16   O    THR   11    -28.518  -13.987  48.179  1.00 00.00
ATOM   17   CB   THR   11    -27.796  -10.683  48.157  1.00 00.00
ATOM   18   CG2  THR   11    -28.084   -9.337  47.524  1.00 00.00
ATOM   19   OG1  THR   11    -28.640  -10.833  49.309  1.00 00.00
ATOM   20   N    VAL   12    -26.376  -13.448  47.840  1.00 00.00
ATOM   21   CA   VAL   12    -25.822  -14.632  48.447  1.00 00.00
ATOM   22   C    VAL   12    -24.923  -14.140  49.582  1.00 00.00
ATOM   23   O    VAL   12    -24.016  -13.276  49.382  1.00 00.00
ATOM   24   CB   VAL   12    -25.000  -15.476  47.421  1.00 00.00
ATOM   25   CG1  VAL   12    -24.302  -16.639  48.097  1.00 00.00
ATOM   26   CG2  VAL   12    -25.922  -16.010  46.291  1.00 00.00
ATOM   27   N    GLN   13    -25.194  -14.646  50.778  1.00 00.00
ATOM   28   CA   GLN   13    -24.386  -14.262  51.901  1.00 00.00
ATOM   29   C    GLN   13    -22.976  -14.771  51.754  1.00 00.00
ATOM   30   O    GLN   13    -22.739  -15.908  51.314  1.00 00.00
ATOM   31   CB   GLN   13    -24.971  -14.784  53.196  1.00 00.00
ATOM   32   CG   GLN   13    -24.067  -14.427  54.383  1.00 00.00
ATOM   33   CD   GLN   13    -24.286  -13.009  54.861  1.00 00.00
ATOM   34   NE2  GLN   13    -23.212  -12.353  55.291  1.00 00.00
ATOM   35   OE1  GLN   13    -25.406  -12.507  54.861  1.00 00.00
ATOM   36   N    GLY   14    -22.030  -13.929  52.170  1.00 00.00
ATOM   37   CA   GLY   14    -20.635  -14.336  52.400  1.00 00.00
ATOM   38   C    GLY   14    -20.015  -13.558  53.582  1.00 00.00
ATOM   39   O    GLY   14    -20.739  -12.875  54.339  1.00 00.00
ATOM   40   N    PHE   15    -18.720  -13.753  53.768  1.00 00.00
ATOM   41   CA   PHE   15    -17.894  -13.067  54.767  1.00 00.00
ATOM   42   C    PHE   15    -16.405  -12.994  54.358  1.00 00.00
ATOM   43   O    PHE   15    -16.009  -13.520  53.325  1.00 00.00
ATOM   44   CB   PHE   15    -18.183  -13.607  56.203  1.00 00.00
ATOM   45   CG   PHE   15    -17.726  -15.048  56.470  1.00 00.00
ATOM   46   CD1  PHE   15    -17.013  -15.337  57.615  1.00 00.00
ATOM   47   CD2  PHE   15    -18.100  -16.102  55.651  1.00 00.00
ATOM   48   CE1  PHE   15    -16.590  -16.658  57.914  1.00 00.00
ATOM   49   CE2  PHE   15    -17.683  -17.416  55.936  1.00 00.00
ATOM   50   CZ   PHE   15    -16.939  -17.694  57.057  1.00 00.00
ATOM   51   N    ASP   16    -15.587  -12.250  55.107  1.00 00.00
ATOM   52   CA   ASP   16    -14.173  -12.234  54.865  1.00 00.00
ATOM   53   C    ASP   16    -13.454  -12.169  56.188  1.00 00.00
ATOM   54   O    ASP   16    -13.962  -11.552  57.131  1.00 00.00
ATOM   55   CB   ASP   16    -13.718  -11.051  53.964  1.00 00.00
ATOM   56   CG   ASP   16    -14.031   -9.695  54.556  1.00 00.00
ATOM   57   OD1  ASP   16    -13.200   -9.184  55.330  1.00 00.00
ATOM   58   OD2  ASP   16    -15.119   -9.141  54.268  1.00 00.00
ATOM   59   N    ILE   17    -12.267  -12.770  56.224  1.00 00.00
ATOM   60   CA   ILE   17    -11.531  -12.998  57.458  1.00 00.00
ATOM   61   C    ILE   17    -10.035  -12.803  57.266  1.00 00.00
ATOM   62   O    ILE   17     -9.549  -12.667  56.144  1.00 00.00
ATOM   63   CB   ILE   17    -11.817  -14.412  58.069  1.00 00.00
ATOM   64   CG1  ILE   17    -11.429  -15.538  57.085  1.00 00.00
ATOM   65   CG2  ILE   17    -13.261  -14.494  58.529  1.00 00.00
ATOM   66   CD1  ILE   17    -11.835  -16.991  57.564  1.00 00.00
ATOM   67   N    SER   18     -9.299  -12.835  58.366  1.00 00.00
ATOM   68   CA   SER   18     -7.857  -12.607  58.383  1.00 00.00
ATOM   69   C    SER   18     -7.324  -13.172  59.721  1.00 00.00
ATOM   70   O    SER   18     -8.084  -13.789  60.475  1.00 00.00
ATOM   71   CB   SER   18     -7.555  -11.100  58.284  1.00 00.00
```

Fig. 2

```
ATOM    72  OG  SER    18      -7.866 -10.408  59.487  1.00 00.00
ATOM    73  N   ASN    19      -6.064 -12.915  60.029  1.00 00.00
ATOM    74  CA  ASN    19      -5.508 -13.284  61.313  1.00 00.00
ATOM    75  C   ASN    19      -6.120 -12.604  62.525  1.00 00.00
ATOM    76  O   ASN    19      -5.794 -12.967  63.641  1.00 00.00
ATOM    77  CB  ASN    19      -3.981 -13.152  61.343  1.00 00.00
ATOM    78  CG  ASN    19      -3.527 -11.708  61.219  1.00 00.00
ATOM    79  ND2 ASN    19      -2.224 -11.502  61.232  1.00 00.00
ATOM    80  OD1 ASN    19      -4.355 -10.791  61.094  1.00 00.00
ATOM    81  N   HIS    20      -6.985 -11.615  62.318  1.00 00.00
ATOM    82  CA  HIS    20      -7.746 -11.069  63.433  1.00 00.00
ATOM    83  C   HIS    20      -8.656 -12.131  64.035  1.00 00.00
ATOM    84  O   HIS    20      -9.038 -12.037  65.200  1.00 00.00
ATOM    85  CB  HIS    20      -8.530  -9.879  62.995  1.00 00.00
ATOM    86  CG  HIS    20      -7.656  -8.693  62.674  1.00 00.00
ATOM    87  CD2 HIS    20      -8.092  -7.394  62.761  1.00 00.00
ATOM    88  ND1 HIS    20      -6.363  -8.626  62.272  1.00 00.00
ATOM    89  CE1 HIS    20      -6.045  -7.299  62.129  1.00 00.00
ATOM    90  NE2 HIS    20      -7.114  -6.575  62.407  1.00 00.00
ATOM    91  N   GLN    21      -8.995 -13.126  63.222  1.00 00.00
ATOM    92  CA  GLN    21      -9.744 -14.296  63.663  1.00 00.00
ATOM    93  C   GLN    21      -8.758 -15.451  63.794  1.00 00.00
ATOM    94  O   GLN    21      -8.319 -15.984  62.795  1.00 00.00
ATOM    95  CB  GLN    21     -10.836 -14.645  62.628  1.00 00.00
ATOM    96  CG  GLN    21     -12.011 -13.725  62.634  1.00 00.00
ATOM    97  CD  GLN    21     -11.673 -12.348  62.044  1.00 00.00
ATOM    98  NE2 GLN    21     -11.099 -12.356  60.855  1.00 00.00
ATOM    99  OE1 GLN    21     -11.937 -11.288  62.659  1.00 00.00
ATOM   100  N   LYS    22      -8.408 -15.860  65.019  1.00 00.00
ATOM   101  CA  LYS    22      -7.451 -16.976  65.152  1.00 00.00
ATOM   102  C   LYS    22      -8.096 -18.299  64.804  1.00 00.00
ATOM   103  O   LYS    22      -7.416 -19.231  64.393  1.00 00.00
ATOM   104  CB  LYS    22      -6.807 -17.067  66.552  1.00 00.00
ATOM   105  CG  LYS    22      -5.531 -16.256  66.658  1.00 00.00
ATOM   106  CD  LYS    22      -5.004 -16.178  68.096  1.00 00.00
ATOM   107  CE  LYS    22      -6.075 -15.756  69.047  1.00 00.00
ATOM   108  NZ  LYS    22      -5.508 -15.285  70.317  1.00 00.00
ATOM   109  N   SER    23      -9.412 -18.371  64.974  1.00 00.00
ATOM   110  CA  SER    23     -10.170 -19.557  64.575  1.00 00.00
ATOM   111  C   SER    23     -11.532 -19.097  64.104  1.00 00.00
ATOM   112  O   SER    23     -11.955 -17.987  64.426  1.00 00.00
ATOM   113  CB  SER    23     -10.300 -20.555  65.733  1.00 00.00
ATOM   114  OG  SER    23     -11.179 -21.635  65.397  1.00 00.00
ATOM   115  N   VAL    24     -12.190 -19.909  63.286  1.00 00.00
ATOM   116  CA  VAL    24     -13.490 -19.538  62.710  1.00 00.00
ATOM   117  C   VAL    24     -14.479 -20.717  62.690  1.00 00.00
ATOM   118  O   VAL    24     -14.130 -21.797  62.215  1.00 00.00
ATOM   119  CB  VAL    24     -13.337 -19.000  61.244  1.00 00.00
ATOM   120  CG1 VAL    24     -14.730 -18.723  60.642  1.00 00.00
ATOM   121  CG2 VAL    24     -12.533 -17.713  61.266  1.00 00.00
ATOM   122  N   ASN    25     -15.722 -20.461  63.142  1.00 00.00
ATOM   123  CA  ASN    25     -16.829 -21.474  63.109  1.00 00.00
ATOM   124  C   ASN    25     -17.376 -21.560  61.670  1.00 00.00
ATOM   125  O   ASN    25     -18.474 -21.024  61.353  1.00 00.00
ATOM   126  CB  ASN    25     -17.934 -21.062  64.115  1.00 00.00
ATOM   127  CG  ASN    25     -18.753 -22.262  64.653  1.00 00.00
ATOM   128  ND2 ASN    25     -19.331 -22.103  65.859  1.00 00.00
ATOM   129  OD1 ASN    25     -18.873 -23.291  63.994  1.00 00.00
ATOM   130  N   PHE    26     -16.620 -22.216  60.791  1.00 00.00
ATOM   131  CA  PHE    26     -17.004 -22.261  59.404  1.00 00.00
ATOM   132  C   PHE    26     -18.373 -22.946  59.250  1.00 00.00
ATOM   133  O   PHE    26     -19.200 -22.567  58.411  1.00 00.00
ATOM   134  CB  PHE    26     -15.907 -22.908  58.531  1.00 00.00
ATOM   135  CG  PHE    26     -14.710 -21.991  58.249  1.00 00.00
ATOM   136  CD1 PHE    26     -14.804 -20.941  57.305  1.00 00.00
ATOM   137  CD2 PHE    26     -13.496 -22.173  58.922  1.00 00.00
ATOM   138  CE1 PHE    26     -13.704 -20.116  57.021  1.00 00.00
ATOM   139  CE2 PHE    26     -12.383 -21.334  58.663  1.00 00.00
ATOM   140  CZ  PHE    26     -12.494 -20.305  57.679  1.00 00.00
ATOM   141  N   GLU    27     -18.625 -23.919  60.117  1.00 00.00
ATOM   142  CA  GLU    27     -19.846 -24.708  60.031  1.00 00.00
```

Fig. 2 cont.

```
ATOM    143  C    GLU  27    -21.073 -23.875  60.408  1.00 00.00
ATOM    144  O    GLU  27    -22.073 -23.861  59.670  1.00 00.00
ATOM    145  CB   GLU  27    -19.706 -25.960  60.923  1.00 00.00
ATOM    146  CG   GLU  27    -18.398 -26.771  60.666  1.00 00.00
ATOM    147  CD   GLU  27    -18.217 -27.284  59.187  1.00 00.00
ATOM    148  OE1  GLU  27    -17.058 -27.315  58.694  1.00 00.00
ATOM    149  OE2  GLU  27    -19.208 -27.715  58.544  1.00 00.00
ATOM    150  N    ALA  28    -20.995 -23.168  61.529  1.00 00.00
ATOM    151  CA   ALA  28    -22.044 -22.230  61.919  1.00 00.00
ATOM    152  C    ALA  28    -22.400 -21.245  60.799  1.00 00.00
ATOM    153  O    ALA  28    -23.548 -20.759  60.722  1.00 00.00
ATOM    154  CB   ALA  28    -21.600 -21.463  63.135  1.00 00.00
ATOM    155  N    ALA  29    -21.393 -20.900  59.988  1.00 00.00
ATOM    156  CA   ALA  29    -21.523 -19.857  58.951  1.00 00.00
ATOM    157  C    ALA  29    -22.325 -20.412  57.778  1.00 00.00
ATOM    158  O    ALA  29    -23.336 -19.835  57.383  1.00 00.00
ATOM    159  CB   ALA  29    -20.147 -19.415  58.483  1.00 00.00
ATOM    160  N    LYS  30    -21.873 -21.553  57.254  1.00 00.00
ATOM    161  CA   LYS  30    -22.615 -22.316  56.258  1.00 00.00
ATOM    162  C    LYS  30    -24.102 -22.492  56.626  1.00 00.00
ATOM    163  O    LYS  30    -25.005 -22.201  55.834  1.00 00.00
ATOM    164  CB   LYS  30    -21.954 -23.671  56.104  1.00 00.00
ATOM    165  CG   LYS  30    -22.226 -24.337  54.806  1.00 00.00
ATOM    166  CD   LYS  30    -21.359 -23.781  53.711  1.00 00.00
ATOM    167  CE   LYS  30    -21.356 -24.657  52.450  1.00 00.00
ATOM    168  NZ   LYS  30    -22.632 -24.536  51.738  1.00 00.00
ATOM    169  N    LYS  31    -24.329 -22.904  57.858  1.00 00.00
ATOM    170  CA   LYS  31    -25.649 -23.245  58.366  1.00 00.00
ATOM    171  C    LYS  31    -26.513 -22.004  58.457  1.00 00.00
ATOM    172  O    LYS  31    -27.739 -22.087  58.329  1.00 00.00
ATOM    173  CB   LYS  31    -25.503 -23.895  59.751  1.00 00.00
ATOM    174  CG   LYS  31    -25.269 -25.379  59.721  1.00 00.00
ATOM    175  CD   LYS  31    -25.223 -25.914  61.129  1.00 00.00
ATOM    176  CE   LYS  31    -24.626 -27.289  61.132  1.00 00.00
ATOM    177  NZ   LYS  31    -23.196 -27.233  60.718  1.00 00.00
ATOM    178  N    ASP  32    -25.876 -20.849  58.657  1.00 00.00
ATOM    179  CA   ASP  32    -26.596 -19.587  58.673  1.00 00.00
ATOM    180  C    ASP  32    -26.663 -19.001  57.243  1.00 00.00
ATOM    181  O    ASP  32    -27.105 -17.869  57.036  1.00 00.00
ATOM    182  CB   ASP  32    -25.966 -18.610  59.659  1.00 00.00
ATOM    183  CG   ASP  32    -26.964 -18.096  60.714  1.00 00.00
ATOM    184  OD1  ASP  32    -28.133 -18.564  60.724  1.00 00.00
ATOM    185  OD2  ASP  32    -26.583 -17.224  61.540  1.00 00.00
ATOM    186  N    GLY  33    -26.253 -19.788  56.257  1.00 00.00
ATOM    187  CA   GLY  33    -26.513 -19.420  54.860  1.00 00.00
ATOM    188  C    GLY  33    -25.306 -18.827  54.120  1.00 00.00
ATOM    189  O    GLY  33    -25.423 -18.469  52.939  1.00 00.00
ATOM    190  N    ALA  34    -24.152 -18.724  54.798  1.00 00.00
ATOM    191  CA   ALA  34    -22.924 -18.278  54.131  1.00 00.00
ATOM    192  C    ALA  34    -22.506 -19.248  53.021  1.00 00.00
ATOM    193  O    ALA  34    -22.647 -20.473  53.167  1.00 00.00
ATOM    194  CB   ALA  34    -21.778 -18.106  55.138  1.00 00.00
ATOM    195  N    GLN  35    -21.994 -18.705  51.910  1.00 00.00
ATOM    196  CA   GLN  35    -21.599 -19.531  50.752  1.00 00.00
ATOM    197  C    GLN  35    -20.186 -19.286  50.249  1.00 00.00
ATOM    198  O    GLN  35    -19.638 -20.077  49.454  1.00 00.00
ATOM    199  CB   GLN  35    -22.578 -19.357  49.566  1.00 00.00
ATOM    200  CG   GLN  35    -24.035 -19.725  49.864  1.00 00.00
ATOM    201  CD   GLN  35    -24.323 -21.231  49.737  1.00 00.00
ATOM    202  NE2  GLN  35    -25.620 -21.583  49.756  1.00 00.00
ATOM    203  OE1  GLN  35    -23.400 -22.066  49.604  1.00 00.00
ATOM    204  N    PHE  36    -19.617 -18.144  50.617  1.00 00.00
ATOM    205  CA   PHE  36    -18.256 -17.829  50.204  1.00 00.00
ATOM    206  C    PHE  36    -17.559 -17.026  51.315  1.00 00.00
ATOM    207  O    PHE  36    -18.194 -16.441  52.164  1.00 00.00
ATOM    208  CB   PHE  36    -18.221 -17.021  48.873  1.00 00.00
ATOM    209  CG   PHE  36    -18.834 -15.648  48.985  1.00 00.00
ATOM    210  CD1  PHE  36    -18.039 -14.531  49.188  1.00 00.00
ATOM    211  CD2  PHE  36    -20.214 -15.482  48.924  1.00 00.00
ATOM    212  CE1  PHE  36    -18.618 -13.250  49.295  1.00 00.00
ATOM    213  CE2  PHE  36    -20.826 -14.220  49.043  1.00 00.00
```

Fig. 2 cont.

```
ATOM    214  CZ   PHE    36     -20.004 -13.080  49.223  1.00 00.00
ATOM    215  N    VAL    37     -16.257 -17.020  51.274  1.00 00.00
ATOM    216  CA   VAL    37     -15.434 -16.276  52.240  1.00 00.00
ATOM    217  C    VAL    37     -14.135 -15.854  51.537  1.00 00.00
ATOM    218  O    VAL    37     -13.546 -16.620  50.788  1.00 00.00
ATOM    219  CB   VAL    37     -15.085 -17.120  53.503  1.00 00.00
ATOM    220  CG1  VAL    37     -14.302 -18.381  53.129  1.00 00.00
ATOM    221  CG2  VAL    37     -14.229 -16.274  54.528  1.00 00.00
ATOM    222  N    MET    38     -13.712 -14.605  51.771  1.00 00.00
ATOM    223  CA   MET    38     -12.444 -14.099  51.248  1.00 00.00
ATOM    224  C    MET    38     -11.482 -14.089  52.420  1.00 00.00
ATOM    225  O    MET    38     -11.850 -13.665  53.501  1.00 00.00
ATOM    226  CB   MET    38     -12.607 -12.649  50.727  1.00 00.00
ATOM    227  CG   MET    38     -13.213 -12.515  49.329  1.00 00.00
ATOM    228  SD   MET    38     -14.982 -12.404  49.411  1.00 00.00
ATOM    229  CE   MET    38     -15.173 -10.802  50.183  1.00 00.00
ATOM    230  N    ILE    39     -10.250 -14.517  52.197  1.00 00.00
ATOM    231  CA   ILE    39      -9.335 -14.758  53.301  1.00 00.00
ATOM    232  C    ILE    39      -8.050 -13.982  53.061  1.00 00.00
ATOM    233  O    ILE    39      -7.419 -14.154  52.029  1.00 00.00
ATOM    234  CB   ILE    39      -8.986 -16.280  53.416  1.00 00.00
ATOM    235  CG1  ILE    39     -10.251 -17.132  53.497  1.00 00.00
ATOM    236  CG2  ILE    39      -8.033 -16.530  54.642  1.00 00.00
ATOM    237  CD1  ILE    39      -9.966 -18.713  53.417  1.00 00.00
ATOM    238  N    LYS    40      -7.588 -13.194  54.038  1.00 00.00
ATOM    239  CA   LYS    40      -6.342 -12.427  53.837  1.00 00.00
ATOM    240  C    LYS    40      -5.196 -13.373  53.641  1.00 00.00
ATOM    241  O    LYS    40      -5.013 -14.295  54.468  1.00 00.00
ATOM    242  CB   LYS    40      -5.989 -11.539  55.056  1.00 00.00
ATOM    243  CG   LYS    40      -4.704 -10.678  54.829  1.00 00.00
ATOM    244  CD   LYS    40      -4.516  -9.647  55.923  1.00 00.00
ATOM    245  CE   LYS    40      -3.269  -8.803  55.706  1.00 00.00
ATOM    246  NZ   LYS    40      -3.117  -7.910  56.928  1.00 00.00
ATOM    247  N    ALA    41      -4.376 -13.104  52.609  1.00 00.00
ATOM    248  CA   ALA    41      -3.242 -13.967  52.310  1.00 00.00
ATOM    249  C    ALA    41      -1.964 -13.274  52.649  1.00 00.00
ATOM    250  O    ALA    41      -1.095 -13.867  53.289  1.00 00.00
ATOM    251  CB   ALA    41      -3.237 -14.366  50.858  1.00 00.00
ATOM    252  N    THR    42      -1.837 -12.008  52.209  1.00 00.00
ATOM    253  CA   THR    42      -0.564 -11.305  52.195  1.00 00.00
ATOM    254  C    THR    42      -0.805  -9.798  52.426  1.00 00.00
ATOM    255  O    THR    42      -1.947  -9.324  52.299  1.00 00.00
ATOM    256  CB   THR    42       0.180 -11.483  50.837  1.00 00.00
ATOM    257  CG2  THR    42       0.656 -12.910  50.657  1.00 00.00
ATOM    258  OG1  THR    42      -0.716 -11.205  49.756  1.00 00.00
ATOM    259  N    GLU    43       0.250  -9.105  52.829  1.00 00.00
ATOM    260  CA   GLU    43       0.251  -7.662  52.980  1.00 00.00
ATOM    261  C    GLU    43       1.603  -7.121  52.523  1.00 00.00
ATOM    262  O    GLU    43       2.667  -7.660  52.883  1.00 00.00
ATOM    263  CB   GLU    43      -0.001  -7.299  54.462  1.00 00.00
ATOM    264  CG   GLU    43       0.111  -5.763  54.662  1.00 00.00
ATOM    265  CD   GLU    43      -0.359  -5.268  56.001  1.00 00.00
ATOM    266  OE1  GLU    43      -1.244  -5.902  56.567  1.00 00.00
ATOM    267  OE2  GLU    43       0.122  -4.190  56.442  1.00 00.00
ATOM    268  N    GLY    44       1.559  -6.047  51.726  1.00 00.00
ATOM    269  CA   GLY    44       2.763  -5.329  51.309  1.00 00.00
ATOM    270  C    GLY    44       3.693  -6.290  50.611  1.00 00.00
ATOM    271  O    GLY    44       3.239  -7.188  49.879  1.00 00.00
ATOM    272  N    THR    45       4.984  -6.106  50.856  1.00 00.00
ATOM    273  CA   THR    45       6.014  -6.803  50.104  1.00 00.00
ATOM    274  C    THR    45       6.411  -8.211  50.640  1.00 00.00
ATOM    275  O    THR    45       6.626  -9.141  49.828  1.00 00.00
ATOM    276  CB   THR    45       7.254  -5.901  49.937  1.00 00.00
ATOM    277  CG2  THR    45       6.838  -4.553  49.522  1.00 00.00
ATOM    278  OG1  THR    45       7.925  -5.743  51.188  1.00 00.00
ATOM    279  N    THR    46       6.442  -8.376  51.971  1.00 00.00
ATOM    280  CA   THR    46       7.048  -9.577  52.633  1.00 00.00
ATOM    281  C    THR    46       6.116 -10.293  53.649  1.00 00.00
ATOM    282  O    THR    46       6.461 -11.389  54.162  1.00 00.00
ATOM    283  CB   THR    46       8.324  -9.204  53.387  1.00 00.00
```

Fig. 2 cont.

```
ATOM    284  CG2 THR    46       9.464  -8.779  52.442  1.00 00.00
ATOM    285  OG1 THR    46       8.065  -8.130  54.292  1.00 00.00
ATOM    286  N   TYR    47       4.946  -9.708  53.922  1.00 00.00
ATOM    287  CA  TYR    47       4.113 -10.168  55.060  1.00 00.00
ATOM    288  C   TYR    47       3.129 -11.195  54.613  1.00 00.00
ATOM    289  O   TYR    47       2.290 -10.950  53.712  1.00 00.00
ATOM    290  CB  TYR    47       3.414  -8.971  55.723  1.00 00.00
ATOM    291  CG  TYR    47       2.487  -9.282  56.900  1.00 00.00
ATOM    292  CD1 TYR    47       1.237  -9.837  56.693  1.00 00.00
ATOM    293  CD2 TYR    47       2.856  -8.936  58.216  1.00 00.00
ATOM    294  CE1 TYR    47       0.351 -10.121  57.784  1.00 00.00
ATOM    295  CE2 TYR    47       1.995  -9.196  59.311  1.00 00.00
ATOM    296  CZ  TYR    47       0.736  -9.795  59.083  1.00 00.00
ATOM    297  OH  TYR    47      -0.175 -10.038  60.151  1.00 00.00
ATOM    298  N   LYS    48       3.216 -12.371  55.236  1.00 00.00
ATOM    299  CA  LYS    48       2.213 -13.397  55.061  1.00 00.00
ATOM    300  C   LYS    48       1.282 -13.425  56.290  1.00 00.00
ATOM    301  O   LYS    48       1.741 -13.390  57.431  1.00 00.00
ATOM    302  CB  LYS    48       2.879 -14.753  54.941  1.00 00.00
ATOM    303  CG  LYS    48       3.953 -14.823  53.903  1.00 00.00
ATOM    304  CD  LYS    48       4.330 -16.291  53.680  1.00 00.00
ATOM    305  CE  LYS    48       5.607 -16.397  52.885  1.00 00.00
ATOM    306  NZ  LYS    48       6.766 -16.125  53.757  1.00 00.00
ATOM    307  N   ASP    49      -0.019 -13.479  56.049  1.00 00.00
ATOM    308  CA  ASP    49      -0.941 -13.692  57.131  1.00 00.00
ATOM    309  C   ASP    49      -0.831 -15.178  57.469  1.00 00.00
ATOM    310  O   ASP    49      -1.130 -16.054  56.646  1.00 00.00
ATOM    311  CB  ASP    49      -2.358 -13.326  56.710  1.00 00.00
ATOM    312  CG  ASP    49      -3.334 -13.430  57.835  1.00 00.00
ATOM    313  OD1 ASP    49      -3.444 -14.515  58.445  1.00 00.00
ATOM    314  OD2 ASP    49      -3.999 -12.431  58.141  1.00 00.00
ATOM    315  N   THR    50      -0.355 -15.458  58.673  1.00 00.00
ATOM    316  CA  THR    50       0.071 -16.805  59.015  1.00 00.00
ATOM    317  C   THR    50      -1.123 -17.697  59.384  1.00 00.00
ATOM    318  O   THR    50      -0.932 -18.901  59.624  1.00 00.00
ATOM    319  CB  THR    50       1.121 -16.753  60.125  1.00 00.00
ATOM    320  CG2 THR    50       2.392 -16.224  59.547  1.00 00.00
ATOM    321  OG1 THR    50       0.683 -15.842  61.146  1.00 00.00
ATOM    322  N   VAL    51      -2.337 -17.130  59.414  1.00 00.00
ATOM    323  CA  VAL    51      -3.560 -17.919  59.651  1.00 00.00
ATOM    324  C   VAL    51      -4.229 -18.321  58.310  1.00 00.00
ATOM    325  O   VAL    51      -5.203 -19.058  58.282  1.00 00.00
ATOM    326  CB  VAL    51      -4.585 -17.158  60.614  1.00 00.00
ATOM    327  CG1 VAL    51      -5.607 -18.090  61.122  1.00 00.00
ATOM    328  CG2 VAL    51      -3.842 -16.525  61.837  1.00 00.00
ATOM    329  N   PHE    52      -3.723 -17.770  57.214  1.00 00.00
ATOM    330  CA  PHE    52      -4.267 -18.064  55.888  1.00 00.00
ATOM    331  C   PHE    52      -4.478 -19.572  55.604  1.00 00.00
ATOM    332  O   PHE    52      -5.538 -19.985  55.193  1.00 00.00
ATOM    333  CB  PHE    52      -3.377 -17.462  54.788  1.00 00.00
ATOM    334  CG  PHE    52      -3.868 -17.819  53.383  1.00 00.00
ATOM    335  CD1 PHE    52      -4.975 -17.182  52.840  1.00 00.00
ATOM    336  CD2 PHE    52      -3.250 -18.854  52.658  1.00 00.00
ATOM    337  CE1 PHE    52      -5.485 -17.549  51.601  1.00 00.00
ATOM    338  CE2 PHE    52      -3.752 -19.252  51.394  1.00 00.00
ATOM    339  CZ  PHE    52      -4.845 -18.584  50.851  1.00 00.00
ATOM    340  N   ASN    53      -3.450 -20.381  55.788  1.00 00.00
ATOM    341  CA  ASN    53      -3.631 -21.839  55.517  1.00 00.00
ATOM    342  C   ASN    53      -4.740 -22.523  56.341  1.00 00.00
ATOM    343  O   ASN    53      -5.594 -23.248  55.789  1.00 00.00
ATOM    344  CB  ASN    53      -2.302 -22.581  55.632  1.00 00.00
ATOM    345  CG  ASN    53      -1.300 -22.172  54.547  1.00 00.00
ATOM    346  ND2 ASN    53      -0.006 -22.172  54.898  1.00 00.00
ATOM    347  OD1 ASN    53      -1.682 -21.854  53.412  1.00 00.00
ATOM    348  N   SER    54      -4.774 -22.251  57.645  1.00 00.00
ATOM    349  CA  SER    54      -5.810 -22.829  58.522  1.00 00.00
ATOM    350  C   SER    54      -7.228 -22.369  58.135  1.00 00.00
ATOM    351  O   SER    54      -8.181 -23.170  58.142  1.00 00.00
ATOM    352  CB  SER    54      -5.528 -22.552  60.008  1.00 00.00
ATOM    353  OG  SER    54      -5.537 -21.183  60.296  1.00 00.00
ATOM    354  N   HIS    55      -7.380 -21.087  57.762  1.00 00.00
ATOM    355  CA  HIS    55      -8.674 -20.617  57.314  1.00 00.00
```

Fig. 2 cont.

```
ATOM    356  C   HIS    55      -9.166 -21.256  56.003  1.00 00.00
ATOM    357  O   HIS    55     -10.389 -21.570  55.845  1.00 00.00
ATOM    358  CB  HIS    55      -8.616 -19.117  57.105  1.00 00.00
ATOM    359  CG  HIS    55      -8.595 -18.338  58.370  1.00 00.00
ATOM    360  CD2 HIS    55      -8.124 -17.093  58.649  1.00 00.00
ATOM    361  ND1 HIS    55      -9.164 -18.811  59.540  1.00 00.00
ATOM    362  CE1 HIS    55      -9.001 -17.911  60.492  1.00 00.00
ATOM    363  NE2 HIS    55      -8.421 -16.843  59.970  1.00 00.00
ATOM    364  N   TYR    56      -8.235 -21.358  55.058  1.00 00.00
ATOM    365  CA  TYR    56      -8.513 -21.874  53.722  1.00 00.00
ATOM    366  C   TYR    56      -8.930 -23.335  53.842  1.00 00.00
ATOM    367  O   TYR    56      -9.947 -23.715  53.303  1.00 00.00
ATOM    368  CB  TYR    56      -7.254 -21.742  52.865  1.00 00.00
ATOM    369  CG  TYR    56      -7.449 -21.563  51.358  1.00 00.00
ATOM    370  CD1 TYR    56      -7.596 -20.278  50.788  1.00 00.00
ATOM    371  CD2 TYR    56      -7.348 -22.659  50.490  1.00 00.00
ATOM    372  CE1 TYR    56      -7.719 -20.092  49.395  1.00 00.00
ATOM    373  CE2 TYR    56      -7.478 -22.497  49.097  1.00 00.00
ATOM    374  CZ  TYR    56      -7.657 -21.207  48.553  1.00 00.00
ATOM    375  OH  TYR    56      -7.754 -21.041  47.169  1.00 00.00
ATOM    376  N   THR    57      -8.169 -24.121  54.610  1.00 00.00
ATOM    377  CA  THR    57      -8.537 -25.526  54.906  1.00 00.00
ATOM    378  C   THR    57      -9.903 -25.634  55.604  1.00 00.00
ATOM    379  O   THR    57     -10.741 -26.442  55.225  1.00 00.00
ATOM    380  CB  THR    57      -7.397 -26.228  55.744  1.00 00.00
ATOM    381  CG2 THR    57      -7.696 -27.714  55.966  1.00 00.00
ATOM    382  OG1 THR    57      -6.136 -26.079  55.062  1.00 00.00
ATOM    383  N   GLY    58     -10.139 -24.807  56.606  1.00 00.00
ATOM    384  CA  GLY    58     -11.430 -24.767  57.281  1.00 00.00
ATOM    385  C   GLY    58     -12.604 -24.461  56.359  1.00 00.00
ATOM    386  O   GLY    58     -13.662 -25.091  56.478  1.00 00.00
ATOM    387  N   ALA    59     -12.437 -23.472  55.473  1.00 00.00
ATOM    388  CA  ALA    59     -13.496 -23.068  54.528  1.00 00.00
ATOM    389  C   ALA    59     -13.831 -24.176  53.500  1.00 00.00
ATOM    390  O   ALA    59     -15.006 -24.467  53.218  1.00 00.00
ATOM    391  CB  ALA    59     -13.076 -21.767  53.781  1.00 00.00
ATOM    392  N   THR    60     -12.786 -24.744  52.920  1.00 00.00
ATOM    393  CA  THR    60     -12.887 -25.931  52.074  1.00 00.00
ATOM    394  C   THR    60     -13.697 -27.075  52.751  1.00 00.00
ATOM    395  O   THR    60     -14.677 -27.552  52.199  1.00 00.00
ATOM    396  CB  THR    60     -11.483 -26.414  51.712  1.00 00.00
ATOM    397  CG2 THR    60     -11.527 -27.629  50.789  1.00 00.00
ATOM    398  OG1 THR    60     -10.777 -25.348  51.061  1.00 00.00
ATOM    399  N   LYS    61     -13.300 -27.452  53.964  1.00 00.00
ATOM    400  CA  LYS    61     -13.924 -28.560  54.694  1.00 00.00
ATOM    401  C   LYS    61     -15.385 -28.298  54.983  1.00 00.00
ATOM    402  O   LYS    61     -16.198 -29.244  55.082  1.00 00.00
ATOM    403  CB  LYS    61     -13.151 -28.832  55.995  1.00 00.00
ATOM    404  CG  LYS    61     -13.634 -30.092  56.727  1.00 00.00
ATOM    405  CD  LYS    61     -12.678 -30.513  57.837  1.00 00.00
ATOM    406  CE  LYS    61     -12.619 -29.496  58.971  1.00 00.00
ATOM    407  NZ  LYS    61     -13.946 -29.269  59.608  1.00 00.00
ATOM    408  N   ALA    62     -15.744 -27.009  55.068  1.00 00.00
ATOM    409  CA  ALA    62     -17.116 -26.609  55.309  1.00 00.00
ATOM    410  C   ALA    62     -17.898 -26.530  54.026  1.00 00.00
ATOM    411  O   ALA    62     -19.090 -26.289  54.067  1.00 00.00
ATOM    412  CB  ALA    62     -17.186 -25.236  56.023  1.00 00.00
ATOM    413  N   GLY    63     -17.219 -26.683  52.899  1.00 00.00
ATOM    414  CA  GLY    63     -17.834 -26.524  51.582  1.00 00.00
ATOM    415  C   GLY    63     -18.064 -25.080  51.152  1.00 00.00
ATOM    416  O   GLY    63     -19.024 -24.796  50.438  1.00 00.00
ATOM    417  N   LEU    64     -17.226 -24.154  51.613  1.00 00.00
ATOM    418  CA  LEU    64     -17.425 -22.739  51.241  1.00 00.00
ATOM    419  C   LEU    64     -16.584 -22.441  50.015  1.00 00.00
ATOM    420  O   LEU    64     -15.507 -23.002  49.863  1.00 00.00
ATOM    421  CB  LEU    64     -17.052 -21.799  52.399  1.00 00.00
ATOM    422  CG  LEU    64     -18.039 -21.725  53.553  1.00 00.00
ATOM    423  CD1 LEU    64     -17.450 -21.080  54.781  1.00 00.00
ATOM    424  CD2 LEU    64     -19.337 -21.018  53.185  1.00 00.00
ATOM    425  N   LEU    65     -17.101 -21.609  49.101  1.00 00.00
ATOM    426  CA  LEU    65     -16.238 -21.010  48.071  1.00 00.00
ATOM    427  C   LEU    65     -15.306 -20.085  48.870  1.00 00.00
```

Fig. 2 cont.

```
ATOM    428  O   LEU    65    -15.729  -19.537  49.912  1.00 00.00
ATOM    429  CB  LEU    65    -17.065  -20.153  47.110  1.00 00.00
ATOM    430  CG  LEU    65    -17.990  -20.945  46.176  1.00 00.00
ATOM    431  CD1 LEU    65    -18.947  -20.003  45.497  1.00 00.00
ATOM    432  CD2 LEU    65    -17.204  -21.791  45.151  1.00 00.00
ATOM    433  N   ARG    66    -14.078  -19.961  48.402  1.00 00.00
ATOM    434  CA  ARG    66    -13.029  -19.185  49.097  1.00 00.00
ATOM    435  C   ARG    66    -12.027  -18.657  48.078  1.00 00.00
ATOM    436  O   ARG    66    -11.793  -19.308  47.057  1.00 00.00
ATOM    437  CB  ARG    66    -12.294  -20.027  50.170  1.00 00.00
ATOM    438  CG  ARG    66    -11.337  -21.129  49.682  1.00 00.00
ATOM    439  CD  ARG    66    -12.153  -22.402  49.334  1.00 00.00
ATOM    440  NE  ARG    66    -11.291  -23.524  48.936  1.00 00.00
ATOM    441  CZ  ARG    66    -10.569  -23.566  47.808  1.00 00.00
ATOM    442  NH1 ARG    66    -10.593  -22.558  46.942  1.00 00.00
ATOM    443  NH2 ARG    66     -9.812  -24.633  47.534  1.00 00.00
ATOM    444  N   GLY    67    -11.443  -17.485  48.360  1.00 00.00
ATOM    445  CA  GLY    67    -10.264  -17.002  47.676  1.00 00.00
ATOM    446  C   GLY    67     -9.436  -16.150  48.641  1.00 00.00
ATOM    447  O   GLY    67     -9.877  -15.866  49.784  1.00 00.00
ATOM    448  N   GLY    68     -8.261  -15.751  48.192  1.00 00.00
ATOM    449  CA  GLY    68     -7.318  -14.942  48.984  1.00 00.00
ATOM    450  C   GLY    68     -7.511  -13.446  48.731  1.00 00.00
ATOM    451  O   GLY    68     -8.049  -13.045  47.681  1.00 00.00
ATOM    452  N   TYR    69     -7.102  -12.616  49.694  1.00 00.00
ATOM    453  CA  TYR    69     -6.909  -11.180  49.393  1.00 00.00
ATOM    454  C   TYR    69     -5.582  -10.629  49.818  1.00 00.00
ATOM    455  O   TYR    69     -4.929  -11.172  50.682  1.00 00.00
ATOM    456  CB  TYR    69     -8.075  -10.327  49.852  1.00 00.00
ATOM    457  CG  TYR    69     -8.200  -10.057  51.338  1.00 00.00
ATOM    458  CD1 TYR    69     -7.430   -9.058  51.960  1.00 00.00
ATOM    459  CD2 TYR    69     -9.137  -10.752  52.098  1.00 00.00
ATOM    460  CE1 TYR    69     -7.610   -8.772  53.340  1.00 00.00
ATOM    461  CE2 TYR    69     -9.346  -10.462  53.467  1.00 00.00
ATOM    462  CZ  TYR    69     -8.595   -9.466  54.067  1.00 00.00
ATOM    463  OH  TYR    69     -8.785   -9.212  55.420  1.00 00.00
ATOM    464  N   HIS    70     -5.189   -9.527  49.212  1.00 00.00
ATOM    465  CA  HIS    70     -3.896   -8.931  49.465  1.00 00.00
ATOM    466  C   HIS    70     -4.140   -7.548  50.035  1.00 00.00
ATOM    467  O   HIS    70     -4.840   -6.756  49.397  1.00 00.00
ATOM    468  CB  HIS    70     -3.127   -8.750  48.162  1.00 00.00
ATOM    469  CG  HIS    70     -1.802   -8.040  48.337  1.00 00.00
ATOM    470  CD2 HIS    70     -1.430   -6.753  48.091  1.00 00.00
ATOM    471  ND1 HIS    70     -0.708   -8.645  48.906  1.00 00.00
ATOM    472  CE1 HIS    70      0.290   -7.782  48.971  1.00 00.00
ATOM    473  NE2 HIS    70     -0.112   -6.638  48.454  1.00 00.00
ATOM    474  N   PHE    71     -3.499   -7.224  51.167  1.00 00.00
ATOM    475  CA  PHE    71     -3.603   -5.837  51.661  1.00 00.00
ATOM    476  C   PHE    71     -2.526   -4.976  51.067  1.00 00.00
ATOM    477  O   PHE    71     -1.341   -5.121  51.410  1.00 00.00
ATOM    478  CB  PHE    71     -3.578   -5.702  53.192  1.00 00.00
ATOM    479  CG  PHE    71     -3.954   -4.320  53.634  1.00 00.00
ATOM    480  CD1 PHE    71     -3.006   -3.323  53.747  1.00 00.00
ATOM    481  CD2 PHE    71     -5.307   -4.015  53.826  1.00 00.00
ATOM    482  CE1 PHE    71     -3.380   -2.027  54.117  1.00 00.00
ATOM    483  CE2 PHE    71     -5.719   -2.717  54.163  1.00 00.00
ATOM    484  CZ  PHE    71     -4.748   -1.718  54.284  1.00 00.00
ATOM    485  N   ALA    72     -2.944   -4.058  50.168  1.00 00.00
ATOM    486  CA  ALA    72     -2.004   -3.226  49.403  1.00 00.00
ATOM    487  C   ALA    72     -1.188   -2.305  50.310  1.00 00.00
ATOM    488  O   ALA    72     -1.701   -1.754  51.285  1.00 00.00
ATOM    489  CB  ALA    72     -2.781   -2.368  48.351  1.00 00.00
ATOM    490  N   ARG    73      0.096   -2.224  50.062  1.00 00.00
ATOM    491  CA  ARG    73      0.882   -1.120  50.608  1.00 00.00
ATOM    492  C   ARG    73      1.680   -0.471  49.498  1.00 00.00
ATOM    493  O   ARG    73      2.851   -0.788  49.254  1.00 00.00
ATOM    494  CB  ARG    73      1.717   -1.485  51.842  1.00 00.00
ATOM    495  CG  ARG    73      0.909   -1.306  53.170  1.00 00.00
ATOM    496  CD  ARG    73      1.671   -0.452  54.186  1.00 00.00
ATOM    497  NE  ARG    73      2.622   -1.273  54.925  1.00 00.00
ATOM    498  CZ  ARG    73      3.667   -0.831  55.615  1.00 00.00
ATOM    499  NH1 ARG    73      3.957    0.454  55.682  1.00 00.00
```

Fig. 2 cont.

```
ATOM    500  NH2 ARG    73       4.435  -1.706  56.242  1.00 00.00
ATOM    501  N   PRO    74       1.021   0.477  48.803  1.00 00.00
ATOM    502  CA  PRO    74       1.533   0.988  47.540  1.00 00.00
ATOM    503  C   PRO    74       2.798   1.802  47.649  1.00 00.00
ATOM    504  O   PRO    74       3.424   2.015  46.636  1.00 00.00
ATOM    505  CB  PRO    74       0.394   1.861  47.047  1.00 00.00
ATOM    506  CG  PRO    74      -0.807   1.139  47.540  1.00 00.00
ATOM    507  CD  PRO    74      -0.406   0.836  48.970  1.00 00.00
ATOM    508  N   ASP    75       3.197   2.228  48.854  1.00 00.00
ATOM    509  CA  ASP    75       4.460   2.972  48.997  1.00 00.00
ATOM    510  C   ASP    75       5.688   2.077  49.203  1.00 00.00
ATOM    511  O   ASP    75       6.815   2.578  49.249  1.00 00.00
ATOM    512  CB  ASP    75       4.374   3.952  50.154  1.00 00.00
ATOM    513  CG  ASP    75       3.983   3.278  51.485  1.00 00.00
ATOM    514  OD1 ASP    75       3.317   2.209  51.493  1.00 00.00
ATOM    515  OD2 ASP    75       4.292   3.869  52.552  1.00 00.00
ATOM    516  N   LYS    76       5.472   0.779  49.337  1.00 00.00
ATOM    517  CA  LYS    76       6.556  -0.127  49.707  1.00 00.00
ATOM    518  C   LYS    76       7.246  -0.795  48.494  1.00 00.00
ATOM    519  O   LYS    76       8.377  -1.267  48.598  1.00 00.00
ATOM    520  CB  LYS    76       6.041  -1.188  50.688  1.00 00.00
ATOM    521  CG  LYS    76       5.634  -0.626  52.050  1.00 00.00
ATOM    522  CD  LYS    76       6.800   0.162  52.665  1.00 00.00
ATOM    523  CE  LYS    76       6.376   0.919  53.927  1.00 00.00
ATOM    524  NZ  LYS    76       7.562   1.442  54.677  1.00 00.00
ATOM    525  N   SER    77       6.550  -0.881  47.360  1.00 00.00
ATOM    526  CA  SER    77       7.126  -1.511  46.153  1.00 00.00
ATOM    527  C   SER    77       6.153  -1.276  45.013  1.00 00.00
ATOM    528  O   SER    77       5.168  -0.565  45.190  1.00 00.00
ATOM    529  CB  SER    77       7.254  -3.011  46.351  1.00 00.00
ATOM    530  OG  SER    77       5.987  -3.582  46.215  1.00 00.00
ATOM    531  N   THR    78       6.333  -1.977  43.892  1.00 00.00
ATOM    532  CA  THR    78       5.391  -1.811  42.775  1.00 00.00
ATOM    533  C   THR    78       4.171  -2.720  42.870  1.00 00.00
ATOM    534  O   THR    78       4.140  -3.726  43.601  1.00 00.00
ATOM    535  CB  THR    78       6.085  -2.040  41.404  1.00 00.00
ATOM    536  CG2 THR    78       7.282  -1.136  41.239  1.00 00.00
ATOM    537  OG1 THR    78       6.516  -3.391  41.322  1.00 00.00
ATOM    538  N   GLY    79       3.146  -2.384  42.087  1.00 00.00
ATOM    539  CA  GLY    79       1.949  -3.206  42.029  1.00 00.00
ATOM    540  C   GLY    79       2.300  -4.587  41.547  1.00 00.00
ATOM    541  O   GLY    79       1.771  -5.552  42.052  1.00 00.00
ATOM    542  N   SER    80       3.197  -4.697  40.562  1.00 00.00
ATOM    543  CA  SER    80       3.641  -6.007  40.051  1.00 00.00
ATOM    544  C   SER    80       4.336  -6.868  41.124  1.00 00.00
ATOM    545  O   SER    80       4.074  -8.059  41.263  1.00 00.00
ATOM    546  CB  SER    80       4.563  -5.822  38.839  1.00 00.00
ATOM    547  OG  SER    80       5.198  -7.045  38.512  1.00 00.00
ATOM    548  N   THR    81       5.217  -6.242  41.896  1.00 00.00
ATOM    549  CA  THR    81       5.948  -6.982  42.937  1.00 00.00
ATOM    550  C   THR    81       4.996  -7.594  43.931  1.00 00.00
ATOM    551  O   THR    81       5.105  -8.781  44.296  1.00 00.00
ATOM    552  CB  THR    81       6.941  -6.075  43.663  1.00 00.00
ATOM    553  CG2 THR    81       7.538  -6.803  44.899  1.00 00.00
ATOM    554  OG1 THR    81       7.972  -5.728  42.767  1.00 00.00
ATOM    555  N   GLN    82       4.007  -6.796  44.360  1.00 00.00
ATOM    556  CA  GLN    82       3.046  -7.290  45.306  1.00 00.00
ATOM    557  C   GLN    82       2.059  -8.279  44.705  1.00 00.00
ATOM    558  O   GLN    82       1.654  -9.201  45.382  1.00 00.00
ATOM    559  CB  GLN    82       2.353  -6.104  46.081  1.00 00.00
ATOM    560  CG  GLN    82       3.363  -5.365  46.993  1.00 00.00
ATOM    561  CD  GLN    82       2.752  -4.200  47.749  1.00 00.00
ATOM    562  NE2 GLN    82       3.539  -3.126  47.921  1.00 00.00
ATOM    563  OE1 GLN    82       1.581  -4.253  48.160  1.00 00.00
ATOM    564  N   ALA    83       1.688  -8.119  43.420  1.00 00.00
ATOM    565  CA  ALA    83       0.824  -9.114  42.811  1.00 00.00
ATOM    566  C   ALA    83       1.566 -10.480  42.805  1.00 00.00
ATOM    567  O   ALA    83       0.964 -11.501  43.103  1.00 00.00
ATOM    568  CB  ALA    83       0.388  -8.678  41.353  1.00 00.00
ATOM    569  N   LYS    84       2.853 -10.452  42.466  1.00 00.00
ATOM    570  CA  LYS    84       3.687 -11.688  42.352  1.00 00.00
ATOM    571  C   LYS    84       3.783 -12.399  43.726  1.00 00.00
```

Fig. 2 cont.

```
ATOM    572  O   LYS   84       3.603 -13.608  43.823  1.00 00.00
ATOM    573  CB  LYS   84       5.071 -11.326  41.824  1.00 00.00
ATOM    574  CG  LYS   84       5.180 -11.129  40.283  1.00 00.00
ATOM    575  CD  LYS   84       6.454 -10.338  39.967  1.00 00.00
ATOM    576  CE  LYS   84       6.793 -10.243  38.469  1.00 00.00
ATOM    577  NZ  LYS   84       7.901  -9.228  38.300  1.00 00.00
ATOM    578  N   PHE   85       3.962 -11.608  44.777  1.00 00.00
ATOM    579  CA  PHE   85       4.001 -12.098  46.158  1.00 00.00
ATOM    580  C   PHE   85       2.686 -12.741  46.629  1.00 00.00
ATOM    581  O   PHE   85       2.692 -13.875  47.130  1.00 00.00
ATOM    582  CB  PHE   85       4.477 -10.964  47.103  1.00 00.00
ATOM    583  CG  PHE   85       4.546 -11.371  48.537  1.00 00.00
ATOM    584  CD1 PHE   85       5.307 -12.486  48.937  1.00 00.00
ATOM    585  CD2 PHE   85       3.859 -10.629  49.523  1.00 00.00
ATOM    586  CE1 PHE   85       5.372 -12.886  50.312  1.00 00.00
ATOM    587  CE2 PHE   85       3.918 -11.034  50.883  1.00 00.00
ATOM    588  CZ  PHE   85       4.691 -12.168  51.259  1.00 00.00
ATOM    589  N   PHE   86       1.563 -12.068  46.372  1.00 00.00
ATOM    590  CA  PHE   86       0.206 -12.568  46.648  1.00 00.00
ATOM    591  C   PHE   86      -0.029 -13.880  45.911  1.00 00.00
ATOM    592  O   PHE   86      -0.539 -14.851  46.484  1.00 00.00
ATOM    593  CB  PHE   86      -0.785 -11.477  46.139  1.00 00.00
ATOM    594  CG  PHE   86      -2.227 -11.832  46.220  1.00 00.00
ATOM    595  CD1 PHE   86      -2.769 -12.351  47.385  1.00 00.00
ATOM    596  CD2 PHE   86      -3.082 -11.510  45.157  1.00 00.00
ATOM    597  CE1 PHE   86      -4.107 -12.576  47.487  1.00 00.00
ATOM    598  CE2 PHE   86      -4.413 -11.731  45.241  1.00 00.00
ATOM    599  CZ  PHE   86      -4.956 -12.287  46.393  1.00 00.00
ATOM    600  N   LEU   87       0.335 -13.894  44.627  1.00 00.00
ATOM    601  CA  LEU   87       0.094 -15.061  43.757  1.00 00.00
ATOM    602  C   LEU   87       0.838 -16.300  44.281  1.00 00.00
ATOM    603  O   LEU   87       0.363 -17.426  44.132  1.00 00.00
ATOM    604  CB  LEU   87       0.553 -14.738  42.304  1.00 00.00
ATOM    605  CG  LEU   87      -0.384 -13.866  41.437  1.00 00.00
ATOM    606  CD1 LEU   87       0.349 -13.134  40.290  1.00 00.00
ATOM    607  CD2 LEU   87      -1.536 -14.647  40.965  1.00 00.00
ATOM    608  N   LYS   88       2.007 -16.082  44.859  1.00 00.00
ATOM    609  CA  LYS   88       2.810 -17.184  45.413  1.00 00.00
ATOM    610  C   LYS   88       2.296 -17.675  46.762  1.00 00.00
ATOM    611  O   LYS   88       2.643 -18.767  47.223  1.00 00.00
ATOM    612  CB  LYS   88       4.238 -16.742  45.594  1.00 00.00
ATOM    613  CG  LYS   88       5.021 -16.634  44.313  1.00 00.00
ATOM    614  CD  LYS   88       6.498 -16.904  44.538  1.00 00.00
ATOM    615  CE  LYS   88       7.360 -16.108  43.562  1.00 00.00
ATOM    616  NZ  LYS   88       6.546 -15.288  42.557  1.00 00.00
ATOM    617  N   ASN   89       1.458 -16.886  47.404  1.00 00.00
ATOM    618  CA  ASN   89       1.108 -17.159  48.786  1.00 00.00
ATOM    619  C   ASN   89      -0.405 -17.223  49.090  1.00 00.00
ATOM    620  O   ASN   89      -0.866 -16.885  50.177  1.00 00.00
ATOM    621  CB  ASN   89       1.907 -16.215  49.706  1.00 00.00
ATOM    622  CG  ASN   89       3.416 -16.456  49.614  1.00 00.00
ATOM    623  ND2 ASN   89       4.121 -15.600  48.867  1.00 00.00
ATOM    624  OD1 ASN   89       3.940 -17.436  50.193  1.00 00.00
ATOM    625  N   GLY   90      -1.171 -17.740  48.135  1.00 00.00
ATOM    626  CA  GLY   90      -2.577 -18.027  48.350  1.00 00.00
ATOM    627  C   GLY   90      -3.555 -17.176  47.566  1.00 00.00
ATOM    628  O   GLY   90      -4.772 -17.410  47.606  1.00 00.00
ATOM    629  N   GLY   91      -3.058 -16.178  46.859  1.00 00.00
ATOM    630  CA  GLY   91      -3.938 -15.439  45.974  1.00 00.00
ATOM    631  C   GLY   91      -4.109 -16.111  44.626  1.00 00.00
ATOM    632  O   GLY   91      -4.796 -15.563  43.735  1.00 00.00
ATOM    633  N   GLY   92      -3.477 -17.282  44.448  1.00 00.00
ATOM    634  CA  GLY   92      -3.654 -18.048  43.200  1.00 00.00
ATOM    635  C   GLY   92      -5.101 -18.370  42.888  1.00 00.00
ATOM    636  O   GLY   92      -5.973 -18.277  43.755  1.00 00.00
ATOM    637  N   TRP   93      -5.375 -18.731  41.622  1.00 00.00
ATOM    638  CA  TRP   93      -6.733 -19.093  41.197  1.00 00.00
ATOM    639  C   TRP   93      -6.750 -20.276  40.191  1.00 00.00
ATOM    640  O   TRP   93      -5.863 -20.377  39.355  1.00 00.00
ATOM    641  CB  TRP   93      -7.463 -17.866  40.571  1.00 00.00
ATOM    642  CG  TRP   93      -8.811 -18.210  40.022  1.00 00.00
```

Fig. 2 cont.

```
ATOM   643  CD1 TRP   93     -9.983 -18.232  40.696  1.00 00.00
ATOM   644  CD2 TRP   93     -9.105 -18.678  38.681  1.00 00.00
ATOM   645  CE2 TRP   93    -10.506 -18.903  38.618  1.00 00.00
ATOM   646  CE3 TRP   93     -8.324 -18.900  37.533  1.00 00.00
ATOM   647  NE1 TRP   93    -11.013 -18.643  39.864  1.00 00.00
ATOM   648  CZ2 TRP   93    -11.157 -19.381  37.445  1.00 00.00
ATOM   649  CZ3 TRP   93     -8.975 -19.363  36.341  1.00 00.00
ATOM   650  CH2 TRP   93    -10.378 -19.584  36.319  1.00 00.00
ATOM   651  N   SER   94     -7.790 -21.108  40.265  1.00 00.00
ATOM   652  CA  SER   94     -8.094 -22.079  39.205  1.00 00.00
ATOM   653  C   SER   94     -9.591 -22.407  39.137  1.00 00.00
ATOM   654  O   SER   94    -10.377 -22.072  40.027  1.00 00.00
ATOM   655  CB  SER   94     -7.265 -23.356  39.376  1.00 00.00
ATOM   656  OG  SER   94     -7.672 -24.056  40.526  1.00 00.00
ATOM   657  N   ASP   95    -10.010 -23.027  38.044  1.00 00.00
ATOM   658  CA  ASP   95    -11.430 -23.251  37.849  1.00 00.00
ATOM   659  C   ASP   95    -11.807 -24.636  38.381  1.00 00.00
ATOM   660  O   ASP   95    -12.127 -25.545  37.602  1.00 00.00
ATOM   661  CB  ASP   95    -11.813 -23.071  36.368  1.00 00.00
ATOM   662  CG  ASP   95    -13.318 -23.262  36.112  1.00 00.00
ATOM   663  OD1 ASP   95    -14.092 -23.435  37.091  1.00 00.00
ATOM   664  OD2 ASP   95    -13.714 -23.260  34.913  1.00 00.00
ATOM   665  N   ASP   96    -11.813 -24.769  39.706  1.00 00.00
ATOM   666  CA  ASP   96    -11.971 -26.043  40.382  1.00 00.00
ATOM   667  C   ASP   96    -13.288 -26.101  41.116  1.00 00.00
ATOM   668  O   ASP   96    -13.465 -26.906  42.056  1.00 00.00
ATOM   669  CB  ASP   96    -10.823 -26.231  41.368  1.00 00.00
ATOM   670  CG  ASP   96    -10.745 -25.105  42.418  1.00 00.00
ATOM   671  OD1 ASP   96    -11.603 -24.182  42.392  1.00 00.00
ATOM   672  OD2 ASP   96     -9.830 -25.179  43.274  1.00 00.00
ATOM   673  N   ASN   97    -14.214 -25.241  40.695  1.00 00.00
ATOM   674  CA  ASN   97    -15.470 -25.037  41.397  1.00 00.00
ATOM   675  C   ASN   97    -15.367 -24.585  42.868  1.00 00.00
ATOM   676  O   ASN   97    -16.371 -24.604  43.567  1.00 00.00
ATOM   677  CB  ASN   97    -16.374 -26.275  41.295  1.00 00.00
ATOM   678  CG  ASN   97    -16.674 -26.649  39.856  1.00 00.00
ATOM   679  ND2 ASN   97    -16.343 -27.877  39.497  1.00 00.00
ATOM   680  OD1 ASN   97    -17.161 -25.820  39.061  1.00 00.00
ATOM   681  N   ARG   98    -14.180 -24.163  43.311  1.00 00.00
ATOM   682  CA  ARG   98    -13.968 -23.814  44.729  1.00 00.00
ATOM   683  C   ARG   98    -13.493 -22.364  45.007  1.00 00.00
ATOM   684  O   ARG   98    -13.675 -21.853  46.122  1.00 00.00
ATOM   685  CB  ARG   98    -12.931 -24.749  45.327  1.00 00.00
ATOM   686  CG  ARG   98    -13.436 -26.202  45.521  1.00 00.00
ATOM   687  CD  ARG   98    -12.373 -27.053  46.225  1.00 00.00
ATOM   688  NE  ARG   98    -11.061 -27.070  45.547  1.00 00.00
ATOM   689  CZ  ARG   98     -9.948 -27.591  46.094  1.00 00.00
ATOM   690  NH1 ARG   98     -9.991 -28.100  47.334  1.00 00.00
ATOM   691  NH2 ARG   98     -8.789 -27.573  45.438  1.00 00.00
ATOM   692  N   THR   99    -12.908 -21.735  43.994  1.00 00.00
ATOM   693  CA  THR   99    -11.998 -20.601  44.171  1.00 00.00
ATOM   694  C   THR   99    -12.516 -19.347  43.510  1.00 00.00
ATOM   695  O   THR   99    -12.712 -19.311  42.284  1.00 00.00
ATOM   696  CB  THR   99    -10.660 -20.937  43.569  1.00 00.00
ATOM   697  CG2 THR   99     -9.570 -19.965  43.986  1.00 00.00
ATOM   698  OG1 THR   99    -10.307 -22.253  43.990  1.00 00.00
ATOM   699  N   LEU  100    -12.668 -18.298  44.331  1.00 00.00
ATOM   700  CA  LEU  100    -12.957 -16.952  43.855  1.00 00.00
ATOM   701  C   LEU  100    -11.648 -16.325  43.346  1.00 00.00
ATOM   702  O   LEU  100    -10.569 -16.682  43.792  1.00 00.00
ATOM   703  CB  LEU  100    -13.563 -16.092  44.979  1.00 00.00
ATOM   704  CG  LEU  100    -14.828 -16.593  45.699  1.00 00.00
ATOM   705  CD1 LEU  100    -15.037 -15.855  46.982  1.00 00.00
ATOM   706  CD2 LEU  100    -16.035 -16.452  44.848  1.00 00.00
ATOM   707  N   PRO  101    -11.729 -15.397  42.369  1.00 00.00
ATOM   708  CA  PRO  101    -10.499 -14.745  41.937  1.00 00.00
ATOM   709  C   PRO  101     -9.972 -13.905  43.116  1.00 00.00
ATOM   710  O   PRO  101    -10.772 -13.438  43.971  1.00 00.00
ATOM   711  CB  PRO  101    -10.950 -13.840  40.776  1.00 00.00
ATOM   712  CG  PRO  101    -12.401 -13.699  40.965  1.00 00.00
ATOM   713  CD  PRO  101    -12.920 -14.883  41.676  1.00 00.00
ATOM   714  N   GLY  102     -8.664 -13.751  43.203  1.00 00.00
```

Fig. 2 cont.

```
ATOM  715  CA   GLY  102   -8.090 -13.024  44.337  1.00 00.00
ATOM  716  C    GLY  102   -8.581 -11.569  44.324  1.00 00.00
ATOM  717  O    GLY  102   -8.963 -11.038  43.255  1.00 00.00
ATOM  718  N    MET  103   -8.511 -10.943  45.502  1.00 00.00
ATOM  719  CA   MET  103   -8.978  -9.580  45.756  1.00 00.00
ATOM  720  C    MET  103   -7.845  -8.656  46.246  1.00 00.00
ATOM  721  O    MET  103   -7.032  -9.015  47.109  1.00 00.00
ATOM  722  CB   MET  103  -10.097  -9.646  46.810  1.00 00.00
ATOM  723  CG   MET  103  -10.700  -8.315  47.173  1.00 00.00
ATOM  724  SD   MET  103  -12.149  -8.617  48.235  1.00 00.00
ATOM  725  CE   MET  103  -11.403  -8.760  49.886  1.00 00.00
ATOM  726  N    LEU  104   -7.769  -7.496  45.628  1.00 00.00
ATOM  727  CA   LEU  104   -6.893  -6.441  46.080  1.00 00.00
ATOM  728  C    LEU  104   -7.650  -5.531  47.028  1.00 00.00
ATOM  729  O    LEU  104   -8.668  -4.893  46.638  1.00 00.00
ATOM  730  CB   LEU  104   -6.337  -5.666  44.900  1.00 00.00
ATOM  731  CG   LEU  104   -5.498  -4.446  45.214  1.00 00.00
ATOM  732  CD1  LEU  104   -4.135  -4.876  45.742  1.00 00.00
ATOM  733  CD2  LEU  104   -5.398  -3.580  43.919  1.00 00.00
ATOM  734  N    ASP  105   -7.184  -5.504  48.275  1.00 00.00
ATOM  735  CA   ASP  105   -7.726  -4.601  49.299  1.00 00.00
ATOM  736  C    ASP  105   -6.871  -3.344  49.244  1.00 00.00
ATOM  737  O    ASP  105   -5.689  -3.342  49.631  1.00 00.00
ATOM  738  CB   ASP  105   -7.664  -5.311  50.684  1.00 00.00
ATOM  739  CG   ASP  105   -8.160  -4.454  51.829  1.00 00.00
ATOM  740  OD1  ASP  105   -8.236  -3.197  51.706  1.00 00.00
ATOM  741  OD2  ASP  105   -8.409  -5.055  52.899  1.00 00.00
ATOM  742  N    ILE  106   -7.481  -2.281  48.692  1.00 00.00
ATOM  743  CA   ILE  106   -6.790  -1.059  48.354  1.00 00.00
ATOM  744  C    ILE  106   -7.598   0.103  48.907  1.00 00.00
ATOM  745  O    ILE  106   -8.585   0.564  48.316  1.00 00.00
ATOM  746  CB   ILE  106   -6.476  -0.952  46.805  1.00 00.00
ATOM  747  CG1  ILE  106   -5.845   0.406  46.445  1.00 00.00
ATOM  748  CG2  ILE  106   -7.712  -1.202  45.921  1.00 00.00
ATOM  749  CD1  ILE  106   -4.563   0.811  47.271  1.00 00.00
ATOM  750  N    GLU  107   -7.252   0.463  50.138  1.00 00.00
ATOM  751  CA   GLU  107   -7.998   1.507  50.874  1.00 00.00
ATOM  752  C    GLU  107   -7.171   2.068  52.000  1.00 00.00
ATOM  753  O    GLU  107   -5.947   2.142  51.872  1.00 00.00
ATOM  754  CB   GLU  107   -9.426   1.071  51.285  1.00 00.00
ATOM  755  CG   GLU  107   -9.604  -0.381  51.717  1.00 00.00
ATOM  756  CD   GLU  107   -9.318  -0.617  53.205  1.00 00.00
ATOM  757  OE1  GLU  107   -8.897  -1.737  53.570  1.00 00.00
ATOM  758  OE2  GLU  107   -9.587   0.289  54.029  1.00 00.00
ATOM  759  N    TYR  108   -7.827   2.493  53.080  1.00 00.00
ATOM  760  CA   TYR  108   -7.179   3.403  54.076  1.00 00.00
ATOM  761  C    TYR  108   -5.887   2.844  54.641  1.00 00.00
ATOM  762  O    TYR  108   -5.869   1.694  55.086  1.00 00.00
ATOM  763  CB   TYR  108   -8.158   3.739  55.205  1.00 00.00
ATOM  764  CG   TYR  108   -9.459   4.314  54.684  1.00 00.00
ATOM  765  CD1  TYR  108   -9.544   5.659  54.275  1.00 00.00
ATOM  766  CD2  TYR  108  -10.605   3.503  54.564  1.00 00.00
ATOM  767  CE1  TYR  108  -10.798   6.190  53.756  1.00 00.00
ATOM  768  CE2  TYR  108  -11.821   4.020  54.074  1.00 00.00
ATOM  769  CZ   TYR  108  -11.884   5.368  53.679  1.00 00.00
ATOM  770  OH   TYR  108  -13.038   5.848  53.182  1.00 00.00
ATOM  771  N    ASN  109   -4.818   3.655  54.590  1.00 00.00
ATOM  772  CA   ASN  109   -3.501   3.269  55.089  1.00 00.00
ATOM  773  C    ASN  109   -3.543   3.242  56.605  1.00 00.00
ATOM  774  O    ASN  109   -3.800   4.298  57.207  1.00 00.00
ATOM  775  CB   ASN  109   -2.486   4.306  54.670  1.00 00.00
ATOM  776  CG   ASN  109   -1.103   3.977  55.156  1.00 00.00
ATOM  777  ND2  ASN  109   -0.197   4.920  55.001  1.00 00.00
ATOM  778  OD1  ASN  109   -0.862   2.898  55.720  1.00 00.00
ATOM  779  N    PRO  110   -3.341   2.056  57.231  1.00 00.00
ATOM  780  CA   PRO  110   -3.497   2.095  58.688  1.00 00.00
ATOM  781  C    PRO  110   -2.231   2.571  59.360  1.00 00.00
ATOM  782  O    PRO  110   -2.164   2.655  60.602  1.00 00.00
ATOM  783  CB   PRO  110   -3.832   0.641  59.059  1.00 00.00
ATOM  784  CG   PRO  110   -3.392  -0.196  57.900  1.00 00.00
ATOM  785  CD   PRO  110   -3.511   0.689  56.682  1.00 00.00
ATOM  786  N    TYR  111   -1.233   2.908  58.555  1.00 00.00
```

Fig. 2 cont.

```
ATOM    787  CA   TYR  111      0.047    3.295   59.090  1.00 00.00
ATOM    788  C    TYR  111      0.216    4.814   59.063  1.00 00.00
ATOM    789  O    TYR  111      1.278    5.315   59.352  1.00 00.00
ATOM    790  CB   TYR  111      1.161    2.500   58.411  1.00 00.00
ATOM    791  CG   TYR  111      0.878    1.013   58.517  1.00 00.00
ATOM    792  CD1  TYR  111      1.019    0.329   59.732  1.00 00.00
ATOM    793  CD2  TYR  111      0.371    0.299   57.422  1.00 00.00
ATOM    794  CE1  TYR  111      0.710   -1.046   59.828  1.00 00.00
ATOM    795  CE2  TYR  111      0.066   -1.070   57.515  1.00 00.00
ATOM    796  CZ   TYR  111      0.234   -1.729   58.707  1.00 00.00
ATOM    797  OH   TYR  111     -0.063   -3.077   58.761  1.00 00.00
ATOM    798  N    GLY  112     -0.883    5.532   58.837  1.00 00.00
ATOM    799  CA   GLY  112     -0.997    6.953   59.253  1.00 00.00
ATOM    800  C    GLY  112     -0.556    8.016   58.254  1.00 00.00
ATOM    801  O    GLY  112     -0.316    9.194   58.649  1.00 00.00
ATOM    802  N    ALA  113     -0.515    7.646   56.955  1.00 00.00
ATOM    803  CA   ALA  113     -0.138    8.585   55.883  1.00 00.00
ATOM    804  C    ALA  113     -1.154    8.523   54.732  1.00 00.00
ATOM    805  O    ALA  113     -1.342    7.492   54.104  1.00 00.00
ATOM    806  CB   ALA  113      1.310    8.267   55.359  1.00 00.00
ATOM    807  N    THR  114     -1.806    9.637   54.494  1.00 00.00
ATOM    808  CA   THR  114     -2.946    9.707   53.593  1.00 00.00
ATOM    809  C    THR  114     -2.510    9.263   52.192  1.00 00.00
ATOM    810  O    THR  114     -1.486    9.743   51.708  1.00 00.00
ATOM    811  CB   THR  114     -3.407   11.162   53.520  1.00 00.00
ATOM    812  CG2  THR  114     -4.603   11.288   52.654  1.00 00.00
ATOM    813  OG1  THR  114     -3.779   11.539   54.848  1.00 00.00
ATOM    814  N    CYS  115     -3.274    8.325   51.616  1.00 00.00
ATOM    815  CA   CYS  115     -3.018    7.757   50.299  1.00 00.00
ATOM    816  C    CYS  115     -1.619    7.143   50.112  1.00 00.00
ATOM    817  O    CYS  115     -1.124    7.094   48.984  1.00 00.00
ATOM    818  CB   CYS  115     -3.337    8.779   49.186  1.00 00.00
ATOM    819  SG   CYS  115     -5.059    9.434   49.280  1.00 00.00
ATOM    820  N    TYR  116     -0.997    6.676   51.228  1.00 00.00
ATOM    821  CA   TYR  116      0.356    6.082   51.216  1.00 00.00
ATOM    822  C    TYR  116      1.387    7.054   50.629  1.00 00.00
ATOM    823  O    TYR  116      2.472    6.649   50.162  1.00 00.00
ATOM    824  CB   TYR  116      0.344    4.733   50.456  1.00 00.00
ATOM    825  CG   TYR  116     -0.658    3.772   51.011  1.00 00.00
ATOM    826  CD1  TYR  116     -0.301    2.813   51.978  1.00 00.00
ATOM    827  CD2  TYR  116     -1.998    3.802   50.571  1.00 00.00
ATOM    828  CE1  TYR  116     -1.274    1.900   52.482  1.00 00.00
ATOM    829  CE2  TYR  116     -2.953    2.888   51.070  1.00 00.00
ATOM    830  CZ   TYR  116     -2.577    1.960   52.042  1.00 00.00
ATOM    831  OH   TYR  116     -3.546    1.099   52.547  1.00 00.00
ATOM    832  N    GLY  117      1.065    8.343   50.653  1.00 00.00
ATOM    833  CA   GLY  117      2.004    9.361   50.111  1.00 00.00
ATOM    834  C    GLY  117      2.164    9.373   48.590  1.00 00.00
ATOM    835  O    GLY  117      3.049   10.054   48.041  1.00 00.00
ATOM    836  N    LEU  118      1.307    8.633   47.907  1.00 00.00
ATOM    837  CA   LEU  118      1.347    8.606   46.432  1.00 00.00
ATOM    838  C    LEU  118      0.389    9.639   45.837  1.00 00.00
ATOM    839  O    LEU  118     -0.698    9.915   46.390  1.00 00.00
ATOM    840  CB   LEU  118      1.001    7.216   45.895  1.00 00.00
ATOM    841  CG   LEU  118      1.937    6.029   46.062  1.00 00.00
ATOM    842  CD1  LEU  118      1.462    4.913   45.082  1.00 00.00
ATOM    843  CD2  LEU  118      3.370    6.411   45.788  1.00 00.00
ATOM    844  N    SER  119      0.741   10.161   44.667  1.00 00.00
ATOM    845  CA   SER  119     -0.177   11.062   43.926  1.00 00.00
ATOM    846  C    SER  119     -1.286   10.258   43.288  1.00 00.00
ATOM    847  O    SER  119     -1.211    9.011   43.223  1.00 00.00
ATOM    848  CB   SER  119      0.594   11.824   42.842  1.00 00.00
ATOM    849  OG   SER  119      0.973   10.942   41.794  1.00 00.00
ATOM    850  N    HIS  120     -2.331   10.935   42.811  1.00 00.00
ATOM    851  CA   HIS  120     -3.444   10.173   42.151  1.00 00.00
ATOM    852  C    HIS  120     -2.926    9.346   41.000  1.00 00.00
ATOM    853  O    HIS  120     -3.327    8.189   40.859  1.00 00.00
ATOM    854  CB   HIS  120     -4.504   11.080   41.583  1.00 00.00
ATOM    855  CG   HIS  120     -5.330   11.751   42.617  1.00 00.00
ATOM    856  CD2  HIS  120     -5.375   11.599   43.962  1.00 00.00
ATOM    857  ND1  HIS  120     -6.158   12.804   42.315  1.00 00.00
ATOM    858  CE1  HIS  120     -6.749   13.220   43.425  1.00 00.00
```

Fig. 2 cont.

```
ATOM    859  NE2 HIS   120      -6.258  12.538  44.438  1.00 00.00
ATOM    860  N   SER   121      -2.039   9.945  40.175  1.00 00.00
ATOM    861  CA  SER   121      -1.582   9.245  38.951  1.00 00.00
ATOM    862  C   SER   121      -0.691   8.086  39.330  1.00 00.00
ATOM    863  O   SER   121      -0.773   7.037  38.709  1.00 00.00
ATOM    864  CB  SER   121      -0.856  10.153  37.927  1.00 00.00
ATOM    865  OG  SER   121       0.375  10.701  38.393  1.00 00.00
ATOM    866  N   GLN   122       0.150   8.271  40.350  1.00 00.00
ATOM    867  CA  GLN   122       1.015   7.161  40.807  1.00 00.00
ATOM    868  C   GLN   122       0.158   6.028  41.369  1.00 00.00
ATOM    869  O   GLN   122       0.494   4.837  41.200  1.00 00.00
ATOM    870  CB  GLN   122       2.020   7.611  41.873  1.00 00.00
ATOM    871  CG  GLN   122       3.071   8.614  41.369  1.00 00.00
ATOM    872  CD  GLN   122       3.696   9.432  42.498  1.00 00.00
ATOM    873  NE2 GLN   122       4.653  10.281  42.138  1.00 00.00
ATOM    874  OE1 GLN   122       3.295   9.331  43.690  1.00 00.00
ATOM    875  N   MET   123      -0.910   6.384  42.073  1.00 00.00
ATOM    876  CA  MET   123      -1.759   5.362  42.691  1.00 00.00
ATOM    877  C   MET   123      -2.479   4.574  41.615  1.00 00.00
ATOM    878  O   MET   123      -2.607   3.349  41.714  1.00 00.00
ATOM    879  CB  MET   123      -2.773   5.986  43.688  1.00 00.00
ATOM    880  CG  MET   123      -3.650   4.950  44.419  1.00 00.00
ATOM    881  SD  MET   123      -2.692   3.829  45.458  1.00 00.00
ATOM    882  CE  MET   123      -2.339   4.922  46.861  1.00 00.00
ATOM    883  N   VAL   124      -2.959   5.278  40.592  1.00 00.00
ATOM    884  CA  VAL   124      -3.713   4.617  39.515  1.00 00.00
ATOM    885  C   VAL   124      -2.747   3.636  38.799  1.00 00.00
ATOM    886  O   VAL   124      -3.122   2.494  38.467  1.00 00.00
ATOM    887  CB  VAL   124      -4.338   5.631  38.561  1.00 00.00
ATOM    888  CG1 VAL   124      -4.872   4.934  37.257  1.00 00.00
ATOM    889  CG2 VAL   124      -5.528   6.419  39.304  1.00 00.00
ATOM    890  N   ALA   125      -1.525   4.091  38.573  1.00 00.00
ATOM    891  CA  ALA   125      -0.513   3.258  37.897  1.00 00.00
ATOM    892  C   ALA   125      -0.150   2.044  38.720  1.00 00.00
ATOM    893  O   ALA   125      -0.018   0.959  38.154  1.00 00.00
ATOM    894  CB  ALA   125       0.786   4.062  37.502  1.00 00.00
ATOM    895  N   TRP   126       0.013   2.241  40.049  1.00 00.00
ATOM    896  CA  TRP   126       0.233   1.128  40.963  1.00 00.00
ATOM    897  C   TRP   126      -0.853   0.047  40.829  1.00 00.00
ATOM    898  O   TRP   126      -0.561  -1.150  40.697  1.00 00.00
ATOM    899  CB  TRP   126       0.292   1.641  42.410  1.00 00.00
ATOM    900  CG  TRP   126       0.845   0.615  43.336  1.00 00.00
ATOM    901  CD1 TRP   126       2.154   0.484  43.747  1.00 00.00
ATOM    902  CD2 TRP   126       0.118  -0.456  43.959  1.00 00.00
ATOM    903  CE2 TRP   126       1.035  -1.162  44.778  1.00 00.00
ATOM    904  CE3 TRP   126      -1.226  -0.849  43.947  1.00 00.00
ATOM    905  NE1 TRP   126       2.268  -0.588  44.594  1.00 00.00
ATOM    906  CZ2 TRP   126       0.672  -2.311  45.529  1.00 00.00
ATOM    907  CZ3 TRP   126      -1.618  -1.963  44.709  1.00 00.00
ATOM    908  CH2 TRP   126      -0.639  -2.714  45.481  1.00 00.00
ATOM    909  N   ILE   127      -2.124   0.459  40.868  1.00 00.00
ATOM    910  CA  ILE   127      -3.237  -0.495  40.898  1.00 00.00
ATOM    911  C   ILE   127      -3.325  -1.184  39.508  1.00 00.00
ATOM    912  O   ILE   127      -3.541  -2.396  39.405  1.00 00.00
ATOM    913  CB  ILE   127      -4.553   0.215  41.232  1.00 00.00
ATOM    914  CG1 ILE   127      -4.488   0.861  42.629  1.00 00.00
ATOM    915  CG2 ILE   127      -5.756  -0.762  41.130  1.00 00.00
ATOM    916  CD1 ILE   127      -5.636   1.884  42.913  1.00 00.00
ATOM    917  N   HIS   128      -3.097  -0.419  38.451  1.00 00.00
ATOM    918  CA  HIS   128      -3.016  -1.044  37.125  1.00 00.00
ATOM    919  C   HIS   128      -1.948  -2.128  37.065  1.00 00.00
ATOM    920  O   HIS   128      -2.182  -3.212  36.511  1.00 00.00
ATOM    921  CB  HIS   128      -2.797   0.005  36.024  1.00 00.00
ATOM    922  CG  HIS   128      -4.088   0.522  35.431  1.00 00.00
ATOM    923  CD2 HIS   128      -5.166  -0.137  34.932  1.00 00.00
ATOM    924  ND1 HIS   128      -4.378   1.871  35.311  1.00 00.00
ATOM    925  CE1 HIS   128      -5.563   2.022  34.735  1.00 00.00
ATOM    926  NE2 HIS   128      -6.080   0.820  34.531  1.00 00.00
ATOM    927  N   ASP   129      -0.780  -1.824  37.616  1.00 00.00
ATOM    928  CA  ASP   129       0.335  -2.775  37.612  1.00 00.00
ATOM    929  C   ASP   129       0.018  -4.039  38.352  1.00 00.00
ATOM    930  O   ASP   129       0.404  -5.108  37.893  1.00 00.00
```

Fig. 2 cont.

```
ATOM    931  CB   ASP  129    1.561  -2.142  38.198  1.00 00.00
ATOM    932  CG   ASP  129    2.239  -1.173  37.236  1.00 00.00
ATOM    933  OD1  ASP  129    1.857  -1.116  36.033  1.00 00.00
ATOM    934  OD2  ASP  129    3.198  -0.506  37.682  1.00 00.00
ATOM    935  N    PHE  130   -0.681  -3.920  39.492  1.00 00.00
ATOM    936  CA   PHE  130   -1.090  -5.087  40.285  1.00 00.00
ATOM    937  C    PHE  130   -2.066  -5.934  39.468  1.00 00.00
ATOM    938  O    PHE  130   -1.857  -7.151  39.267  1.00 00.00
ATOM    939  CB   PHE  130   -1.705  -4.638  41.632  1.00 00.00
ATOM    940  CG   PHE  130   -2.005  -5.781  42.569  1.00 00.00
ATOM    941  CD1  PHE  130   -3.179  -6.528  42.404  1.00 00.00
ATOM    942  CD2  PHE  130   -1.152  -6.077  43.623  1.00 00.00
ATOM    943  CE1  PHE  130   -3.480  -7.599  43.221  1.00 00.00
ATOM    944  CE2  PHE  130   -1.438  -7.149  44.508  1.00 00.00
ATOM    945  CZ   PHE  130   -2.595  -7.925  44.301  1.00 00.00
ATOM    946  N    VAL  131   -3.118  -5.284  38.992  1.00 00.00
ATOM    947  CA   VAL  131   -4.237  -5.925  38.351  1.00 00.00
ATOM    948  C    VAL  131   -3.780  -6.646  37.044  1.00 00.00
ATOM    949  O    VAL  131   -4.170  -7.803  36.787  1.00 00.00
ATOM    950  CB   VAL  131   -5.298  -4.817  38.169  1.00 00.00
ATOM    951  CG1  VAL  131   -6.164  -4.974  37.000  1.00 00.00
ATOM    952  CG2  VAL  131   -6.041  -4.548  39.539  1.00 00.00
ATOM    953  N    ASN  132   -2.892  -5.992  36.294  1.00 00.00
ATOM    954  CA   ASN  132   -2.357  -6.543  35.053  1.00 00.00
ATOM    955  C    ASN  132   -1.519  -7.774  35.325  1.00 00.00
ATOM    956  O    ASN  132   -1.675  -8.801  34.625  1.00 00.00
ATOM    957  CB   ASN  132   -1.538  -5.491  34.239  1.00 00.00
ATOM    958  CG   ASN  132   -2.428  -4.374  33.703  1.00 00.00
ATOM    959  ND2  ASN  132   -1.879  -3.200  33.551  1.00 00.00
ATOM    960  OD1  ASN  132   -3.613  -4.571  33.515  1.00 00.00
ATOM    961  N    GLU  133   -0.628  -7.676  36.304  1.00 00.00
ATOM    962  CA   GLU  133    0.144  -8.846  36.708  1.00 00.00
ATOM    963  C    GLU  133   -0.750 -10.001  37.134  1.00 00.00
ATOM    964  O    GLU  133   -0.515 -11.154  36.722  1.00 00.00
ATOM    965  CB   GLU  133    1.220  -8.515  37.759  1.00 00.00
ATOM    966  CG   GLU  133    1.998  -9.775  38.255  1.00 00.00
ATOM    967  CD   GLU  133    2.833 -10.502  37.131  1.00 00.00
ATOM    968  OE1  GLU  133    3.495  -9.812  36.378  1.00 00.00
ATOM    969  OE2  GLU  133    2.851 -11.765  37.035  1.00 00.00
ATOM    970  N    TYR  134   -1.764  -9.729  37.959  1.00 00.00
ATOM    971  CA   TYR  134   -2.663 -10.791  38.382  1.00 00.00
ATOM    972  C    TYR  134   -3.339 -11.476  37.187  1.00 00.00
ATOM    973  O    TYR  134   -3.410 -12.727  37.131  1.00 00.00
ATOM    974  CB   TYR  134   -3.708 -10.304  39.388  1.00 00.00
ATOM    975  CG   TYR  134   -4.438 -11.440  40.061  1.00 00.00
ATOM    976  CD1  TYR  134   -3.936 -12.012  41.247  1.00 00.00
ATOM    977  CD2  TYR  134   -5.597 -11.982  39.501  1.00 00.00
ATOM    978  CE1  TYR  134   -4.601 -13.101  41.875  1.00 00.00
ATOM    979  CE2  TYR  134   -6.275 -13.064  40.132  1.00 00.00
ATOM    980  CZ   TYR  134   -5.760 -13.612  41.319  1.00 00.00
ATOM    981  OH   TYR  134   -6.428 -14.664  41.933  1.00 00.00
ATOM    982  N    HIS  135   -3.805 -10.672  36.235  1.00 00.00
ATOM    983  CA   HIS  135   -4.515 -11.218  35.074  1.00 00.00
ATOM    984  C    HIS  135   -3.585 -12.041  34.155  1.00 00.00
ATOM    985  O    HIS  135   -3.994 -13.101  33.627  1.00 00.00
ATOM    986  CB   HIS  135   -5.197 -10.090  34.302  1.00 00.00
ATOM    987  CG   HIS  135   -5.889 -10.539  33.041  1.00 00.00
ATOM    988  CD2  HIS  135   -5.527 -10.418  31.741  1.00 00.00
ATOM    989  ND1  HIS  135   -7.136 -11.130  33.034  1.00 00.00
ATOM    990  CE1  HIS  135   -7.481 -11.421  31.789  1.00 00.00
ATOM    991  NE2  HIS  135   -6.523 -10.991  30.986  1.00 00.00
ATOM    992  N    HIS  136   -2.370 -11.553  33.921  1.00 00.00
ATOM    993  CA   HIS  136   -1.386 -12.327  33.151  1.00 00.00
ATOM    994  C    HIS  136   -1.129 -13.711  33.749  1.00 00.00
ATOM    995  O    HIS  136   -0.833 -14.676  33.020  1.00 00.00
ATOM    996  CB   HIS  136   -0.045 -11.592  33.037  1.00 00.00
ATOM    997  CG   HIS  136   -0.096 -10.401  32.141  1.00 00.00
ATOM    998  CD2  HIS  136    0.367  -9.136  32.309  1.00 00.00
ATOM    999  ND1  HIS  136   -0.671 -10.443  30.880  1.00 00.00
ATOM   1000  CE1  HIS  136   -0.561  -9.249  30.316  1.00 00.00
ATOM   1001  NE2  HIS  136    0.065  -8.440  31.161  1.00 00.00
ATOM   1002  N    ALA  137   -1.262 -13.817  35.066  1.00 00.00
```

Fig. 2 cont.

```
ATOM   1003  CA   ALA   137    -0.791  -14.974   35.765  1.00 00.00
ATOM   1004  C    ALA   137    -1.848  -16.016   35.841  1.00 00.00
ATOM   1005  O    ALA   137    -1.540  -17.208   35.858  1.00 00.00
ATOM   1006  CB   ALA   137    -0.347  -14.574   37.153  1.00 00.00
ATOM   1007  N    THR   138    -3.103  -15.582   35.860  1.00 00.00
ATOM   1008  CA   THR   138    -4.224  -16.451   36.223  1.00 00.00
ATOM   1009  C    THR   138    -5.320  -16.532   35.151  1.00 00.00
ATOM   1010  O    THR   138    -6.151  -17.419   35.233  1.00 00.00
ATOM   1011  CB   THR   138    -4.945  -15.975   37.511  1.00 00.00
ATOM   1012  CG2  THR   138    -3.993  -15.844   38.625  1.00 00.00
ATOM   1013  OG1  THR   138    -5.571  -14.708   37.280  1.00 00.00
ATOM   1014  N    SER   139    -5.314  -15.598   34.191  1.00 00.00
ATOM   1015  CA   SER   139    -6.423  -15.466   33.217  1.00 00.00
ATOM   1016  C    SER   139    -7.617  -14.669   33.781  1.00 00.00
ATOM   1017  O    SER   139    -8.578  -14.337   33.046  1.00 00.00
ATOM   1018  CB   SER   139    -6.898  -16.842   32.684  1.00 00.00
ATOM   1019  OG   SER   139    -7.930  -17.428   33.487  1.00 00.00
ATOM   1020  N    ARG   140    -7.579  -14.363   35.091  1.00 00.00
ATOM   1021  CA   ARG   140    -8.681  -13.646   35.714  1.00 00.00
ATOM   1022  C    ARG   140    -8.274  -12.225   36.112  1.00 00.00
ATOM   1023  O    ARG   140    -7.155  -11.976   36.542  1.00 00.00
ATOM   1024  CB   ARG   140    -9.207  -14.397   36.964  1.00 00.00
ATOM   1025  CG   ARG   140    -9.684  -15.809   36.662  1.00 00.00
ATOM   1026  CD   ARG   140   -10.889  -15.778   35.727  1.00 00.00
ATOM   1027  NE   ARG   140   -11.969  -14.964   36.286  1.00 00.00
ATOM   1028  CZ   ARG   140   -12.834  -15.363   37.212  1.00 00.00
ATOM   1029  NH1  ARG   140   -12.782  -16.599   37.710  1.00 00.00
ATOM   1030  NH2  ARG   140   -13.770  -14.522   37.626  1.00 00.00
ATOM   1031  N    TRP   141    -9.202  -11.292   35.956  1.00 00.00
ATOM   1032  CA   TRP   141    -9.028   -9.966   36.559  1.00 00.00
ATOM   1033  C    TRP   141    -9.365  -10.127   38.062  1.00 00.00
ATOM   1034  O    TRP   141   -10.441  -10.663   38.395  1.00 00.00
ATOM   1035  CB   TRP   141   -10.001   -8.977   35.891  1.00 00.00
ATOM   1036  CG   TRP   141    -9.650   -8.734   34.442  1.00 00.00
ATOM   1037  CD1  TRP   141   -10.284   -9.259   33.327  1.00 00.00
ATOM   1038  CD2  TRP   141    -8.513   -8.002   33.955  1.00 00.00
ATOM   1039  CE2  TRP   141    -8.529   -8.086   32.535  1.00 00.00
ATOM   1040  CE3  TRP   141    -7.497   -7.262   34.576  1.00 00.00
ATOM   1041  NE1  TRP   141    -9.620   -8.853   32.177  1.00 00.00
ATOM   1042  CZ2  TRP   141    -7.548   -7.479   31.742  1.00 00.00
ATOM   1043  CZ3  TRP   141    -6.530   -6.646   33.790  1.00 00.00
ATOM   1044  CH2  TRP   141    -6.565   -6.753   32.376  1.00 00.00
ATOM   1045  N    PRO   142    -8.498   -9.572   38.964  1.00 00.00
ATOM   1046  CA   PRO   142    -8.759   -9.663   40.407  1.00 00.00
ATOM   1047  C    PRO   142    -9.899   -8.766   40.791  1.00 00.00
ATOM   1048  O    PRO   142   -10.240   -7.838   40.049  1.00 00.00
ATOM   1049  CB   PRO   142    -7.489   -9.117   41.034  1.00 00.00
ATOM   1050  CG   PRO   142    -6.888   -8.135   39.964  1.00 00.00
ATOM   1051  CD   PRO   142    -7.335   -8.708   38.632  1.00 00.00
ATOM   1052  N    MET   143   -10.516   -9.055   41.924  1.00 00.00
ATOM   1053  CA   MET   143   -11.486   -8.155   42.471  1.00 00.00
ATOM   1054  C    MET   143   -10.758   -6.984   43.145  1.00 00.00
ATOM   1055  O    MET   143    -9.597   -7.107   43.512  1.00 00.00
ATOM   1056  CB   MET   143   -12.450   -8.897   43.410  1.00 00.00
ATOM   1057  CG   MET   143   -12.951  -10.252   42.850  1.00 00.00
ATOM   1058  SD   MET   143   -14.392  -10.777   43.781  1.00 00.00
ATOM   1059  CE   MET   143   -13.590  -11.250   45.327  1.00 00.00
ATOM   1060  N    ILE   144   -11.398   -5.805   43.141  1.00 00.00
ATOM   1061  CA   ILE   144   -10.898   -4.665   43.868  1.00 00.00
ATOM   1062  C    ILE   144   -11.837   -4.304   45.011  1.00 00.00
ATOM   1063  O    ILE   144   -13.036   -4.007   44.806  1.00 00.00
ATOM   1064  CB   ILE   144   -10.708   -3.401   42.957  1.00 00.00
ATOM   1065  CG1  ILE   144    -9.616   -3.648   41.922  1.00 00.00
ATOM   1066  CG2  ILE   144   -10.399   -2.163   43.813  1.00 00.00
ATOM   1067  CD1  ILE   144    -9.571   -2.560   40.834  1.00 00.00
ATOM   1068  N    TYR   145   -11.252   -4.291   46.220  1.00 00.00
ATOM   1069  CA   TYR   145   -11.981   -3.929   47.450  1.00 00.00
ATOM   1070  C    TYR   145   -11.568   -2.522   47.848  1.00 00.00
ATOM   1071  O    TYR   145   -10.345   -2.189   47.939  1.00 00.00
ATOM   1072  CB   TYR   145   -11.655   -4.939   48.575  1.00 00.00
ATOM   1073  CG   TYR   145   -12.115   -4.526   49.956  1.00 00.00
ATOM   1074  CD1  TYR   145   -11.298   -3.767   50.789  1.00 00.00
```

Fig. 2 cont.

```
ATOM   1075  CD2 TYR  145     -13.361  -4.886  50.427  1.00 00.00
ATOM   1076  CE1 TYR  145     -11.724  -3.361  52.038  1.00 00.00
ATOM   1077  CE2 TYR  145     -13.790  -4.505  51.684  1.00 00.00
ATOM   1078  CZ  TYR  145     -12.983  -3.751  52.484  1.00 00.00
ATOM   1079  OH  TYR  145     -13.458  -3.351  53.749  1.00 00.00
ATOM   1080  N   THR  146     -12.588  -1.680  48.023  1.00 00.00
ATOM   1081  CA  THR  146     -12.350  -0.284  48.446  1.00 00.00
ATOM   1082  C   THR  146     -13.618   0.341  49.041  1.00 00.00
ATOM   1083  O   THR  146     -14.622  -0.338  49.163  1.00 00.00
ATOM   1084  CB  THR  146     -11.748   0.550  47.244  1.00 00.00
ATOM   1085  CG2 THR  146     -12.794   0.894  46.154  1.00 00.00
ATOM   1086  OG1 THR  146     -11.094   1.714  47.747  1.00 00.00
ATOM   1087  N   THR  147     -13.557   1.626  49.401  1.00 00.00
ATOM   1088  CA  THR  147     -14.731   2.441  49.615  1.00 00.00
ATOM   1089  C   THR  147     -14.831   3.511  48.513  1.00 00.00
ATOM   1090  O   THR  147     -13.841   3.897  47.951  1.00 00.00
ATOM   1091  CB  THR  147     -14.723   3.180  50.999  1.00 00.00
ATOM   1092  CG2 THR  147     -14.532   2.168  52.120  1.00 00.00
ATOM   1093  OG1 THR  147     -13.641   4.129  51.041  1.00 00.00
ATOM   1094  N   ALA  148     -16.046   4.029  48.278  1.00 00.00
ATOM   1095  CA  ALA  148     -16.213   5.140  47.346  1.00 00.00
ATOM   1096  C   ALA  148     -15.353   6.331  47.756  1.00 00.00
ATOM   1097  O   ALA  148     -14.723   6.988  46.911  1.00 00.00
ATOM   1098  CB  ALA  148     -17.661   5.544  47.285  1.00 00.00
ATOM   1099  N   ASP  149     -15.292   6.563  49.059  1.00 00.00
ATOM   1100  CA  ASP  149     -14.604   7.726  49.560  1.00 00.00
ATOM   1101  C   ASP  149     -13.108   7.589  49.381  1.00 00.00
ATOM   1102  O   ASP  149     -12.418   8.580  49.068  1.00 00.00
ATOM   1103  CB  ASP  149     -14.920   7.961  51.036  1.00 00.00
ATOM   1104  CG  ASP  149     -13.922   8.872  51.682  1.00 00.00
ATOM   1105  OD1 ASP  149     -14.120  10.093  51.567  1.00 00.00
ATOM   1106  OD2 ASP  149     -12.940   8.383  52.301  1.00 00.00
ATOM   1107  N   TRP  150     -12.588   6.398  49.635  1.00 00.00
ATOM   1108  CA  TRP  150     -11.140   6.212  49.434  1.00 00.00
ATOM   1109  C   TRP  150     -10.792   6.379  47.936  1.00 00.00
ATOM   1110  O   TRP  150      -9.809   7.049  47.585  1.00 00.00
ATOM   1111  CB  TRP  150     -10.646   4.873  49.968  1.00 00.00
ATOM   1112  CG  TRP  150      -9.148   4.764  49.927  1.00 00.00
ATOM   1113  CD1 TRP  150      -8.296   5.056  50.943  1.00 00.00
ATOM   1114  CD2 TRP  150      -8.302   4.385  48.795  1.00 00.00
ATOM   1115  CE2 TRP  150      -6.968   4.480  49.221  1.00 00.00
ATOM   1116  CE3 TRP  150      -8.555   3.987  47.481  1.00 00.00
ATOM   1117  NE1 TRP  150      -6.984   4.888  50.520  1.00 00.00
ATOM   1118  CZ2 TRP  150      -5.875   4.169  48.385  1.00 00.00
ATOM   1119  CZ3 TRP  150      -7.477   3.716  46.647  1.00 00.00
ATOM   1120  CH2 TRP  150      -6.157   3.787  47.113  1.00 00.00
ATOM   1121  N   TRP  151     -11.576   5.740  47.083  1.00 00.00
ATOM   1122  CA  TRP  151     -11.349   5.765  45.641  1.00 00.00
ATOM   1123  C   TRP  151     -11.352   7.207  45.138  1.00 00.00
ATOM   1124  O   TRP  151     -10.493   7.592  44.359  1.00 00.00
ATOM   1125  CB  TRP  151     -12.399   4.901  44.917  1.00 00.00
ATOM   1126  CG  TRP  151     -11.968   4.539  43.540  1.00 00.00
ATOM   1127  CD1 TRP  151     -12.355   5.158  42.361  1.00 00.00
ATOM   1128  CD2 TRP  151     -10.987   3.556  43.171  1.00 00.00
ATOM   1129  CE2 TRP  151     -10.858   3.604  41.751  1.00 00.00
ATOM   1130  CE3 TRP  151     -10.217   2.615  43.895  1.00 00.00
ATOM   1131  NE1 TRP  151     -11.706   4.579  41.292  1.00 00.00
ATOM   1132  CZ2 TRP  151      -9.974   2.760  41.046  1.00 00.00
ATOM   1133  CZ3 TRP  151      -9.374   1.772  43.207  1.00 00.00
ATOM   1134  CH2 TRP  151      -9.242   1.846  41.793  1.00 00.00
ATOM   1135  N   ASN  152     -12.304   7.998  45.625  1.00 00.00
ATOM   1136  CA  ASN  152     -12.378   9.408  45.268  1.00 00.00
ATOM   1137  C   ASN  152     -11.131  10.198  45.702  1.00 00.00
ATOM   1138  O   ASN  152     -10.576  10.975  44.936  1.00 00.00
ATOM   1139  CB  ASN  152     -13.644  10.016  45.868  1.00 00.00
ATOM   1140  CG  ASN  152     -13.910  11.421  45.342  1.00 00.00
ATOM   1141  ND2 ASN  152     -14.144  12.338  46.227  1.00 00.00
ATOM   1142  OD1 ASN  152     -13.907  11.654  44.125  1.00 00.00
ATOM   1143  N   ARG  153     -10.683   9.955  46.913  1.00 00.00
ATOM   1144  CA  ARG  153      -9.649  10.765  47.504  1.00 00.00
ATOM   1145  C   ARG  153      -8.244  10.402  46.974  1.00 00.00
ATOM   1146  O   ARG  153      -7.404  11.289  46.732  1.00 00.00
```

Fig. 2 cont.

```
ATOM   1147  CB   ARG  153      -9.708  10.587  49.009  1.00 00.00
ATOM   1148  CG   ARG  153     -10.777  11.443  49.780  1.00 00.00
ATOM   1149  CD   ARG  153     -11.929  12.069  48.948  1.00 00.00
ATOM   1150  NE   ARG  153     -13.235  11.471  49.221  1.00 00.00
ATOM   1151  CZ   ARG  153     -14.405  12.102  49.113  1.00 00.00
ATOM   1152  NH1  ARG  153     -14.464  13.420  48.839  1.00 00.00
ATOM   1153  NH2  ARG  153     -15.524  11.434  49.344  1.00 00.00
ATOM   1154  N    CYS  154      -7.992   9.103  46.788  1.00 00.00
ATOM   1155  CA   CYS  154      -6.641   8.625  46.496  1.00 00.00
ATOM   1156  C    CYS  154      -6.415   8.320  45.038  1.00 00.00
ATOM   1157  O    CYS  154      -5.276   8.121  44.623  1.00 00.00
ATOM   1158  CB   CYS  154      -6.320   7.371  47.344  1.00 00.00
ATOM   1159  SG   CYS  154      -6.252   7.752  49.136  1.00 00.00
ATOM   1160  N    THR  155      -7.481   8.211  44.268  1.00 00.00
ATOM   1161  CA   THR  155      -7.299   8.009  42.810  1.00 00.00
ATOM   1162  C    THR  155      -7.913   9.113  41.939  1.00 00.00
ATOM   1163  O    THR  155      -7.848   9.020  40.685  1.00 00.00
ATOM   1164  CB   THR  155      -7.857   6.675  42.298  1.00 00.00
ATOM   1165  CG2  THR  155      -7.453   5.490  43.184  1.00 00.00
ATOM   1166  OG1  THR  155      -9.290   6.731  42.183  1.00 00.00
ATOM   1167  N    GLY  156      -8.537  10.120  42.556  1.00 00.00
ATOM   1168  CA   GLY  156      -9.285  11.099  41.757  1.00 00.00
ATOM   1169  C    GLY  156     -10.542  10.489  41.165  1.00 00.00
ATOM   1170  O    GLY  156     -11.061  10.946  40.125  1.00 00.00
ATOM   1171  N    ASN  157     -11.048   9.455  41.816  1.00 00.00
ATOM   1172  CA   ASN  157     -12.220   8.735  41.339  1.00 00.00
ATOM   1173  C    ASN  157     -11.981   8.165  39.950  1.00 00.00
ATOM   1174  O    ASN  157     -12.846   8.239  39.052  1.00 00.00
ATOM   1175  CB   ASN  157     -13.516   9.596  41.390  1.00 00.00
ATOM   1176  CG   ASN  157     -14.778   8.748  41.386  1.00 00.00
ATOM   1177  ND2  ASN  157     -15.827   9.224  40.692  1.00 00.00
ATOM   1178  OD1  ASN  157     -14.812   7.659  41.969  1.00 00.00
ATOM   1179  N    ALA  158     -10.821   7.547  39.806  1.00 00.00
ATOM   1180  CA   ALA  158     -10.305   7.120  38.504  1.00 00.00
ATOM   1181  C    ALA  158     -11.257   6.128  37.815  1.00 00.00
ATOM   1182  O    ALA  158     -11.861   5.234  38.465  1.00 00.00
ATOM   1183  CB   ALA  158      -8.973   6.490  38.690  1.00 00.00
ATOM   1184  N    LYS  159     -11.412   6.290  36.510  1.00 00.00
ATOM   1185  CA   LYS  159     -12.200   5.332  35.751  1.00 00.00
ATOM   1186  C    LYS  159     -11.159   4.335  35.233  1.00 00.00
ATOM   1187  O    LYS  159      -9.976   4.432  35.607  1.00 00.00
ATOM   1188  CB   LYS  159     -12.987   6.082  34.655  1.00 00.00
ATOM   1189  CG   LYS  159     -13.958   7.132  35.259  1.00 00.00
ATOM   1190  CD   LYS  159     -14.720   7.980  34.207  1.00 00.00
ATOM   1191  CE   LYS  159     -16.009   8.541  34.809  1.00 00.00
ATOM   1192  NZ   LYS  159     -16.380   9.904  34.284  1.00 00.00
ATOM   1193  N    GLY  160     -11.557   3.362  34.426  1.00 00.00
ATOM   1194  CA   GLY  160     -10.574   2.494  33.755  1.00 00.00
ATOM   1195  C    GLY  160     -10.519   1.092  34.343  1.00 00.00
ATOM   1196  O    GLY  160      -9.809   0.219  33.815  1.00 00.00
ATOM   1197  N    PHE  161     -11.201   0.870  35.451  1.00 00.00
ATOM   1198  CA   PHE  161     -11.199  -0.461  36.057  1.00 00.00
ATOM   1199  C    PHE  161     -12.514  -1.187  36.009  1.00 00.00
ATOM   1200  O    PHE  161     -12.547  -2.407  36.179  1.00 00.00
ATOM   1201  CB   PHE  161     -10.695  -0.409  37.496  1.00 00.00
ATOM   1202  CG   PHE  161      -9.306   0.138  37.620  1.00 00.00
ATOM   1203  CD1  PHE  161      -8.218  -0.716  37.687  1.00 00.00
ATOM   1204  CD2  PHE  161      -9.084   1.522  37.672  1.00 00.00
ATOM   1205  CE1  PHE  161      -6.905  -0.184  37.840  1.00 00.00
ATOM   1206  CE2  PHE  161      -7.789   2.041  37.829  1.00 00.00
ATOM   1207  CZ   PHE  161      -6.716   1.175  37.888  1.00 00.00
ATOM   1208  N    GLY  162     -13.586  -0.441  35.778  1.00 00.00
ATOM   1209  CA   GLY  162     -14.914  -0.951  35.977  1.00 00.00
ATOM   1210  C    GLY  162     -15.354  -1.964  34.952  1.00 00.00
ATOM   1211  O    GLY  162     -16.343  -2.698  35.186  1.00 00.00
ATOM   1212  N    ASP  163     -14.680  -2.032  33.810  1.00 00.00
ATOM   1213  CA   ASP  163     -15.073  -3.106  32.891  1.00 00.00
ATOM   1214  C    ASP  163     -14.477  -4.423  33.256  1.00 00.00
ATOM   1215  O    ASP  163     -15.103  -5.446  32.991  1.00 00.00
ATOM   1216  CB   ASP  163     -14.835  -2.827  31.408  1.00 00.00
ATOM   1217  CG   ASP  163     -13.801  -1.759  31.161  1.00 00.00
ATOM   1218  OD1  ASP  163     -12.652  -1.847  31.719  1.00 00.00
```

Fig. 2 cont.

```
ATOM   1219  OD2 ASP   163     -14.171   -0.822   30.401  1.00 00.00
ATOM   1220  N   LYS   164     -13.283   -4.414   33.853  1.00 00.00
ATOM   1221  CA  LYS   164     -12.510   -5.665   34.037  1.00 00.00
ATOM   1222  C   LYS   164     -12.626   -6.263   35.473  1.00 00.00
ATOM   1223  O   LYS   164     -12.846   -7.480   35.658  1.00 00.00
ATOM   1224  CB  LYS   164     -11.041   -5.438   33.680  1.00 00.00
ATOM   1225  CG  LYS   164     -10.729   -5.388   32.158  1.00 00.00
ATOM   1226  CD  LYS   164      -9.504   -4.471   32.097  1.00 00.00
ATOM   1227  CE  LYS   164      -9.364   -2.957   32.067  1.00 00.00
ATOM   1228  NZ  LYS   164      -8.141   -2.527   31.336  1.00 00.00
ATOM   1229  N   CYS   165     -12.441   -5.424   36.481  1.00 00.00
ATOM   1230  CA  CYS   165     -12.260   -5.940   37.864  1.00 00.00
ATOM   1231  C   CYS   165     -13.560   -5.869   38.631  1.00 00.00
ATOM   1232  O   CYS   165     -14.127   -4.794   38.765  1.00 00.00
ATOM   1233  CB  CYS   165     -11.189   -5.150   38.589  1.00 00.00
ATOM   1234  SG  CYS   165      -9.612   -5.134   37.779  1.00 00.00
ATOM   1235  N   PRO   166     -14.053   -7.025   39.131  1.00 00.00
ATOM   1236  CA  PRO   166     -15.261   -6.969   39.965  1.00 00.00
ATOM   1237  C   PRO   166     -15.045   -6.055   41.199  1.00 00.00
ATOM   1238  O   PRO   166     -13.989   -6.109   41.833  1.00 00.00
ATOM   1239  CB  PRO   166     -15.444   -8.417   40.420  1.00 00.00
ATOM   1240  CG  PRO   166     -14.735   -9.252   39.352  1.00 00.00
ATOM   1241  CD  PRO   166     -13.553   -8.414   38.948  1.00 00.00
ATOM   1242  N   LEU   167     -16.024   -5.221   41.497  1.00 00.00
ATOM   1243  CA  LEU   167     -15.928   -4.289   42.638  1.00 00.00
ATOM   1244  C   LEU   167     -16.459   -4.946   43.895  1.00 00.00
ATOM   1245  O   LEU   167     -17.575   -5.466   43.891  1.00 00.00
ATOM   1246  CB  LEU   167     -16.724   -2.999   42.358  1.00 00.00
ATOM   1247  CG  LEU   167     -16.806   -1.922   43.472  1.00 00.00
ATOM   1248  CD1 LEU   167     -15.383   -1.405   43.860  1.00 00.00
ATOM   1249  CD2 LEU   167     -17.714   -0.753   43.035  1.00 00.00
ATOM   1250  N   VAL   168     -15.657   -4.903   44.949  1.00 00.00
ATOM   1251  CA  VAL   168     -16.071   -5.215   46.340  1.00 00.00
ATOM   1252  C   VAL   168     -16.140   -3.911   47.112  1.00 00.00
ATOM   1253  O   VAL   168     -15.145   -3.299   47.406  1.00 00.00
ATOM   1254  CB  VAL   168     -15.131   -6.240   47.000  1.00 00.00
ATOM   1255  CG1 VAL   168     -15.698   -6.691   48.372  1.00 00.00
ATOM   1256  CG2 VAL   168     -14.964   -7.447   46.077  1.00 00.00
ATOM   1257  N   LEU   169     -17.348   -3.456   47.375  1.00 00.00
ATOM   1258  CA  LEU   169     -17.596   -2.130   47.910  1.00 00.00
ATOM   1259  C   LEU   169     -17.975   -2.186   49.409  1.00 00.00
ATOM   1260  O   LEU   169     -19.016   -2.783   49.770  1.00 00.00
ATOM   1261  CB  LEU   169     -18.773   -1.541   47.126  1.00 00.00
ATOM   1262  CG  LEU   169     -18.960   -0.042   46.923  1.00 00.00
ATOM   1263  CD1 LEU   169     -20.001    0.209   45.810  1.00 00.00
ATOM   1264  CD2 LEU   169     -19.382    0.576   48.213  1.00 00.00
ATOM   1265  N   ALA   170     -17.169   -1.565   50.275  1.00 00.00
ATOM   1266  CA  ALA   170     -17.536   -1.487   51.696  1.00 00.00
ATOM   1267  C   ALA   170     -18.411   -0.255   51.921  1.00 00.00
ATOM   1268  O   ALA   170     -18.038    0.874   51.523  1.00 00.00
ATOM   1269  CB  ALA   170     -16.306   -1.460   52.594  1.00 00.00
ATOM   1270  N   ALA   171     -19.596   -0.484   52.510  1.00 00.00
ATOM   1271  CA  ALA   171     -20.454    0.579   53.002  1.00 00.00
ATOM   1272  C   ALA   171     -21.377   -0.051   54.027  1.00 00.00
ATOM   1273  O   ALA   171     -22.293   -0.827   53.689  1.00 00.00
ATOM   1274  CB  ALA   171     -21.271    1.221   51.883  1.00 00.00
ATOM   1275  N   TYR   172     -21.173    0.285   55.286  1.00 00.00
ATOM   1276  CA  TYR   172     -21.978   -0.382   56.313  1.00 00.00
ATOM   1277  C   TYR   172     -23.366    0.256   56.490  1.00 00.00
ATOM   1278  O   TYR   172     -23.511    1.448   56.903  1.00 00.00
ATOM   1279  CB  TYR   172     -21.202   -0.571   57.622  1.00 00.00
ATOM   1280  CG  TYR   172     -19.812   -1.173   57.451  1.00 00.00
ATOM   1281  CD1 TYR   172     -19.499   -1.992   56.344  1.00 00.00
ATOM   1282  CD2 TYR   172     -18.804   -0.899   58.355  1.00 00.00
ATOM   1283  CE1 TYR   172     -18.231   -2.491   56.162  1.00 00.00
ATOM   1284  CE2 TYR   172     -17.542   -1.372   58.179  1.00 00.00
ATOM   1285  CZ  TYR   172     -17.254   -2.186   57.081  1.00 00.00
ATOM   1286  OH  TYR   172     -15.990   -2.688   56.917  1.00 00.00
ATOM   1287  N   SER   173     -24.394   -0.544   56.213  1.00 00.00
ATOM   1288  CA  SER   173     -25.739   -0.024   56.085  1.00 00.00
ATOM   1289  C   SER   173     -26.715   -1.171   55.961  1.00 00.00
ATOM   1290  O   SER   173     -26.320   -2.317   55.715  1.00 00.00
```

Fig. 2 cont.

```
ATOM  1291  CB   SER  173    -25.837   0.856  54.848  1.00  00.00
ATOM  1292  OG   SER  173    -27.134   1.433  54.740  1.00  00.00
ATOM  1293  N    SER  174    -28.002  -0.869  56.103  1.00  00.00
ATOM  1294  CA   SER  174    -29.001  -1.912  55.986  1.00  00.00
ATOM  1295  C    SER  174    -29.446  -1.988  54.559  1.00  00.00
ATOM  1296  O    SER  174    -30.112  -2.937  54.167  1.00  00.00
ATOM  1297  CB   SER  174    -30.178  -1.611  56.908  1.00  00.00
ATOM  1298  OG   SER  174    -29.712  -1.673  58.263  1.00  00.00
ATOM  1299  N    SER  175    -29.053  -0.992  53.769  1.00  00.00
ATOM  1300  CA   SER  175    -29.371  -0.997  52.343  1.00  00.00
ATOM  1301  C    SER  175    -28.059  -0.860  51.570  1.00  00.00
ATOM  1302  O    SER  175    -27.145  -0.260  52.061  1.00  00.00
ATOM  1303  CB   SER  175    -30.287   0.172  52.004  1.00  00.00
ATOM  1304  OG   SER  175    -29.704   1.424  52.400  1.00  00.00
ATOM  1305  N    PRO  176    -28.006  -1.403  50.334  1.00  00.00
ATOM  1306  CA   PRO  176    -26.745  -1.430  49.558  1.00  00.00
ATOM  1307  C    PRO  176    -26.202  -0.014  49.247  1.00  00.00
ATOM  1308  O    PRO  176    -26.955   0.962  49.291  1.00  00.00
ATOM  1309  CB   PRO  176    -27.139  -2.124  48.252  1.00  00.00
ATOM  1310  CG   PRO  176    -28.470  -2.834  48.557  1.00  00.00
ATOM  1311  CD   PRO  176    -29.127  -2.084  49.649  1.00  00.00
ATOM  1312  N    PRO  177    -24.903   0.082  48.902  1.00  00.00
ATOM  1313  CA   PRO  177    -24.157   1.330  48.658  1.00  00.00
ATOM  1314  C    PRO  177    -24.900   2.339  47.735  1.00  00.00
ATOM  1315  O    PRO  177    -25.480   1.967  46.690  1.00  00.00
ATOM  1316  CB   PRO  177    -22.888   0.814  47.942  1.00  00.00
ATOM  1317  CG   PRO  177    -22.697  -0.556  48.557  1.00  00.00
ATOM  1318  CD   PRO  177    -24.078  -1.104  48.574  1.00  00.00
ATOM  1319  N    LYS  178    -24.891   3.595  48.148  1.00  00.00
ATOM  1320  CA   LYS  178    -25.573   4.649  47.419  1.00  00.00
ATOM  1321  C    LYS  178    -24.653   5.290  46.405  1.00  00.00
ATOM  1322  O    LYS  178    -25.134   5.928  45.487  1.00  00.00
ATOM  1323  CB   LYS  178    -26.069   5.743  48.389  1.00  00.00
ATOM  1324  CG   LYS  178    -26.618   5.225  49.695  1.00  00.00
ATOM  1325  CD   LYS  178    -27.959   4.549  49.492  1.00  00.00
ATOM  1326  CE   LYS  178    -28.556   3.995  50.793  1.00  00.00
ATOM  1327  NZ   LYS  178    -27.740   2.925  51.511  1.00  00.00
ATOM  1328  N    THR  179    -23.339   5.177  46.577  1.00  00.00
ATOM  1329  CA   THR  179    -22.419   5.766  45.591  1.00  00.00
ATOM  1330  C    THR  179    -21.452   4.720  45.035  1.00  00.00
ATOM  1331  O    THR  179    -20.762   4.036  45.785  1.00  00.00
ATOM  1332  CB   THR  179    -21.601   6.926  46.192  1.00  00.00
ATOM  1333  CG2  THR  179    -22.490   7.896  46.888  1.00  00.00
ATOM  1334  OG1  THR  179    -20.749   6.382  47.179  1.00  00.00
ATOM  1335  N    ILE  180    -21.401   4.614  43.724  1.00  00.00
ATOM  1336  CA   ILE  180    -20.536   3.637  43.061  1.00  00.00
ATOM  1337  C    ILE  180    -19.348   4.393  42.468  1.00  00.00
ATOM  1338  O    ILE  180    -19.544   5.361  41.705  1.00  00.00
ATOM  1339  CB   ILE  180    -21.287   2.900  41.938  1.00  00.00
ATOM  1340  CG1  ILE  180    -22.650   2.368  42.457  1.00  00.00
ATOM  1341  CG2  ILE  180    -20.401   1.820  41.320  1.00  00.00
ATOM  1342  CD1  ILE  180    -22.541   1.396  43.695  1.00  00.00
ATOM  1343  N    PRO  181    -18.116   4.007  42.849  1.00  00.00
ATOM  1344  CA   PRO  181    -16.982   4.794  42.389  1.00  00.00
ATOM  1345  C    PRO  181    -16.589   4.492  40.952  1.00  00.00
ATOM  1346  O    PRO  181    -17.085   3.529  40.360  1.00  00.00
ATOM  1347  CB   PRO  181    -15.865   4.367  43.347  1.00  00.00
ATOM  1348  CG   PRO  181    -16.188   2.941  43.680  1.00  00.00
ATOM  1349  CD   PRO  181    -17.710   2.920  43.770  1.00  00.00
ATOM  1350  N    GLY  182    -15.702   5.310  40.409  1.00  00.00
ATOM  1351  CA   GLY  182    -15.038   5.016  39.141  1.00  00.00
ATOM  1352  C    GLY  182    -16.021   4.885  37.985  1.00  00.00
ATOM  1353  O    GLY  182    -17.012   5.608  37.915  1.00  00.00
ATOM  1354  N    ASP  183    -15.742   3.936  37.109  1.00  00.00
ATOM  1355  CA   ASP  183    -16.678   3.635  36.044  1.00  00.00
ATOM  1356  C    ASP  183    -17.350   2.285  36.232  1.00  00.00
ATOM  1357  O    ASP  183    -17.806   1.693  35.255  1.00  00.00
ATOM  1358  CB   ASP  183    -16.045   3.775  34.647  1.00  00.00
ATOM  1359  CG   ASP  183    -14.836   2.871  34.446  1.00  00.00
ATOM  1360  OD1  ASP  183    -14.533   2.029  35.302  1.00  00.00
ATOM  1361  OD2  ASP  183    -14.186   3.007  33.410  1.00  00.00
```

Fig. 2 cont.

```
ATOM   1362  N    TRP   184     -17.430    1.802   37.484  1.00 00.00
ATOM   1363  CA   TRP   184     -18.202    0.571   37.743  1.00 00.00
ATOM   1364  C    TRP   184     -19.693    0.849   37.597  1.00 00.00
ATOM   1365  O    TRP   184     -20.163    1.896   38.014  1.00 00.00
ATOM   1366  CB   TRP   184     -17.941    0.040   39.168  1.00 00.00
ATOM   1367  CG   TRP   184     -16.637   -0.734   39.299  1.00 00.00
ATOM   1368  CD1  TRP   184     -16.399   -2.048   38.932  1.00 00.00
ATOM   1369  CD2  TRP   184     -15.392   -0.217   39.806  1.00 00.00
ATOM   1370  CE2  TRP   184     -14.430   -1.264   39.721  1.00 00.00
ATOM   1371  CE3  TRP   184     -14.991    1.039   40.301  1.00 00.00
ATOM   1372  NE1  TRP   184     -15.058   -2.370   39.196  1.00 00.00
ATOM   1373  CZ2  TRP   184     -13.114   -1.103   40.157  1.00 00.00
ATOM   1374  CZ3  TRP   184     -13.670    1.199   40.758  1.00 00.00
ATOM   1375  CH2  TRP   184     -12.747    0.127   40.666  1.00 00.00
ATOM   1376  N    LYS   185     -20.436   -0.076   36.983  1.00 00.00
ATOM   1377  CA   LYS   185     -21.914    0.065   36.925  1.00 00.00
ATOM   1378  C    LYS   185     -22.498   -0.178   38.324  1.00 00.00
ATOM   1379  O    LYS   185     -23.378    0.541   38.777  1.00 00.00
ATOM   1380  CB   LYS   185     -22.550   -0.915   35.908  1.00 00.00
ATOM   1381  CG   LYS   185     -24.118   -0.787   35.828  1.00 00.00
ATOM   1382  CD   LYS   185     -24.783   -1.957   35.098  1.00 00.00
ATOM   1383  CE   LYS   185     -25.319   -3.025   36.094  1.00 00.00
ATOM   1384  NZ   LYS   185     -25.856   -4.266   35.403  1.00 00.00
ATOM   1385  N    THR   186     -21.951   -1.160   39.038  1.00 00.00
ATOM   1386  CA   THR   186     -22.456   -1.508   40.352  1.00 00.00
ATOM   1387  C    THR   186     -21.407   -2.422   41.001  1.00 00.00
ATOM   1388  O    THR   186     -20.359   -2.675   40.400  1.00 00.00
ATOM   1389  CB   THR   186     -23.828   -2.210   40.215  1.00 00.00
ATOM   1390  CG2  THR   186     -23.642   -3.600   39.514  1.00 00.00
ATOM   1391  OG1  THR   186     -24.433   -2.354   41.507  1.00 00.00
ATOM   1392  N    TRP   187     -21.655   -2.789   42.256  1.00 00.00
ATOM   1393  CA   TRP   187     -20.814   -3.702   43.049  1.00 00.00
ATOM   1394  C    TRP   187     -21.107   -5.131   42.634  1.00 00.00
ATOM   1395  O    TRP   187     -22.266   -5.459   42.254  1.00 00.00
ATOM   1396  CB   TRP   187     -21.090   -3.504   44.567  1.00 00.00
ATOM   1397  CG   TRP   187     -22.581   -3.418   44.937  1.00 00.00
ATOM   1398  CD1  TRP   187     -23.396   -2.306   44.881  1.00 00.00
ATOM   1399  CD2  TRP   187     -23.388   -4.486   45.442  1.00 00.00
ATOM   1400  CE2  TRP   187     -24.687   -3.979   45.648  1.00 00.00
ATOM   1401  CE3  TRP   187     -23.130   -5.830   45.752  1.00 00.00
ATOM   1402  NE1  TRP   187     -24.680   -2.651   45.300  1.00 00.00
ATOM   1403  CZ2  TRP   187     -25.730   -4.777   46.148  1.00 00.00
ATOM   1404  CZ3  TRP   187     -24.189   -6.637   46.216  1.00 00.00
ATOM   1405  CH2  TRP   187     -25.449   -6.105   46.430  1.00 00.00
ATOM   1406  N    THR   188     -20.068   -5.966   42.660  1.00 00.00
ATOM   1407  CA   THR   188     -20.211   -7.401   42.589  1.00 00.00
ATOM   1408  C    THR   188     -20.444   -8.002   44.007  1.00 00.00
ATOM   1409  O    THR   188     -21.309   -8.876   44.216  1.00 00.00
ATOM   1410  CB   THR   188     -18.975   -7.981   41.919  1.00 00.00
ATOM   1411  CG2  THR   188     -18.987   -9.531   41.945  1.00 00.00
ATOM   1412  OG1  THR   188     -18.938   -7.524   40.561  1.00 00.00
ATOM   1413  N    ILE   189     -19.672   -7.524   44.978  1.00 00.00
ATOM   1414  CA   ILE   189     -19.842   -7.917   46.372  1.00 00.00
ATOM   1415  C    ILE   189     -19.883   -6.664   47.199  1.00 00.00
ATOM   1416  O    ILE   189     -19.168   -5.711   46.927  1.00 00.00
ATOM   1417  CB   ILE   189     -18.693   -8.839   46.877  1.00 00.00
ATOM   1418  CG1  ILE   189     -18.743  -10.202   46.156  1.00 00.00
ATOM   1419  CG2  ILE   189     -18.792   -9.021   48.438  1.00 00.00
ATOM   1420  CD1  ILE   189     -17.461  -10.988   46.243  1.00 00.00
ATOM   1421  N    TRP   190     -20.745   -6.671   48.201  1.00 00.00
ATOM   1422  CA   TRP   190     -20.997   -5.491   49.059  1.00 00.00
ATOM   1423  C    TRP   190     -20.601   -5.891   50.461  1.00 00.00
ATOM   1424  O    TRP   190     -21.173   -6.845   51.022  1.00 00.00
ATOM   1425  CB   TRP   190     -22.485   -5.120   49.022  1.00 00.00
ATOM   1426  CG   TRP   190     -22.956   -4.203   50.162  1.00 00.00
ATOM   1427  CD1  TRP   190     -22.247   -3.198   50.758  1.00 00.00
ATOM   1428  CD2  TRP   190     -24.268   -4.196   50.779  1.00 00.00
ATOM   1429  CE2  TRP   190     -24.259   -3.189   51.771  1.00 00.00
ATOM   1430  CE3  TRP   190     -25.438   -4.973   50.601  1.00 00.00
ATOM   1431  NE1  TRP   190     -23.016   -2.594   51.742  1.00 00.00
ATOM   1432  CZ2  TRP   190     -25.371   -2.930   52.592  1.00 00.00
```

Fig. 2 cont.

```
ATOM   1433  CZ3 TRP   190     -26.573  -4.700  51.413  1.00 00.00
ATOM   1434  CH2 TRP   190     -26.532  -3.695  52.381  1.00 00.00
ATOM   1435  N   GLN   191     -19.588  -5.230  51.013  1.00 00.00
ATOM   1436  CA  GLN   191     -19.246  -5.478  52.391  1.00 00.00
ATOM   1437  C   GLN   191     -20.147  -4.635  53.302  1.00 00.00
ATOM   1438  O   GLN   191     -19.958  -3.437  53.450  1.00 00.00
ATOM   1439  CB  GLN   191     -17.757  -5.243  52.661  1.00 00.00
ATOM   1440  CG  GLN   191     -17.313  -5.826  54.053  1.00 00.00
ATOM   1441  CD  GLN   191     -15.907  -5.388  54.407  1.00 00.00
ATOM   1442  NE2 GLN   191     -14.950  -6.325  54.391  1.00 00.00
ATOM   1443  OE1 GLN   191     -15.679  -4.212  54.659  1.00 00.00
ATOM   1444  N   ASN   192     -21.134  -5.282  53.913  1.00 00.00
ATOM   1445  CA  ASN   192     -22.235  -4.568  54.493  1.00 00.00
ATOM   1446  C   ASN   192     -22.092  -4.324  55.993  1.00 00.00
ATOM   1447  O   ASN   192     -22.880  -3.582  56.559  1.00 00.00
ATOM   1448  CB  ASN   192     -23.574  -5.305  54.204  1.00 00.00
ATOM   1449  CG  ASN   192     -23.610  -6.714  54.791  1.00 00.00
ATOM   1450  ND2 ASN   192     -24.617  -6.994  55.587  1.00 00.00
ATOM   1451  OD1 ASN   192     -22.774  -7.538  54.482  1.00 00.00
ATOM   1452  N   SER   193     -21.116  -4.967  56.621  1.00 00.00
ATOM   1453  CA  SER   193     -20.790  -4.727  58.045  1.00 00.00
ATOM   1454  C   SER   193     -19.403  -5.252  58.356  1.00 00.00
ATOM   1455  O   SER   193     -18.875  -6.101  57.597  1.00 00.00
ATOM   1456  CB  SER   193     -21.809  -5.397  58.978  1.00 00.00
ATOM   1457  OG  SER   193     -21.381  -6.696  59.319  1.00 00.00
ATOM   1458  N   ASP   194     -18.828  -4.774  59.460  1.00 00.00
ATOM   1459  CA  ASP   194     -17.553  -5.287  60.009  1.00 00.00
ATOM   1460  C   ASP   194     -17.775  -6.200  61.223  1.00 00.00
ATOM   1461  O   ASP   194     -16.848  -6.460  61.989  1.00 00.00
ATOM   1462  CB  ASP   194     -16.575  -4.142  60.354  1.00 00.00
ATOM   1463  CG  ASP   194     -17.214  -3.014  61.201  1.00 00.00
ATOM   1464  OD1 ASP   194     -18.301  -3.206  61.817  1.00 00.00
ATOM   1465  OD2 ASP   194     -16.590  -1.927  61.274  1.00 00.00
ATOM   1466  N   LYS   195     -19.002  -6.731  61.348  1.00 00.00
ATOM   1467  CA  LYS   195     -19.407  -7.548  62.509  1.00 00.00
ATOM   1468  C   LYS   195     -20.311  -8.697  62.105  1.00 00.00
ATOM   1469  O   LYS   195     -21.457  -8.798  62.575  1.00 00.00
ATOM   1470  CB  LYS   195     -20.163  -6.660  63.509  1.00 00.00
ATOM   1471  CG  LYS   195     -19.319  -5.630  64.253  1.00 00.00
ATOM   1472  CD  LYS   195     -19.906  -4.499  64.608  1.00 00.00
ATOM   1473  CE  LYS   195     -19.014  -3.179  64.606  1.00 00.00
ATOM   1474  NZ  LYS   195     -19.790  -1.965  64.231  1.00 00.00
ATOM   1475  N   TYR   196     -19.810  -9.587  61.258  1.00 00.00
ATOM   1476  CA  TYR   196     -20.608 -10.723  60.815  1.00 00.00
ATOM   1477  C   TYR   196     -20.798 -11.598  62.042  1.00 00.00
ATOM   1478  O   TYR   196     -19.841 -11.848  62.793  1.00 00.00
ATOM   1479  CB  TYR   196     -19.825 -11.506  59.754  1.00 00.00
ATOM   1480  CG  TYR   196     -20.541 -12.733  59.255  1.00 00.00
ATOM   1481  CD1 TYR   196     -19.864 -13.931  59.104  1.00 00.00
ATOM   1482  CD2 TYR   196     -21.900 -12.674  58.906  1.00 00.00
ATOM   1483  CE1 TYR   196     -20.518 -15.078  58.617  1.00 00.00
ATOM   1484  CE2 TYR   196     -22.574 -13.805  58.422  1.00 00.00
ATOM   1485  CZ  TYR   196     -21.863 -15.007  58.287  1.00 00.00
ATOM   1486  OH  TYR   196     -22.510 -16.146  57.836  1.00 00.00
ATOM   1487  N   LYS   197     -22.013 -12.099  62.225  1.00 00.00
ATOM   1488  CA  LYS   197     -22.362 -12.771  63.488  1.00 00.00
ATOM   1489  C   LYS   197     -21.564 -14.057  63.694  1.00 00.00
ATOM   1490  O   LYS   197     -21.533 -14.624  64.834  1.00 00.00
ATOM   1491  CB  LYS   197     -23.884 -13.004  63.595  1.00 00.00
ATOM   1492  CG  LYS   197     -24.372 -14.358  63.111  1.00 00.00
ATOM   1493  CD  LYS   197     -24.586 -14.379  61.645  1.00 00.00
ATOM   1494  CE  LYS   197     -25.855 -13.611  61.254  1.00 00.00
ATOM   1495  NZ  LYS   197     -26.923 -13.733  62.250  1.00 00.00
ATOM   1496  N   HIS   198     -20.891 -14.505  62.632  1.00 00.00
ATOM   1497  CA  HIS   198     -20.011 -15.668  62.730  1.00 00.00
ATOM   1498  C   HIS   198     -18.546 -15.387  62.526  1.00 00.00
ATOM   1499  O   HIS   198     -17.773 -16.322  62.274  1.00 00.00
ATOM   1500  CB  HIS   198     -20.469 -16.786  61.778  1.00 00.00
ATOM   1501  CG  HIS   198     -21.832 -17.286  62.094  1.00 00.00
ATOM   1502  CD2 HIS   198     -22.998 -17.154  61.428  1.00 00.00
ATOM   1503  ND1 HIS   198     -22.132 -17.937  63.282  1.00 00.00
ATOM   1504  CE1 HIS   198     -23.419 -18.239  63.291  1.00 00.00
```

Fig. 2 cont.

```
ATOM   1505  NE2  HIS  198    -23.970  -17.743   62.197  1.00 00.00
ATOM   1506  N    GLY  199    -18.139  -14.110   62.635  1.00 00.00
ATOM   1507  CA   GLY  199    -16.691  -13.798   62.532  1.00 00.00
ATOM   1508  C    GLY  199    -16.335  -12.962   61.314  1.00 00.00
ATOM   1509  O    GLY  199    -16.927  -13.126   60.236  1.00 00.00
ATOM   1510  N    GLY  200    -15.365  -12.060   61.483  1.00 00.00
ATOM   1511  CA   GLY  200    -14.949  -11.183   60.392  1.00 00.00
ATOM   1512  C    GLY  200    -16.010  -10.207   59.940  1.00 00.00
ATOM   1513  O    GLY  200    -16.900   -9.803   60.734  1.00 00.00
ATOM   1514  N    ASP  201    -15.923   -9.801   58.671  1.00 00.00
ATOM   1515  CA   ASP  201    -16.837   -8.837   58.125  1.00 00.00
ATOM   1516  C    ASP  201    -17.899   -9.568   57.366  1.00 00.00
ATOM   1517  O    ASP  201    -17.605  -10.587   56.799  1.00 00.00
ATOM   1518  CB   ASP  201    -16.094   -7.922   57.138  1.00 00.00
ATOM   1519  CG   ASP  201    -14.914   -7.228   57.789  1.00 00.00
ATOM   1520  OD1  ASP  201    -15.053   -6.820   58.959  1.00 00.00
ATOM   1521  OD2  ASP  201    -13.827   -7.198   57.192  1.00 00.00
ATOM   1522  N    SER  202    -19.087   -8.990   57.259  1.00 00.00
ATOM   1523  CA   SER  202    -20.156   -9.571   56.394  1.00 00.00
ATOM   1524  C    SER  202    -20.074   -9.085   54.948  1.00 00.00
ATOM   1525  O    SER  202    -19.719   -7.905   54.700  1.00 00.00
ATOM   1526  CB   SER  202    -21.543   -9.262   57.001  1.00 00.00
ATOM   1527  OG   SER  202    -22.606   -9.707   56.171  1.00 00.00
ATOM   1528  N    ASP  203    -20.438   -9.969   54.006  1.00 00.00
ATOM   1529  CA   ASP  203    -20.469   -9.627   52.582  1.00 00.00
ATOM   1530  C    ASP  203    -21.756  -10.165   51.932  1.00 00.00
ATOM   1531  O    ASP  203    -22.277  -11.218   52.333  1.00 00.00
ATOM   1532  CB   ASP  203    -19.238  -10.206   51.879  1.00 00.00
ATOM   1533  CG   ASP  203    -17.933   -9.589   52.361  1.00 00.00
ATOM   1534  OD1  ASP  203    -17.629   -8.432   51.971  1.00 00.00
ATOM   1535  OD2  ASP  203    -17.167  -10.276   53.105  1.00 00.00
ATOM   1536  N    LYS  204    -22.236   -9.462   50.906  1.00 00.00
ATOM   1537  CA   LYS  204    -23.265   -9.982   50.032  1.00 00.00
ATOM   1538  C    LYS  204    -22.847   -9.981   48.593  1.00 00.00
ATOM   1539  O    LYS  204    -22.385   -8.955   48.072  1.00 00.00
ATOM   1540  CB   LYS  204    -24.472   -9.102   50.137  1.00 00.00
ATOM   1541  CG   LYS  204    -24.876   -8.848   51.533  1.00 00.00
ATOM   1542  CD   LYS  204    -25.677  -10.005   52.051  1.00 00.00
ATOM   1543  CE   LYS  204    -26.373   -9.583   53.326  1.00 00.00
ATOM   1544  NZ   LYS  204    -27.573  -10.457   53.515  1.00 00.00
ATOM   1545  N    PHE  205    -23.043  -11.112   47.918  1.00 00.00
ATOM   1546  CA   PHE  205    -22.755  -11.174   46.500  1.00 00.00
ATOM   1547  C    PHE  205    -23.993  -10.689   45.722  1.00 00.00
ATOM   1548  O    PHE  205    -25.123  -10.930   46.135  1.00 00.00
ATOM   1549  CB   PHE  205    -22.378  -12.588   46.081  1.00 00.00
ATOM   1550  CG   PHE  205    -22.386  -12.783   44.604  1.00 00.00
ATOM   1551  CD1  PHE  205    -21.301  -12.390   43.839  1.00 00.00
ATOM   1552  CD2  PHE  205    -23.528  -13.301   43.970  1.00 00.00
ATOM   1553  CE1  PHE  205    -21.319  -12.502   42.427  1.00 00.00
ATOM   1554  CE2  PHE  205    -23.566  -13.441   42.565  1.00 00.00
ATOM   1555  CZ   PHE  205    -22.456  -13.046   41.786  1.00 00.00
ATOM   1556  N    ASN  206    -23.758  -10.016   44.593  1.00 00.00
ATOM   1557  CA   ASN  206    -24.815   -9.346   43.822  1.00 00.00
ATOM   1558  C    ASN  206    -25.405  -10.306   42.795  1.00 00.00
ATOM   1559  O    ASN  206    -24.996  -10.291   41.630  1.00 00.00
ATOM   1560  CB   ASN  206    -24.264   -8.126   43.060  1.00 00.00
ATOM   1561  CG   ASN  206    -25.362   -7.160   42.654  1.00 00.00
ATOM   1562  ND2  ASN  206    -24.990   -5.907   42.382  1.00 00.00
ATOM   1563  OD1  ASN  206    -26.558   -7.523   42.669  1.00 00.00
ATOM   1564  N    GLY  207    -26.322  -11.149   43.247  1.00 00.00
ATOM   1565  CA   GLY  207    -27.003  -12.103   42.383  1.00 00.00
ATOM   1566  C    GLY  207    -27.217  -13.453   43.067  1.00 00.00
ATOM   1567  O    GLY  207    -26.895  -13.624   44.261  1.00 00.00
ATOM   1568  N    PRO  208    -27.767  -14.426   42.308  1.00 00.00
ATOM   1569  CA   PRO  208    -27.976  -15.773   42.802  1.00 00.00
ATOM   1570  C    PRO  208    -26.729  -16.666   42.733  1.00 00.00
ATOM   1571  O    PRO  208    -25.681  -16.308   42.134  1.00 00.00
ATOM   1572  CB   PRO  208    -29.081  -16.313   41.876  1.00 00.00
ATOM   1573  CG   PRO  208    -28.838  -15.619   40.578  1.00 00.00
ATOM   1574  CD   PRO  208    -28.367  -14.223   40.971  1.00 00.00
ATOM   1575  N    MET  209    -26.874  -17.851   43.309  1.00 00.00
ATOM   1576  CA   MET  209    -25.789  -18.786   43.396  1.00 00.00
```

Fig. 2 cont.

```
ATOM   1577  C    MET  209   -25.158 -19.079  42.043  1.00 00.00
ATOM   1578  O    MET  209   -23.951 -19.211  41.968  1.00 00.00
ATOM   1579  CB   MET  209   -26.279 -20.059  44.087  1.00 00.00
ATOM   1580  CG   MET  209   -25.206 -20.860  44.741  1.00 00.00
ATOM   1581  SD   MET  209   -24.123 -19.945  45.882  1.00 00.00
ATOM   1582  CE   MET  209   -22.595 -20.805  45.581  1.00 00.00
ATOM   1583  N    THR  210   -25.963 -19.204  40.980  1.00 00.00
ATOM   1584  CA   THR  210   -25.409 -19.489  39.646  1.00 00.00
ATOM   1585  C    THR  210   -24.474 -18.390  39.154  1.00 00.00
ATOM   1586  O    THR  210   -23.394 -18.690  38.627  1.00 00.00
ATOM   1587  CB   THR  210   -26.487 -19.769  38.548  1.00 00.00
ATOM   1588  CG2  THR  210   -27.436 -20.916  38.974  1.00 00.00
ATOM   1589  OG1  THR  210   -27.244 -18.568  38.316  1.00 00.00
ATOM   1590  N    GLN  211   -24.890 -17.127  39.331  1.00 00.00
ATOM   1591  CA   GLN  211   -24.022 -15.973  39.052  1.00 00.00
ATOM   1592  C    GLN  211   -22.729 -16.001  39.922  1.00 00.00
ATOM   1593  O    GLN  211   -21.624 -15.736  39.424  1.00 00.00
ATOM   1594  CB   GLN  211   -24.808 -14.646  39.190  1.00 00.00
ATOM   1595  CG   GLN  211   -23.928 -13.387  39.068  1.00 00.00
ATOM   1596  CD   GLN  211   -24.585 -12.170  38.376  1.00 00.00
ATOM   1597  NE2  GLN  211   -23.821 -11.538  37.468  1.00 00.00
ATOM   1598  OE1  GLN  211   -25.721 -11.770  38.689  1.00 00.00
ATOM   1599  N    LEU  212   -22.846 -16.391  41.195  1.00 00.00
ATOM   1600  CA   LEU  212   -21.617 -16.507  42.026  1.00 00.00
ATOM   1601  C    LEU  212   -20.682 -17.630  41.523  1.00 00.00
ATOM   1602  O    LEU  212   -19.448 -17.447  41.439  1.00 00.00
ATOM   1603  CB   LEU  212   -21.966 -16.683  43.496  1.00 00.00
ATOM   1604  CG   LEU  212   -20.812 -17.030  44.457  1.00 00.00
ATOM   1605  CD1  LEU  212   -19.783 -15.878  44.497  1.00 00.00
ATOM   1606  CD2  LEU  212   -21.375 -17.255  45.841  1.00 00.00
ATOM   1607  N    ARG  213   -21.277 -18.771  41.117  1.00 00.00
ATOM   1608  CA   ARG  213   -20.469 -19.844  40.533  1.00 00.00
ATOM   1609  C    ARG  213   -19.786 -19.359  39.275  1.00 00.00
ATOM   1610  O    ARG  213   -18.639 -19.743  39.001  1.00 00.00
ATOM   1611  CB   ARG  213   -21.279 -21.118  40.283  1.00 00.00
ATOM   1612  CG   ARG  213   -21.732 -21.813  41.559  1.00 00.00
ATOM   1613  CD   ARG  213   -22.056 -23.274  41.324  1.00 00.00
ATOM   1614  NE   ARG  213   -22.888 -23.808  42.413  1.00 00.00
ATOM   1615  CZ   ARG  213   -22.438 -24.115  43.633  1.00 00.00
ATOM   1616  NH1  ARG  213   -21.147 -23.928  43.948  1.00 00.00
ATOM   1617  NH2  ARG  213   -23.279 -24.604  44.543  1.00 00.00
ATOM   1618  N    LYS  214   -20.447 -18.454  38.539  1.00 00.00
ATOM   1619  CA   LYS  214   -19.827 -17.830  37.361  1.00 00.00
ATOM   1620  C    LYS  214   -18.644 -16.914  37.733  1.00 00.00
ATOM   1621  O    LYS  214   -17.616 -16.924  37.071  1.00 00.00
ATOM   1622  CB   LYS  214   -20.849 -17.064  36.514  1.00 00.00
ATOM   1623  CG   LYS  214   -20.306 -16.651  35.129  1.00 00.00
ATOM   1624  CD   LYS  214   -20.783 -15.257  34.714  1.00 00.00
ATOM   1625  CE   LYS  214   -20.037 -14.752  33.484  1.00 00.00
ATOM   1626  NZ   LYS  214   -20.274 -13.298  33.232  1.00 00.00
ATOM   1627  N    LEU  215   -18.786 -16.105  38.784  1.00 00.00
ATOM   1628  CA   LEU  215   -17.603 -15.295  39.227  1.00 00.00
ATOM   1629  C    LEU  215   -16.428 -16.241  39.520  1.00 00.00
ATOM   1630  O    LEU  215   -15.264 -15.953  39.186  1.00 00.00
ATOM   1631  CB   LEU  215   -17.951 -14.433  40.453  1.00 00.00
ATOM   1632  CG   LEU  215   -16.807 -13.725  41.188  1.00 00.00
ATOM   1633  CD1  LEU  215   -16.223 -12.616  40.340  1.00 00.00
ATOM   1634  CD2  LEU  215   -17.322 -13.191  42.493  1.00 00.00
ATOM   1635  N    ALA  216   -16.735 -17.386  40.136  1.00 00.00
ATOM   1636  CA   ALA  216   -15.665 -18.342  40.485  1.00 00.00
ATOM   1637  C    ALA  216   -15.030 -18.982  39.259  1.00 00.00
ATOM   1638  O    ALA  216   -13.802 -19.086  39.173  1.00 00.00
ATOM   1639  CB   ALA  216   -16.176 -19.427  41.466  1.00 00.00
ATOM   1640  N    SER  217   -15.862 -19.406  38.303  1.00 00.00
ATOM   1641  CA   SER  217   -15.345 -20.170  37.156  1.00 00.00
ATOM   1642  C    SER  217   -14.708 -19.226  36.126  1.00 00.00
ATOM   1643  O    SER  217   -13.736 -19.589  35.476  1.00 00.00
ATOM   1644  CB   SER  217   -16.474 -20.969  36.498  1.00 00.00
ATOM   1645  OG   SER  217   -17.331 -20.064  35.834  1.00 00.00
ATOM   1646  N    GLY  218   -15.280 -18.025  35.971  1.00 00.00
```

Fig. 2 cont.

```
ATOM  1647  CA  GLY  218   -14.868 -17.065  34.937  1.00 00.00
ATOM  1648  C   GLY  218   -15.585 -17.369  33.624  1.00 00.00
ATOM  1649  O   GLY  218   -16.253 -18.392  33.468  1.00 00.00
```

VARIANTS OF A LYSOZYME AND POLYNUCLEOTIDES ENCODING SAME

CROSS-REFERENCE TO RELATED APPLICATIONS

This application is a 35 U.S.C. 371 national application of PCT/EP2011/052812 filed Feb. 25, 2011, which claims priority or the benefit under 35 U.S.C. 119 of European application no. 10154756.0 filed Feb. 25, 2011 and U.S. provisional application No. 61/309,065 filed Mar. 1, 2010 the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to variants of a lysozyme, polynucleotides encoding the variants and methods of producing the variants.

BACKGROUND OF THE INVENTION

Lysozyme (EC 3.2.1.17), also known as muramidase or N-acetylmuramide glycanhydrolase, catalyzes hydrolysis of 1,4-beta-linkages between N-acetylmuramic acid and N-acetyl-D-glucosamine residues in a peptidoglycan and between N-acetyl-D-glucosamine residues in chitodextrins.

Lysozyme is typically produced as a defensive mechanism against bacteria by many organisms as viruses, plants, insects, birds, reptiles and mammals. The enzyme causes the hydrolysis of bacterial cell walls by cleaving the glycosidic bonds of peptidoglycan; an important structural molecule in bacteria. After having their cell walls weakened by lysozyme action, bacterial cells lyse resulting from osmotic pressure. There is an increasing interest in the potential of lysozyme enzymes as antimicrobial agents. For example, lysozyme activity has been shown against pathogens such as *Streptococcus pneumoniae, Bacillus anthracis, Enterococcus faecium, Bacillus stearothermophilus, Clostridium botulinum, Clostridium butyricum, Clostridium perfringens, Clostridium sporogenes, Clostridium tyrobutyricum,* and *Listeria monocytogenes.*

Lysozyme has been classified into five different glycoside hydrolase (GH) families (CAZy, www.cazy.org): hen eggwhite lysozyme (GH22), goose egg-white lysozyme (GH23), bacteriophage T4 lysozyme (GH24), *Sphingomonas* flagellar protein (GH73) and *Chalaropsis* lysozymes (GH25). The lysozyme family GH25 has been found to be structurally unrelated to the other lysozyme families.

Use of lysozyme has been suggested in animal feed (see for example WO 00/21381 and WO 04/026334), in cheese production (see for example WO 05/080559), food preservation (Hughey and Johnson (1987) *Appl Environ Microbiol* 53:2165), detergents (see for example U.S. Pat. No. 5,041, 236 and EP 0425016), in oral care (see for example U.S. Pat. No. 4,355,022, WO 04/017988 and WO 08/124,764), cosmetology and dermatology, contraception, urology, and gynaecology (see for example WO 08/124,764).

Hen egg-white lysozyme is a commercially available lysozyme product. Lysozymes isolated from microbial sources are also known.

SUMMARY OF THE INVENTION

The present invention relates to lysozyme variants and nucleotide sequence encoding same. In one aspect, the present invention relates to lysozyme variants belonging to glycosyl hydrolase family 25 (GH25) comprising an alteration of an amino acid sequence at one or more positions selected from the group consisting of position number 47, 111, 108, 45, 22, 110, 120, 147, 196, 49, 55, 193, 161, 128, 131, 203, 98, 112, 55, 32, 89, 206 121, 120, 185, 113, 119, 35, 153, 158, 171, 195, 76, 164, 30, 85, 178, 183, 186, 112, 174, 187, 197, 102, 134, 108, 196, 197, 198, 56, 19, 120, 20, 135, and 203, which position corresponds to a position in amino acid sequence SEQ ID NO:3, and wherein the lysozyme variant has antimicrobial and/or lysozyme activity. In one embodiment, the lysozyme variant is a variant of a fungal lysozyme. In another embodiment, the lysozyme variant comprises an amino acid sequence having at least 75% identity to SEQ ID NO:3. In another embodiment, the lysozyme variant is a variant of an *Aspergillus fumigatus* lysozyme.

The variants of the present invention have altered properties compared to the parental lysozyme, such as altered temperature-dependent activity profile, e.g. improved thermal activity or improved activity at low or moderate temperatures (psychrophilic or mesophilic activity), improved temperature stability, improved pH activity, improved pH stability and/or, increased resistance to protease degradation.

The present invention also relates to antimicrobial compositions and antimicrobial methods comprising the lysozyme variants of the present invention. In embodiments, the present invention also relates to the use of the variants of the present invention in animal feed, cheese production, food preservation, detergents, oral care, cosmetology and dermatology.

BRIEF DESCRIPTION OF THE FIGURES

FIG. 1 is an alignment of a number of mature family 25 lysozyme amino acid sequences as follows:
*Aspergillus fumigatus* lysozyme (SEQ ID NO:3);
*Aspergillus fumigatus* lysozyme (SEQ ID NO:4);
*Aspergillus fischerianus* lysozyme (SEQ ID NO:5);
*Aspergillus clavatus* lysozyme (SEQ ID NO:6);
*Aspergillus oryzae* lysozyme (SEQ ID NO:7);
*Aspergillus terreus* lysozyme (SEQ ID NO:8);
*Aspergillus fischerianus* lysozyme (SEQ ID NO:9);
*Aspergillus fumigatus* lysozyme (SEQ ID NO:10);
*Aspergillus clavatus* lysozyme (SEQ ID NO:11);
*Aspergillus terreus* lysozyme (SEQ ID NO:12); and
*Penicillum marneffei* lysozyme (SEQ ID NO:13).
The signal peptide has been predicted using the program Signal P version 3.0. The signal peptide is not in the alignment.

FIG. 2 lists the atomic coordinates of the three-dimensional structure of the *Aspergillus fumigatus* lysozyme.

DETAILED DESCRIPTION OF THE INVENTION

The present invention relates to lysozyme variants, especially variants of lysozyme belonging to glycosyl hydrolase family 25 (GH25), comprising an alteration, preferably in the form of a substitution and/or an insertion and/or a deletion at one or more (several) positions, where the numbering of the positions corresponds to the numbering of the positions of SEQ ID NO:3. The variants of the present invention have antimicrobial and/or lysozyme activity.

DEFINITIONS

Antimicrobial activity: The term "antimicrobial activity" is defined herein as is an activity that kills or inhibits the growth of microorganisms such as algae, archea, bacteria, fungi or protozoans. The antimicrobial activity can for example be bactericidal meaning the killing of bacteria, bacteriostatic meaning the prevention of bacterial growth, or prevention of sporulation. For purposes of the present invention, antimicrobial activity is determined according to the lysozyme turbidity activity assay described in the "Materials and Methods" section.

Lysozyme activity: The term "lysozyme activity" is defined herein as a peptidoglycan N-acetylmuramoylhydrolase activity (EC 3.2.1.17) that catalyzes the hydrolysis of 1,4-beta-linkages between N-acetylmuramic acid and N-acetyl-D-glucosamine residues in a peptidoglycan and between N-acetyl-D-glucosamine residues in chitodextrins. For purposes of the present invention, lysozyme activity is determined according to the lysozyme turbidity activity assay described in the "Materials and Methods" section.

Variant: The term "variant" is defined herein as a polypeptide having antimicrobial activity and/or lysozyme activity comprising an alteration, such as a substitution, insertion, and/or deletion, of one or more (several) amino acid residues at one or more (several) specific positions which positions correspond to the amino acid positions in SEQ ID NO:3. The altered polypeptide (variant) may be obtained through human intervention by modification of the polynucleotide sequence encoding the parental enzyme. The parental enzyme may be encoded by SEQ ID NO:1 or a sequence which is at least 65%, at least 70%, at least 75%, at least 80%, at least 85%, at least 90%, at least 95%, at least 96%, at least 97%, at least 98% or at least 99% identical to one of these sequences and which encode a polypeptide having antimicrobial and/or lysozyme activity. The variant polypeptide sequence is preferably one which is not found in nature.

Wild-Type enzyme: The term "wild-type" lysozyme denotes a lysozyme expressed by a naturally occurring organism, preferably from a naturally occurring microorganism such as algae, archea, bacteria, yeast, filamentous fungus, or protzoans found in nature. The term wild-type may be used interchangeably with the term "naturally occurring".

Parent enzyme: The term "parent" lysozyme or "parental" lysozyme as used herein means a lysozyme to which a modification, e.g. substitution(s), insertion(s), deletion(s), and/or truncation(s), is made to produce the enzyme variants of the present invention. This term also refers to the polypeptide with which a variant is compared and aligned. The parent may be a naturally occurring (wild-type) polypeptide such as the enzyme of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13 or a polypeptide which is at least 65%, at least 70%, at least 75%, at least 80%, at least 85%, at least 90%, at least 95%, at least 96%, at least 97%, at least 98% at least 99% or 100% identical to one of these sequences. The parent polypeptide may also be a variant of a naturally occurring polypeptide which has been modified or altered in the amino acid sequence. A parent may also be an allelic variant, which is a polypeptide encoded by any of two or more alternative forms of a gene occupying the same chromosomal locus.

Isolated variant or polypeptide: The term "isolated variant" or "isolated polypeptide" as used herein refers to a variant or a polypeptide that is isolated from a source, e.g. the host cell from which it is expressed or the enzyme complex it is normally present in. Preferably, the polypeptide is at least 40% pure, such as, at least 60% pure, at least 80% pure, at least 90% pure or at least 95% pure, as determined by SDS-PAGE.

Substantially pure variant or polypeptide: The term "substantially pure variant" or "substantially pure polypeptide" denotes herein a polypeptide preparation that contains at most 10%, such as, at most 8%, at most 6%, at most 5%, at most 4%, at most 3%, at most 2%, at most 1%, or at most 0.5% by weight of other polypeptide material with which it is natively or recombinantly associated. It is, therefore, preferred that the substantially pure variant or polypeptide is at least 92% pure, such as, at least 94% pure, at least 95% pure, at least 96% pure, at least 96% pure, more at least 97% pure, at least 98% pure, at least 99%, at least 99.5% pure or even 100% pure by weight of the total polypeptide material present in the preparation. The variants and polypeptides of the present invention are preferably in a substantially pure form. This can be accomplished, for example, by preparing the variant or polypeptide by well-known recombinant methods or by classical purification methods.

Mature polypeptide: The term "mature polypeptide" is defined herein as a polypeptide having antimicrobial and/or lysozyme activity that is in its final form following translation and any post-translational modifications, such as N-terminal processing, C-terminal truncation, glycosylation, phosphorylation, etc. For the polypeptide defined by SEQ ID NO:2, an example of a mature lysozyme sequence starts at position 18 of SEQ ID NO:2 and ends at position 235 of SEQ ID NO:2. This mature lysozyme sequence is also shown in SEQ ID NO:3. Another example is when the lysozyme is expressed in *Aspergillus oryzae*, then the mature polypeptide start at position 26 of SEQ ID NO:2 and ends at position 235 of SEQ ID NO:2. Depending on expression system, however, the length of the actual mature polypeptide may vary, such as, e.g. 1 to 10 amino acids in length (longer or shorter) at the N and/or C termini from the predicted mature polypeptide.

Mature polypeptide coding sequence: The term "mature polypeptide coding sequence" is defined herein as a nucleotide sequence that encodes a mature polypeptide having antimicrobial and/or lysozyme activity. In one aspect, the mature polypeptide coding sequence is nucleotides 51 to 705 of SEQ ID NO:1. The mature polypeptide coding sequence may vary 3 to 30 nucleotides in length depending on the expression system. When expressed in *Aspergillus oryzae* the mature polypeptide coding sequence can for example correspond to nucleotides or 75 to 705 of SEQ ID NO:1 of SEQ ID NO:1.

Identity: The parameter "identity" as used herein describes the relatedness between two amino acid sequences or between two nucleotide sequences. For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al. (2000) supra;

http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted polypeptide that gives an E value (or expectancy score) of less than 0.001 in a tfasty search (Pearson, W. R., 1999, *Bioinformatics Methods and Protocols*, S. Misener and S. A. Krawetz, ed., pp. 185-219) with the *Aspergillus fumigatus* lysozyme (UniProt Accession No. A4DA29).

Functional fragment of a polypeptide: The term "functional fragment of a polypeptide" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20% of the antimicrobial and/or lysozyme activity of the full-length/mature polypeptide, such as, at least 40%, at least 50%, at least 60%, at least 70%, at least 80%, at least 90%, at least 95%, or at least 100% of the antimicrobial and/or lysozyme activity of the full-length/mature polypeptide.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In one aspect, the isolated polynucleotide is at least 40% pure, such as, at least 60% pure, at least 80% pure, at least 90% pure or at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered polypeptide production systems. Thus, a substantially pure polynucleotide contains at most 10%, such as, at most 8%, at most 6%, at most 5%, at most 4%, at most 3%, at most 2%, at most 1%, or at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, such as, at least 92% pure, at least 94% pure, at least 95% pure, at least 96% pure, at least 97% pure, at least 98% pure, at least 99%, or even at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semi-synthetic, synthetic origin, or any combinations thereof.

Coding sequence: When used herein, the term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Host cell: The term "host cell", as used herein, includes any cell type that is susceptible to transformation, transfection, transduction, and the like with a nucleic acid construct or a vector comprising a polynucleotide of the present invention. The term "host cell" encompasses any progeny of a parent cell that is not identical to the parent cell due to mutations that occur during replication.

Altered property: The term "altered property" is defined herein as a characteristic associated with a variant that is altered, unless otherwise stated to another reference lysozyme, and which is altered as compared relative to the parent lysozyme. Such altered properties include, but are not limited to, altered temperature-dependent activity profile, altered temperature stability, altered pH activity, altered pH stability and/or, altered resistance to protease degradation.

Improved property: The term "improved property" is defined herein as a characteristic associated with a variant that is improved, unless otherwise stated to another reference lysozyme, and which is improved compared relative to the parent lysozyme. Such improved properties include, but are not limited to improved temperature-dependent activity profile such as improved thermal activity or improved activity at low temperatures, improved temperature stability, improved pH activity, improved pH stability and/or, increased resistance to protease degradation.

Altered temperature-dependent activity profile: The term "altered temperature-dependent activity profile" as used herein describes a variant enzyme displaying an alteration of the temperature-dependent activity profile when compared to the temperature-dependent activity profile of the parent lysozyme. The temperature-dependent activity profile provides a measure of the enzyme's efficiency in preventing microbial growth, eliminating microbial cells and/or performing catalysis of a hydrolysis reaction over a range of temperatures at given conditions such as pH and solvent composition. A lysozyme has a specific temperature range wherein the polypeptide is stable and retains its enzymatic activity, outside this range the lysozyme becomes less active and potentially also less stable. Within the temperature range there generally is a temperature optimum where the lysozyme shows the highest activity.

When the alteration in the temperature-dependent activity profile is towards higher temperatures, a more thermoactive or thermophilic lysozyme is generated. By improving the activity of the lysozyme at higher temperatures, it will be able to function under conditions that require higher temperatures (e.g. from 45° C. to 110° C., preferably from 50° C. to 100° C., more preferably from 60° C. to 90° C., even more preferably from 70° C. to 80° C.), for example a disinfection or sterilization process. Furthermore, the initial rate of a reaction catalyzed by a lysozyme can be accelerated by an increase in temperature that is measured by determining thermal activity of a variant. A more thermoactive variant will lead to an increase in the rate of hydrolysis decreasing the time required and/or decreasing the enzyme concentration required for preventing microbial growth, eliminating microbial cells and/or hydrolysis when used at a temperature above the optimum temperature of the parent lysozyme.

When the alteration in the temperature-dependent activity profile is towards lower or moderate temperatures, a lysozyme with improved activity at low temperatures (e.g. from 0° C. to 20° C., preferably from 2° C. to 18° C., preferably from 5° C. to 15° C., more preferably from 8° C. to 12° C., even most preferably from 10° C. to 15° C.) or moderate temperatures (e.g. from 15° C. to 45° C., preferably from 20° C. to 40° C., preferably from 22° C. to 35° C., most preferably from 25° C. to 30° C.,) is generated. A lysozyme with increased activity at lower or moderate temperatures will prevent microbial growth, eliminate microbial cells and/or catalyze a hydrolysis reaction faster than the parent enzyme at a temperature lower than the temperature optimum of the parent enzyme defined by the temperature-dependent activity profile of the parent. Such an enzyme may for example be advantageous at washing conditions at decreased temperatures such as 5° C. to 40° C., preferably 10° C. to 30° C., more preferably from 15° C. to 25° C., even more preferably from 18° C. to 20° C. It can also be advantageous in the processing of heat-sensitive food such as lactic products, juice products or wine, or for biomediation of soils and waste water during winter in temperate countries. Another example of the utility of a lysozyme with increased activity at low temperatures is for treating cold water fish species e.g salmon and trout; such a water treatment in fish breeding plants.

In one aspect of the present invention the alteration of the temperature-dependent activity profile of a lysozyme variant improves the activity of the variant at low or moderate temperature. Preferably, the activity of the lysozyme variant is compared with the activity of the parent lysozyme at a temperature of 5° C. below the optimum temperature of the parent enzyme, preferably 10° C., more preferably 15° C. 20° C., 25° C., 30° C., 35° C., 40° C., even more preferred 45° C. and most preferred 50° C. below the optimum temperature of the parent enzyme, under which conditions the variant has an activity which is at least 1.5-fold, preferably at least 2-fold, more preferably at least 5-fold, most preferably at least 7-fold and even most preferably at least 20-fold higher than that of the parent enzyme. Preferably, the lysozyme variant at the same time maintains at least 40%, preferably at least 50%, 60%, 70% or 80%, 90%, more preferably at least 95%, even more preferably at least 100% of the activity that parent lysozyme exhibits at its temperature optimum. Preferably, the activity is tested using the lysozyme turbidity activity assay described in the "Materials and Methods" section, with the deviation of the temperature to the desired decreased temperature.

In one aspect of the present invention the alteration of the temperature-dependent activity profile of a lysozyme variant improves the activity of the variant at high temperatures. Preferably, the activity of the lysozyme variant is compared with the activity of the parent lysozyme at a temperature of 5° C. above the optimum temperature of the parent enzyme, preferably 10° C., more preferably 15° C., 20° C., 25° C., 30° C., 35° C. or 40° C., even more preferred 45° C. and most preferred 50° C. above the optimum temperature of the parent enzyme, under which conditions the variant has an activity which is at least 1.5-fold, preferably at least 2-fold, more preferably at least 5-fold, most preferably at least 7-fold and even most preferably at least 20-fold higher than that of the parent enzyme. Preferably, the lysozyme variant at the same time maintains at least 40%, preferably at least 50%, 60%, 70% or 80%, 90%, more preferably at least 95%, even more preferably at least 100% of the activity that parent lysozyme exhibits at its temperature optimum. Preferably, the activity is tested using the lysozyme turbidity activity assay described in the "Materials and Methods" section, with the deviation of the temperature to the desired increased temperature.

Improved temperature stability: The term "temperature stability" or "improved thermostability" is defined herein as a variant enzyme displaying retention of enzymatic activity after a period of incubation at elevated temperature relative to the parent enzyme. Such a variant may or may not display an altered thermal activity profile relative to the parent. For example, the variant may not be active at the elevated temperatures, but is able to maintain its three dimensional structure and then regain activity once it is returned to lower temperatures. Alternatively, the variant may have an improved ability to refold following incubation at elevated temperature relative to the parent enzyme.

In one aspect, the thermal stability of a lysozyme variant is improved such that the variant can survive high temperatures e.g. temperatures from 45° C. to 110° C., preferably from 50° C. to 100° C., more preferably from 60° C. to 90° C., even more preferably from 70° C. to 80° C. Preferably, the variant lysozyme maintains at least 40%, preferably at least 50%, 60%, 70% or 80%, more preferably at least 90%, even more preferably at least 95% residual activity after incubation at a given high temperature for 1 hour when compared to the variant which has been maintained at room temperature for the same time. Preferably, the residual activity of the variant lysozyme is at least 1.5-fold, preferably at least 2-fold, more preferably at least 5-fold, most preferably at least 7-fold, and even most preferably at least 20-fold higher than the residual activity of the parent lysozyme which has been treated under the same conditions. Preferably the activity is tested using the lysozyme turbidity activity assay described in the "Materials and Methods" section, with the deviation of the temperature to the desired increased temperature.

Improved pH activity: The term "improved pH activity" is defined herein as a variant enzyme displaying an alteration of the pH-dependent activity profile when compared to the pH activity profile of the parent lysozyme. The pH activity profile provides a measure of the enzyme's efficiency in preventing microbial growth, eliminating microbial cells and/or performing catalysis of a hydrolysis reaction over a pH range at given conditions such as temperature and solvent composition. A lysozyme has a specific pH range wherein the polypeptide is stable and retains its enzymatic activity, outside this range the lysozyme becomes less active and potentially also less stable. Within the pH range there generally is a pH optimum, where the lysozyme shows the highest activity.

A lysozyme variant with improved activity at alkaline pH (e.g. from pH 7.5 to 12, preferably from 8 to 11, more preferably from 8.5 to 10, even more preferably from 9 to 9.5) will be able to function in more alkaline environments such as detergents.

A variant with improved activity at acidic pH (e.g. from pH 2 to 5.5, preferably from 2.5 to 5.25, more preferably from 3 to 5, even more preferably from 3.5 to 4) will be able to function under more acidic conditions, such as preservative in certain foods or as a eubiotic molecule in feeds.

In one aspect, the pH activity profile is altered such that a lysozyme variant has improved activity at alkaline pH. Preferably, the activity of the lysozyme variant is compared with the activity of the parent lysozyme at a pH at least 0.5 units above the optimum pH of the parent enzyme, preferably 1, 1.5, 2, 2.5 or 3 pH units above the optimum pH of the parent enzyme, most preferably at least 3.5 pH units above the optimum pH of the parent enzyme and most preferably at least 4 pH units above the optimum pH of the parent enzyme, under which conditions the variant has an activity which is at least 1.5-fold, preferably at least 2-fold, more preferably at least 5-fold, most preferably at least 7-fold and even most preferably at least 20-fold higher than that of the parent enzyme. Preferably, the lysozyme variant at the same time maintains at least 40%, preferably at least 50%, 60%, 70% or 80%, or 90%, more preferably at least 95%, even more preferably at least 100% of the activity that parent lysozyme exhibits at its pH optimum. Preferably, the activity is tested using the lysozyme turbidity activity assay described in the "Materials and Methods" section, with the deviation of the pH to the desired increased pH.

In one aspect, the pH activity profile is altered such that a lysozyme variant has improved activity at acidic pH. Preferably, the activity of the lysozyme variant is compared with the activity of the parent lysozyme at a pH at least 0.5 units below the optimum pH of the parent enzyme, preferably 1, 1.5, 2, 2.5 or 3 pH units below the optimum pH of the parent enzyme, most preferably at least 3.5 pH units below the optimum pH of the parent enzyme and most preferably at least 4 pH units below the optimum pH of the parent enzyme, under which conditions the variant has an activity which is at least 1.5-fold, preferably at least 2-fold, more preferably at least 5-fold, most preferably at least 7-fold and even most preferably at least 20-fold higher than that of the parent enzyme. Preferably, the lysozyme variant at the same time maintains at least 40%, preferably at least 50%, 60%, 70% or 80%, or 90%, more preferably at least 95%, even more preferably at least 100% of the activity that parent lysozyme exhibits at its pH optimum. Preferably the activity is tested using the lysozyme turbidity activity assay described in the "Materials and Methods" section, with the deviation of the pH to the desired decreased pH.

Improved pH stability: The term "improved pH stability" is defined herein as a variant enzyme displaying structural stability relative to the parent enzyme after a period of incubation at a pH which is outside the pH range where the enzyme is active (pH activity range). Such a variant may or may not display an altered pH activity profile relative to the parent. For example, the variant may not be active at the increased or decreased pH, but is able to maintain its three dimensional structure and then regain activity once it is returned to the pH activity range. Alternatively, the variant may have an improved ability to refold relative to the parent following incubation at increased or decreased pH.

In one aspect, the pH stability profile is altered such that a lysozyme variant has improved stability at acidic pH (e.g. from pH 2 to 5.5, preferably from 2.5 to 5.25, more preferably from 3 to 5, even more preferably from 3.5 to 4). Preferably, the variant lysozyme maintains at least 40%, preferably at least 50%, 60%, 70% or 80%, more preferably at least 90%, even more preferably at least 95% residual activity after incubation at a given pH for 1 hour when compared to the variant which has been maintained at pH 6.5 for the same time. Preferably, the residual activity of the variant lysozyme is at least 1.5-fold, preferably at least 2-fold, more preferably at least 5-fold, most preferably at least 7-fold, and even most preferably at least 20-fold higher than the residual activity of the parent lysozyme which has been treated under the same conditions. Preferably, the activity is tested using the lysozyme turbidity activity assay described in the "Materials and Methods" section, with the deviation of the pH to the desired decreased pH.

In one aspect, the pH stability profile is altered such that a lysozyme variant has improved stability at alkaline pH (e.g. from pH 7.5 to 12, preferably from 8 to 11, more preferably from 8.5 to 10, even more preferably from 9 to 9.5). Preferably, the variant lysozyme maintains at least 40%, preferably at least 50%, 60%, 70% or 80%, more preferably at least 90%, even more preferably at least 95% residual activity after incubation at a given pH for 1 hour when compared to the variant which has been maintained at pH 6.5 for the same time. Preferably, the residual activity of the variant lysozyme is at least 1.5-fold, preferably at least 2-fold, more preferably at least 5-fold, most preferably at least 7-fold, and even most preferably at least 20-fold higher than the residual activity of the parent lysozyme which has been treated under the same conditions. Preferably, the activity is tested using the lysozyme turbidity activity assay described in the "Materials and Methods" section, with the deviation of the pH to the desired increased pH.

Improved protease stability: The term "improved protease stability" is defined herein as a variant enzyme displaying structural stability relative to the parent enzyme after a period of incubation with a protease (e.g. a pepsin or a serine-proteases such as trypsin or chymotrypsin from the digestive system of an animal or human) and/or bile salts. Preferably, the protease stable variant is also stable at acidic pH (e.g. from pH 2 to 5.5, preferably from 2.5 to 5.25, more preferably from 3 to 5, even more preferably from 3.5 to 4). Such a variant may or may not display an altered activity profile relative to the parent. The variant may for example have an improved ability to refold relative to the parent following incubation with proteases and/or incubation at a decreased pH. With respect to the decreased pH, the variant may not be active during the incubation at the decreased pH, but is able to maintain its three dimensional structure and then regain activity once it is returned to the pH activity range.

In one aspect, the protease stability is improved such that a lysozyme variant has improved stability following incubation with a protease and/or a bile salt. Preferably, the variant lysozyme maintains at least 40%, preferably at least 50%, 60%, 70% or 80%, more preferably at least 90%, even more preferably at least 95% residual activity after incubation with a serine-protease and/or bile salt for 1 hour when compared to the variant which has been incubated without protease and/or bile salt for the same time. Preferably, the residual activity of the variant lysozyme is at least 1.5-fold, preferably at least 2-fold, more preferably at least 5-fold, most preferably at least 7-fold, and even most preferably at least 20-fold higher than the residual activity of the parent lysozyme which has been treated under the same conditions. Preferably, the activity is tested using the lysozyme turbidity activity assay described in the "Materials and Methods" section, with the deviation that serine-protease, pepsin and/or bile salts are added.

In a further aspect, the protease stability is improved as described above and the pH stability profile is altered such that a lysozyme variant has improved stability at acidic pH (e.g. from pH 2 to 5.5, preferably from 2.5 to 5.25, more preferably from 3 to 5, even more preferably from 3.5 to 4). Preferably, the variant lysozyme maintains at least 40%, preferably at least 50%, 60%, 70% or 80%, more preferably at least 90%, even more preferably at least 95% residual activity after incubation at a given pH with a serine-protease and/or bile salt for 1 hour when compared to the variant which has been maintained at pH 6.5 without protease and/or bile salts for the same time. Preferably, the residual activity of the variant lysozyme is at least 1.5-fold, preferably at least 2-fold, more preferably at least 5-fold, most preferably at least 7-fold, and even most preferably at least 20-fold higher than the residual activity of the parent lysozyme which has been treated under the same conditions. Preferably, the activity is tested using the lysozyme turbidity activity assay described in the "Materials and Methods" section, with the deviation of the pH to the desired decreased pH and serine-protease, pepsin and/or bile salts is added.

Conventions for Designation of Variants

For purposes of the present invention, the amino acid sequence of the lysozyme disclosed in SEQ ID NO:3 is used to determine the corresponding amino acid residue in another lysozyme. The amino acid sequence of another lysozyme is aligned with the amino acid sequence of the lysozyme disclosed in SEQ ID NO:3, and based on the alignment the amino acid position number corresponding to any amino acid residue in the amino acid sequence of the lysozyme disclosed in SEQ ID NO:3 can be determined.

An alignment of polypeptide sequences may be made using the Needleman-Wunsch algorithm (Needleman and Wunsch (1970) *J. Mol. Biol.* 48:443-453) as implemented in the Needle program of the EMBOSS package (EMBOSS: The European Molecular Biology Open Software Suite, Rice et al. (2000) *Trends in Genetics* 16:276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix.

In describing the various lysozyme variants of the present invention, the nomenclature described below is adapted for ease of reference. In all cases, the accepted IUPAC single letter or triple letter amino acid abbreviation is employed.

The alteration(s) are an insertion and/or deletion of the amino acid which occupies the position, and/or a substitution of the amino acid which occupies the position with a different amino acid.

Substitutions. For an amino acid substitution, the following nomenclature is used: original amino acid,/position/substituted amino acid. Accordingly, the substitution of threonine with alanine at position 226 is designated as "Thr226Ala" or "T226A". Multiple mutations are separated by addition marks ("+"), e.g., "G205R+S411F", representing mutations at positions 205 and 411 substituting glycine (G) with arginine (R), and serine (S) with phenylalanine (F), respectively. Where an original amino acid may be substituted by an amino acid selected from a group it is designated as "K129R,S,A,I,F,Q" representing the substitution of a lysine (K) at position 129 with an amino acid selected from the group consisting of: arginine (R), serine (S), alanine (A), isoleucine (I), phenylalanine (F) and glutamine (Q). Alternatively, "K129R,S,A,I,F,Q" could be written as K129R or K129S, or K129A, or K129I or K129F or K129Q Deletions. For an amino acid deletion, the following nomenclature is used: original amino acid/position/asterisk (*). Accordingly, the deletion of glycine at position 195 is designated as "Gly195*" or "G195*". Multiple deletions are separated by addition marks ("+"), e.g. G195*+S411*.

Insertions. For an amino acid insertion, the following nomenclature is used: asterisk (*)/position/lower case letter/ inserted amino acid, where the lower case letter indicates the addition of an amino acid downstream of the position number. Accordingly, the insertion of a glutamic acid (E) downstream of position 10 is designated "*10aE". If a second amino acid, e.g. a valine (V), is to be inserted downstream of position 10 after the glutamic acid (E) it is designated "*10aE+*10bV". Additions to the N-terminal of the polypeptide are designated with a 0 (zero). The addition of a glutamic acid (E) and a valine (V) added to the N-terminal amino acid of a polypeptide is designated as "*0aE+*0bV". A "downstream" insertion can also be described as the addition of one or more amino acids between the named position and the position immediately following the named position, e.g. an insertion downstream of position 195 results in the addition of one or more amino acids between position 195 and 196, thereby generating new positions *195a, *195b and so forth.

Parent Lysozymes

In the present invention, the parent lysozyme is either a lysozyme belonging to family 25 of glycosyl hydrolases also termed "family 25 lysozymes", preferably a fungal family 25 lysozyme. Family 25 of glycosyl hydrolases or lysozymes is defined herein as a polypeptide falling into the glycoside hydrolase family 25 according to Henrissat B. (1991) *Biochem. J.* 280:309-316; and Henrissat B., and Bairoch A. (1996) *Biochem. J.* 316:695-696.

Examples or parent lysozymes include lysozymes derived from *Aspergillus* or *Penicillium*, such as, *Aspergillus fumigatus, Aspergillus fischerianus, Aspergillus clavatus, Aspgerillus oryzae, Aspergillus terreus, Penicillum marneffei*. Specific examples of lysozymes include the *Aspergillus fumigatus* lysozyme (SEQ ID NO:3); *Aspergillus fumigatus* lysozyme (SEQ ID NO:4); *Aspergillus fischerianus* lysozyme (SEQ ID NO:5); *Aspergillus clavatus* lysozyme (SEQ ID NO:6); *Aspergillus oryzae* lysozyme (SEQ ID NO:7); *Aspergillus terreus* lysozyme (SEQ ID NO:8); *Aspergillus fischerianus* lysozyme (SEQ ID NO:9); (SEQ ID NO:10); *Aspergillus fumigatus* lysozyme *Aspergillus clavatus* lysozyme (SEQ ID NO:11); *Aspergillus terreus* lysozyme (SEQ ID NO:12); and *Penicillum marneffei* lysozyme (SEQ ID NO:13). An alignment of these lysozyme amino acid sequences is shown in FIG. 1.

A representative structure of the family 25 lysozymes is provided in the atomic coordinates attached as FIG. 2 for the *Aspergillus fumigatus* lysozymes of SEQ ID NO:3.

In one embodiment a GH25 lysozyme is defined as a polypeptide comprising the following motifs:
[GA]-X-Y-[HF]-[FY]-X(6,15)-[QED]-[AV]-X(2,5)-[FYW]-X(8,17)-[PKMYASRVLI]-X(2)-[VLI]-D-X-E,
wherein the standard IUPAC one-letter codes for the amino acids are used. The symbol "X" is used for a position where any amino acid is accepted. Ambiguities are indicated by listing the acceptable amino acids for a given position, between square brackets "[ ]". For example stands [QED] for Gln or Glu or Asp. A gap ("X") in the pattern is indicated by a numerical range between parentheses. For example corresponds "X(2)" to any amino acid at two contiguous positions (e.g. X-X), and X(2,5) corresponds to any amino acid from two to five contiguous positions (e.g. X-X or X-X-X or X-X-X-X or X-X-X-X-X).

In another embodiment, the parental lysozyme is (a) a polypeptide corresponding to the mature peptide of SEQ ID NO:2; or (b) a polypeptide comprising an amino acid sequence having at least at least 65%, at least 70%, at least 75%, at least 80%, at least 85%, at least 90%, at least 95%, at least 96%, at least 97%, at least 98% at least 99% or 100% with the mature polypeptide of SEQ ID NO:2; or (c) a polypeptide encoded by a polynucleotide that hybridizes under at least medium stringency conditions with (i) the mature polypeptide encoded by sequence of SEQ ID NO:1, (ii) the genomic DNA sequence comprising the mature polypeptide coding sequence of SEQ ID NO:1, or (iii) a full-length complementary strand of (i) or (ii); or (d) a polypeptide encoded by a polynucleotide comprising a nucleotide sequence having at least at least 65%, at least 70%, at least 75%, at least 80%, at least 85%, at least 90%, at least 95%, at least 96%, at least 97%, at least 98%, at least 99%, or 100% identity with the mature polypeptide coding sequence of SEQ ID NO:1.

The parent lysozyme may also comprise an amino acid sequence having a degree of identity to the polypeptide of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13 of at least 65%, at least 70%, at least 75%, at least 80%, at least 85%, at least 90%, at least 95%, at least 96%, at least 97%, at least 98%, at least 99%, or 100%, and which amino acid sequence has antimicrobial and/or lysozyme activity (hereinafter "homologous polypeptides"). In one aspect, the homologous polypeptides have an amino acid sequence that differs by twenty amino acids, nineteen amino acids, eighteen amino acids, seventeen amino acids, sixteen amino acids, fifteen amino acids, fourteen amino acids, thirteen amino acids, twelve amino acids, eleven amino acids, ten amino acids, nine amino acids, eight amino acids, seven amino acids, six amino acids, five amino acids, four amino acids, three amino acids, two amino acids, or only one amino acid from the mature polypeptide of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

Substantially homologous parent lysozymes may have one or more (several) amino acid alterations such as substitutions, deletions and/or insertions. These changes are preferably of a minor nature, that is conservative amino acid substitutions and other substitutions that do not significantly affect the three-dimensional folding or activity of the protein or polypeptide; small deletions, typically of one to about 9 amino acids, one to about 15 amino acids or one to about 30 amino acids; and small amino- or carboxyl-terminal extensions, such as an amino-terminal methionine residue, a small linker peptide of up to about five to ten residues, 10 to 15 residues, or 20 to 25 residues, or a small extension that facilitates purification (an affinity tag), such as a poly-histidine tag, or protein A (Nilsson et al. (1985) EMBO J. 4:1075; Nilsson et al. (1991) *Methods Enzymol.* 198:3. See also, in general, Ford et al. (1991) *Protein Expression and Purification* 2:95-107.

Although the changes described above preferably are of a minor nature, such changes may also be of a substantive nature such as fusion of larger polypeptides of up to 300 amino acids or more both as amino- or carboxyl-terminal extensions. Examples of fusion polypeptides include the addition of a binding domains and/or linker segments to the lysozymes of the present invention.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill (1979) *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in the lysozyme polypeptides of the present invention can be identified according to procedures known in the art, such as site-directed mutagenesis or alanine-scanning mutagenesis (Cunningham and Wells (1989) *Science* 244:1081-1085). In the latter technique, single alanine mutations are introduced at every residue in the molecule, and the resultant mutant molecules are tested for biological activity (i.e. antimicrobial and/or lysozyme activity) to identify amino acid residues that are critical to the activity of the molecule. See also Hilton et al. (1996) *J. Biol. Chem.* 271: 4699-4708. The active site of the enzyme or other biological interaction can also be determined by physical analysis of structure, as determined by such techniques as nuclear magnetic resonance, crystallography, electron diffraction or photo affinity labeling, in conjunction with mutation of putative contact site amino acids. See for example de Vos et al. (1992) *Science* 255:306-312; Smith et al. (1992) *J. Mol. Biol.* 224:899-904; Wlodaver et al. (1992) *FEBS Lett.* 309:59-64. The identities of essential amino acids can also be inferred from analysis of homologies with polypeptides which are related to a polypeptide according to the invention. The crystal structure of the fungal GH25 from *Aspergillus fumigatus* (the parent lysozyme) at a resolution of 1.8 Å is included in the present invention. This is the first crystal structure of a eukaryotic representative of the lysozyme GH25 family. The structure was used as input to the Dictionary of Protein Secondary Structure (DSSP) program in order to calculate its secondary structure. The DSSP program was designed by Wolfgang Kabsch and Chris Sander to standardize secondary structure assignment. DSSP is a database of secondary structure assignments for all protein entries in the Protein Data Bank. DSSP is also the program that calculates DSSP entries from PDB entries. DSSP is described in Kabsch W. and Sander C. (1983) "*Dictionary of protein secondary structure: pattern recognition of hydrogen-bonded and geometrical features*", Biopolymers Dec, 22(12):2577-637.

The following are the secondary structure elements of *Aspergillus fumigatus* GH25 lysozyme:

| | | beta-strands | | alpha-helices | disulfide bridge |
|---|---|---|---|---|---|
| 1 | $\beta_1$ | T11-I17 | $\alpha_1$ | F26-K31 | C115-C154 |
| 2 | $\beta_2$ | F36-E43 | $\alpha_2$ | F52-K61 | |
| 3 | $\beta_3$ | L65-F71 | $\alpha_3$ | G79-K88 | |
| 4 | $\beta_4$ | M103-D105 | $\alpha_4$ | H120-T138 | |
| 5 | $\beta_5$ | M143-T146 | $\alpha_5$ | A148-T155 | |
| 6 | $\beta_6$ | L167-A170 | $\alpha_6$ | M209-S217 | |
| 7 | $\beta_7$ | I189-S193 | | | |
| 8 | $\beta_8$ | D201-N206 | | | |

The structure of the *Aspergillus fumigatus* GH25 lysozyme comprises a single domain, with the shape of a flattened ellipsoid with dimensions of 50 Å×39 Å×36 Å. The enzyme has a β/α-barrel fold, which is different from the $(\beta/\alpha)_8$-barrels found in triosephosphate isomerase (TIM) and many other enzymes (For more details see the paper by Rau A., Hogg T., Marquardt R. and Hilgenfeld R., *A new lysozyme fold. Crystal structure of the muramidase from Streptomyces coelicolor at 1.65 Å resolution*, Journal of Biological Chemistry 2001, volume 276, pp. 31994-9). It is composed of eight β-strands and six α-helices, with the strands forming the staves of the barrel and the helices located around it. As in regular TIM barrels, the first five β-strands and α-helices alternate. However, the fifth α-helix is followed by strands β6 to β8, which are connected by loops lacking any helices. Helix α6 is located at the C terminus of the polypeptide chain, sitting at the bottom (N-terminal end) of the barrel. All β-strands are arranged parallel to one another, except strand β8 which, very unusually, is in an antiparallel orientation with respect to the other strands.

Based on the structure residues, D105 and E107 in SEQ ID NO:3 have been identified as catalytic residues. In a preferred embodiment the variant of the present invention contains aspartic acid position at 105 (using SEQ ID NO:3 numbering)

and contains glutamic acid at position 107 (using SEQ ID NO:3 numbering). Furthermore, based on the structure the following residues, D16, Q191, Y145, Y69, D201, G200, G44, G67, G14, and H70 in SEQ ID NO:3, have been identified as closely related to the active site. In a further preferred embodiment the variant of the present invention contains aspartic acid at position 16, glutamine at position 191, tyrosine at position 145, tyrosine at position 69, aspartic acid at position 201, glycine at position 200, glycine at position 44, glycine at position 67, glycine at position 14 and/or histidine at position 70 (using SEQ ID NO:3 numbering).

The parent lysozyme preferably comprises the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, SEQ ID NO:12 or SEQ ID NO:13 or an allelic variant thereof, or a fragment thereof having antimicrobial and/or lysozyme activity. In one aspect, the parent lysozyme comprises the amino acid sequence of SEQ ID NO:2. In another aspect, the parent lysozyme comprises the mature polypeptide of SEQ ID NO:2. In another aspect, the parent lysozyme comprises the polypeptide of SEQ ID NO:3 or a mature polypeptide thereof. In another aspect, the parent lysozyme comprises the polypeptide of SEQ ID NO:4 or a mature polypeptide thereof. In another aspect, the parent lysozyme comprises the polypeptide of SEQ ID NO:5 or a mature polypeptide thereof. In another aspect, the parent lysozyme comprises the polypeptide of SEQ ID NO:6 or a mature polypeptide thereof. In another aspect, the parent lysozyme comprises the polypeptide of SEQ ID NO:7 or a mature polypeptide thereof. In another aspect, the parent lysozyme comprises the polypeptide of SEQ ID NO:8 or a mature polypeptide thereof. In another aspect, the parent lysozyme comprises the polypeptide of SEQ ID NO:9 or a mature polypeptide thereof. In another aspect, the parent lysozyme comprises the polypeptide of SEQ ID NO:10 or a mature polypeptide thereof. In another aspect, the parent lysozyme comprises the polypeptide of SEQ ID NO:11 or a mature polypeptide thereof. In another aspect, the parent lysozyme comprises the polypeptide of SEQ ID NO:12 or a mature polypeptide thereof. In another aspect, the parent lysozyme comprises the polypeptide of SEQ ID NO:13 or a mature polypeptide thereof. In another aspect, the parent lysozyme consists of the amino acid sequence of SEQ ID NO:3 or an allelic variant thereof; or a fragment thereof having antimicrobial and/or lysozyme activity. In another aspect, the parent lysozyme consists of the amino acid sequence of SEQ ID NO:4 or an allelic variant thereof; or a fragment thereof having antimicrobial and/or lysozyme activity. In another aspect, the parent lysozyme consists of the amino acid sequence of SEQ ID NO:5 or an allelic variant thereof; or a fragment thereof having antimicrobial and/or lysozyme activity. In another aspect, the parent lysozyme consists of the amino acid sequence of SEQ ID NO:6 or an allelic variant thereof; or a fragment thereof having antimicrobial and/or lysozyme activity. In another aspect, the parent lysozyme consists of the amino acid sequence of SEQ ID NO:7 or an allelic variant thereof; or a fragment thereof having antimicrobial and/or lysozyme activity. In another aspect, the parent lysozyme consists of the amino acid sequence of SEQ ID NO:8 or an allelic variant thereof; or a fragment thereof having antimicrobial and/or lysozyme activity. In another aspect, the parent lysozyme consists of the amino acid sequence of SEQ ID NO:9 or an allelic variant thereof; or a fragment thereof having antimicrobial and/or lysozyme activity. In another aspect, the parent lysozyme consists of the amino acid sequence of SEQ ID NO:10 or an allelic variant thereof; or a fragment thereof having antimicrobial and/or lysozyme activity. In another aspect, the parent lysozyme consists of the amino acid sequence of SEQ ID NO:11 or an allelic variant thereof; or a fragment thereof having antimicrobial and/or lysozyme activity. In another aspect, the parent lysozyme consists of the amino acid sequence of SEQ ID NO:12 or an allelic variant thereof; or a fragment thereof having antimicrobial and/or lysozyme activity. In another aspect, the parent lysozyme consists of the amino acid sequence of SEQ ID NO:13 or an allelic variant thereof; or a fragment thereof having antimicrobial and/or lysozyme activity. In another aspect the parent lysozyme comprises an amino acid sequence which is at least 65%, at least 70%, at least 75%, at least 80%, at least 85%, at least 90%, at least 95%, at least 96%, at least 97%, at least 98%, at least 99% or 100% identical SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13. A fragment of polypeptide is a polypeptide having one or more (several) amino acids deleted from the amino- and/or carboxyl-terminus of this amino acid sequence and still maintaining antimicrobial and/or lysozyme activity.

The parent lysozymes may in another aspect be encoded by polynucleotides that hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO:1, (ii) the genomic DNA sequence comprising the mature polypeptide coding sequence of SEQ ID NO:1, (iii) a subsequence of (i) or (ii), or (iv) a full-length complementary strand of (i), (ii), or (iii) (J. Sambrook, E. F. Fritsch, and T. Maniatis (1989) *Molecular Cloning, A Laboratory Manual* ($2^{nd}$ edition), Cold Spring Harbor, N.Y.). The subsequence may encode a polypeptide fragment having antimicrobial and/or lysozyme activity. In one aspect, the complementary strand is the full-length complementary strand of the mature polypeptide coding sequence of SEQ ID NO:1.

A subsequence of the mature polypeptide coding sequence of SEQ ID NO:1, or a homolog thereof, is a nucleotide sequence where one or more (several) nucleotides have been deleted from the 5'- and/or 3'-end, where the polypeptide encoded by the subsequence possess antimicrobial and/or lysozyme activity.

The parent enzymes may also be allelic variants of the polypeptides that have antimicrobial and/or lysozyme activity.

The polynucleotide of SEQ ID NO:1, or a subsequence thereof, as well as the amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13, or a fragment thereof, may be used to design nucleic acid probes to identify and clone DNA encoding parent lysozymes from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, at least 25, at least 35, or at least 70 nucleotides in length. It is, however, preferred that the nucleic acid probe is at least 100 nucleotides in length. For example, the nucleic acid probe may be at least 200 nucleotides, at least 300 nucleotides, at least 400 nucleotides, or at least 500 nucleotides in length. Even longer probes may be used, e.g. nucleic acid probes that are at least 600 nucleotides, at least 700 nucleotides, at least 800 nucleotides, at least 900 nucleotides in length, at least 1000 nucleotides in length, at least 1100 nucleotides in length, at least 1200 nucleotides in length, at least 1300 nucleotides in length, at least 1400 nucleotides in length, at least 1500 nucleotides in length or at least 1600 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from other organisms may be screened for DNA that hybridizes with the probes described above and encodes a parent lysozyme. Genomic or other DNA from other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:1, or a subsequence thereof, the carrier material is used in a Southern blot. For purposes of the present invention, hybridization indicates that the polynucleotide hybridizes to a labeled nucleotide probe corresponding to the polynucleotide shown in SEQ ID NO:1, its complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO:1. In another aspect, the nucleic acid probe is nucleotides 51 to 705 of SEQ ID NO:1, or nucleotides 75 to 705 of SEQ ID NO:1. In another aspect, the nucleic acid probe is a polynucleotide sequence that encodes the polypeptide of SEQ ID NO:2, or a subsequence thereof. In another aspect, the nucleic acid probe is SEQ ID NO:1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (see Bolton and McCarthy (1962) *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the parent lysozyme is encoded by a polynucleotide comprising or consisting of a nucleotide sequence having a degree of identity to the mature polypeptide coding sequence of SEQ ID NO:1 of preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. In one aspect, the mature polypeptide coding sequence is nucleotides 82 to 1653 of SEQ ID NO:1, or nucleotides 97 to 1653 of SEQ ID NO:1.

The parent lysozyme may be obtained from microorganisms of any genus. In one aspect, the parent lysozyme is secreted extracellularly.

In one embodiment, the parent lysozyme is a fungal lysozyme. Examples or parent fungal lysozymes include lysozymes derived from *Aspergillus* or *Penicillium*, such as, *Aspergillus fumigatus, Aspergillus fischerianus, Aspergillus clavatus, Aspgerillus oryzae, Aspergillus terreus, Penicillum marneffei*. Specific examples of parent fungal lysozymes include the *Aspergillus fumigatus* lysozyme (SEQ ID NO:3); *Aspergillus fumigatus* lysozyme (SEQ ID NO:4); *Aspergillus fischerianus* lysozyme (SEQ ID NO:5); *Aspergillus clavatus* lysozyme (SEQ ID NO:6); *Aspergillus oryzae* lysozyme (SEQ ID NO:7); *Aspergillus terreus* lysozyme (SEQ ID NO:8); *Aspergillus fischerianus* lysozyme (SEQ ID NO:9); (SEQ ID NO:10); *Aspergillus fumigatus* lysozyme *Aspergillus clavtus* lysozyme (SEQ ID NO:11); *Aspergillus terrus* lysozyme (SEQ ID NO:12); and *Penicillum marneffei* lysozyme (SEQ ID NO:13).

In a further aspect, the parent lysozyme may be a bacterial lysozyme. For example, the lysozyme may be a Gram positive bacterial polypeptide such as a *Bacillus*, preferably from the *Bacillus anthracis* BA_GH25C (Martinez-Fleites et al. (2009) *Carbohydr Res,* 344(13):1753-1757). Other parent bacterial lysozymes may be *Streptomyces coelicolor* cellosyl (Rau et al. (2001) *J Biol Chem,* 276(34):31994-31999), the bacteriophage lysin PlyB (Porter et al. (2007) *J Mol Biol,* 366(2):540-550), or Clp-1 lysozyme from a *Streptococcus pneumoniae* phage (Perez-Dorado et al. (2007) *J Biol Chem,* 282(34):24990-24999).

Generation of Variants

Variants of a parent lysozyme can be prepared according to any mutagenesis procedure known in the art, such as random and/or site-directed mutagenesis, synthetic gene construction, semi-synthetic gene construction, random mutagenesis, shuffling, etc.

Synthetic gene construction entails in vitro synthesis of a designed polynucleotide molecule to encode a polypeptide molecule of interest. Gene synthesis can be performed utilizing a number of techniques, such as the multiplex microchip-based technology described by Tian et al. (Tian et al., *Nature* 432:1050-1054) and similar technologies wherein oligonucleotides are synthesized and assembled upon photo-programmable microfluidic chips.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide fragments may then be shuffled.

Site-directed mutagenesis is a technique in which one or several mutations are created at a defined site in a polynucleotide molecule encoding the parent lysozyme. The technique can be performed in vitro or in vivo.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent lysozyme and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. For further description of suitable techniques reference is made to: Sambrook et al. (1989) *Molecular cloning: A laboratory manual*, Cold Spring Harbor lab., Cold Spring Harbor, N.Y.; Ausubel, F. M. et al. (eds.) *Current protocols in Molecular Biology*, John Wiley and Sons (1995); Harwood, C. R., and Cutting, S. M. (eds.) *Molecular Biological Methods for Bacillus*, John Wiley and Sons (1990); WO 96/34946; Scherer and Davis (1979) *Proc. Natl. Acad. Sci. USA* 76:4949-4955; and Barton et al. (1990) *Nucleic Acids Research* 18:7349-4966.

After the ligase reaction the ligation mixture may be used to transform a host cell, for cloning purposes *E. coli* cells are often used as described in Ausubel, F. M. et al. The transformed *E. coli* cells can be propagated in liquid media or on solid agar plates, plasmids can be rescued from the transformed cells and used to transform *B. subtilis* cells. Suitable competent *Bacillus* cells, such as MB1510, a 168-derivative (e.g. available from BGSC with accession no. 1A1 168 trpC2), may be transformed as described in WO 03/095658. An *E. coli* plasmid-borne integration cassette for library construction may be used for *Bacillus* transformation. The method is described in detail in WO 03/095658. Alternatively, an in vitro amplified PCR-SOE-product (Melnikov and Youngman, *Nucleic Acid Research* 27:1056) may be used.

Site-directed mutagenesis can be accomplished in vivo by methods known in the art (see for example U.S. Patent Application Publication 2004/0171154; Storici et al. (2001) *Nature Biotechnology* 19: 773-776; Kren et al. (1998) *Nat. Med.* 4: 285-290; and Calissano and Macino (1996) *Fungal Genet. Newslett.* 43: 15-16).

Any site-directed mutagenesis procedure can be used in the present invention. There are many commercial kits available that can be used to prepare variants of parent lysozymes.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer (1988) Science 241:53-57; Bowie and Sauer (1989) *Proc. Natl. Acad. Sci. USA* 86:2152-2156; WO 95/17413; or WO 95/22625. Other methods that can be used include error-prone PCR, phage display (e.g. Lowman et al. (1991) *Biochem.* 30:10832-10837; U.S. Pat. No. 5,223,409; WO 92/06204) and region-directed mutagenesis (Derbyshire et al. (1986) *Gene* 46:145; Ner et al. (1988) *DNA* 7:127).

Mutagenesis/shuffling methods as described above can be combined with high-throughput, automated screening methods to detect the activity of cloned, mutagenized polypeptides expressed by host cells, e.g. *Bacillus* as described above. Mutagenized DNA molecules that encode polypeptides with antimicrobial and/or lysozyme activity can be recovered from the host cells and rapidly sequenced using standard methods in the art.

Variants

The isolated variants of the present invention comprise an alteration of an amino acid at one or more (several) positions selected from the group consisting of positions number 47, 111, 108, 45, 22, 110, 120, 147, 196, 49, 55, 193 161, 128, 131, 95, 203, 98, 112, 55, 32, 89, 206 121, 120, 185, 186, 176, 113, 122, 119, 35, 65, 139, 141, 153, 158, 171, 195, 76, 164, 30, 85, 178, 183, 186, 112, 174, 187, 197, 102, 134, 108, 196, 197, 198, 56, 19, 120, 20, 135, and 203, wherein the variant has antimicrobial and/or lysozyme activity. The numbering of the positions is relative to the amino acid sequence of SEQ ID NO:3.

The isolated variants of the present invention comprise an alteration of an amino acid at one or more (several) positions selected from the group consisting of positions number 47, 111, 108, 45, 22, 110, 120, 147, 196, 49, 55, 193, 161, 128, 131, 203, 98, 112, 55, 32, 89, 206 121, 120, 185, 113, 119, 35, 153, 158, 171, 195, 76, 164, 30, 85, 178, 183, 186, 112, 174, 187, 197, 102, 134, 108, 196, 197, 198, 56, 19, 120, 20, 135, and 203 wherein the variant has antimicrobial and/or lysozyme activity. The numbering of the positions is relative to the amino acid sequence of SEQ ID NO:3.

In one embodiment, the variants described above comprise an additional amino acid alteration at one or more positions selected from the group consisting of position number 95, 186, 65, 122, 139, 141 and 176.

In one embodiment, the isolated variant of the present invention comprises or consists of an alteration at position 19 (using SEQ ID NO:3 for numbering). In an embodiment the alteration is a substitution of the amino acid at position 19 with Asn. For example, the isolated variants of the present invention comprise or consist of an alteration of N19D.

In one embodiment, the isolated variant of the present invention comprises or consists of an alteration at position 20 (using SEQ ID NO:3 for numbering). In an embodiment the alteration is a substitution of the amino acid at position 20 with His or Tyr. For example, the isolated variants of the present invention comprise or consist of an alteration of H20W or H20Y.

In one embodiment, the isolated variant of the present invention comprises or consists of an alteration at position 22 (using SEQ ID NO:3 for numbering). In an embodiment the alteration is a substitution of the amino acid at position 22 with Gly. For example, the isolated variants of the present invention comprise or consist of an alteration of K22G.

In one embodiment, the isolated variant of the present invention comprises or consists of an alteration at position 30 (using SEQ ID NO:3 for numbering). In an embodiment the alteration is a substitution of the amino acid at position 30 with Tyr. For example, the isolated variants of the present invention comprise or consist of an alteration of K30Y.

In one embodiment, the isolated variant of the present invention comprises or consists of an alteration at position 32 (using SEQ ID NO:3 for numbering). In an embodiment the alteration is a substitution of the amino acid at position 32 with Ser. For example, the isolated variants of the present invention comprise or consist of an alteration of D32S.

In one embodiment, the isolated variant of the present invention comprises or consists of an alteration at position 35 (using SEQ ID NO:3 for numbering). In an embodiment the alteration is a substitution of the amino acid at position 35 with Arg. For example, the isolated variants of the present invention comprise or consist of an alteration of Q35R.

In one embodiment, the isolated variant of the present invention comprises or consists of an alteration at position 45 (using SEQ ID NO:3 for numbering). In an embodiment the alteration is a substitution of the amino acid at position 45 with Gly. For example, the isolated variants of the present invention comprise or consist of an alteration of T45G.

In one embodiment, the isolated variant of the present invention comprises or consists of an alteration at position 47 (using SEQ ID NO:3 for numbering). In an embodiment the alteration is a substitution of the amino acid at position 47 with Phe. For example, the isolated variants of the present invention comprise or consist of an alteration of Y47F.

In one embodiment, the isolated variant of the present invention comprises or consists of an alteration at position 49 (using SEQ ID NO:3 for numbering). In an embodiment the alteration is a substitution of the amino acid at position 49 with Ala. For example, the isolated variants of the present invention comprise or consist of an alteration of D49A.

In one embodiment, the isolated variant of the present invention comprises or consists of an alteration at position 55 (using SEQ ID NO:3 for numbering). In an embodiment the alteration is a substitution of the amino acid at position 55 with Ala or Asn. For example, the isolated variants of the present invention comprise or consist of an alteration of H55A or H55N.

In one embodiment, the isolated variant of the present invention comprises or consists of an alteration at position 56 (using SEQ ID NO:3 for numbering). In an embodiment the alteration is a substitution of the amino acid at position 56 with Trp. For example, the isolated variants of the present invention comprise or consist of an alteration of Y56W.

In one embodiment, the isolated variant of the present invention comprises or consists of an alteration at position 65 (using SEQ ID NO:3 for numbering). In an embodiment the alteration is a substitution of the amino acid at position 65 with ILe. For example, the isolated variants of the present invention comprise or consist of an alteration of L65I.

In one embodiment, the isolated variant of the present invention comprises or consists of an alteration at position 76 (using SEQ ID NO:3 for numbering). In an embodiment the alteration is a substitution of the amino acid at position 76 with Ser. For example, the isolated variants of the present invention comprise or consist of an alteration of K76S.

In one embodiment, the isolated variant of the present invention comprises or consists of an alteration at position 85 (using SEQ ID NO:3 for numbering). In an embodiment the alteration is a substitution of the amino acid at position 85 with Tyr. For example, the isolated variants of the present invention comprise or consist of an alteration of K85Y.

In one embodiment, the isolated variant of the present invention comprises or consists of an alteration at position 89 (using SEQ ID NO:3 for numbering). In an embodiment the alteration is a substitution of the amino acid at position 89 with Thr. For example, the isolated variants of the present invention comprise or consist of an alteration of N89T.

In one embodiment, the isolated variant of the present invention comprises or consists of an alteration at position 95 (using SEQ ID NO:3 for numbering). In an embodiment the alteration is a substitution of the amino acid at position 95 with Gly. For example, the isolated variants of the present invention comprise or consist of an alteration of D95G.

In one embodiment, the isolated variant of the present invention comprises or consists of an alteration at position 98 (using SEQ ID NO:3 for numbering). In an embodiment the alteration is a substitution of the amino acid at position 98 with Gly. For example, the isolated variants of the present invention comprise or consist of an alteration of R98G.

In one embodiment, the isolated variant of the present invention comprises or consists of an alteration at position 102 (using SEQ ID NO:3 for numbering). In an embodiment the alteration is a substitution of the amino acid at position 102 with Pro. For example, the isolated variants of the present invention comprise or consist of an alteration of G102P. The variant may also further comprise an alteration of Y134V.

In one embodiment, the isolated variant of the present invention comprises or consists of an alteration at position 108 (using SEQ ID NO:3 for numbering). In an embodiment the alteration is a substitution of the amino acid at position 108 with Phe or Trp. For example, the isolated variants of the present invention comprise or consist of an alteration of Y108F or Y108W.

In one embodiment, the isolated variant of the present invention comprises or consists of an alteration at position 110 (using SEQ ID NO:3 for numbering). In an embodiment the alteration is a substitution of the amino acid at position 110 with Gly. For example, the isolated variants of the present invention comprise or consist of an alteration of P110G.

In one embodiment, the isolated variant of the present invention comprises or consists of an alteration at position 111 (using SEQ ID NO:3 for numbering). In an embodiment the alteration is a substitution of the amino acid at position 111 with Phe. For example, the isolated variants of the present invention comprise or consist of an alteration of Y111F.

In one embodiment, the isolated variant of the present invention comprises or consists of an alteration at position 112 (using SEQ ID NO:3 for numbering). In an embodiment the alteration is a substitution of the amino acid at position 112 with Ser. For example, the isolated variants of the present invention comprise or consist of an alteration of G112S.

In one embodiment, the isolated variant of the present invention comprises or consists of an alteration at position 113 (using SEQ ID NO:3 for numbering). In an embodiment the alteration is a substitution of the amino acid at position 113 with Pro. For example, the isolated variants of the present invention comprise or consist of an alteration of A113P.

In one embodiment, the isolated variant of the present invention comprises or consists of an alteration at position 119 (using SEQ ID NO:3 for numbering). In an embodiment the alteration is a substitution of the amino acid at position 119 with Asn. For example, the isolated variants of the present invention comprise or consist of an alteration of S119N.

In one embodiment, the isolated variant of the present invention comprises or consists of an alteration at position 120 (using SEQ ID NO:3 for numbering). In an embodiment the alteration is a substitution of the amino acid at position 120 with Ala, Gln or Pro. For example, the isolated variants of the present invention comprise or consist of an alteration of H120A, H120Q or H120P.

In one embodiment, the isolated variant of the present invention comprises or consists of an alteration at position 121 (using SEQ ID NO:3 for numbering). In an embodiment the alteration is a substitution of the amino acid at position 121 with Ala. For example, the isolated variants of the present invention comprise or consist of an alteration of S121A.

In one embodiment, the isolated variant of the present invention comprises or consists of an alteration at position 122 (using SEQ ID NO:3 for numbering). In an embodiment the alteration is a substitution of the amino acid at position 122 with Ala. For example, the isolated variants of the present invention comprise or consist of an alteration of Q122A.

In one embodiment, the isolated variant of the present invention comprises or consists of an alteration at position 128 (using SEQ ID NO:3 for numbering). In an embodiment the alteration is a substitution of the amino acid at position 128 with Arg. For example, the isolated variants of the present invention comprise or consist of an alteration of H128R.

In one embodiment, the isolated variant of the present invention comprises or consists of an alteration at position 131 (using SEQ ID NO:3 for numbering). In an embodiment the alteration is a substitution of the amino acid at position 131 with Cys. For example, the isolated variants of the present invention comprise or consist of an alteration of V131C.

In one embodiment, the isolated variant of the present invention comprises or consists of an alteration at position 134 (using SEQ ID NO:3 for numbering). In an embodiment the alteration is a substitution of the amino acid at position 134 with Val. For example, the isolated variants of the present invention comprise or consist of an alteration of Y134V. The variant may also further comprise an alteration of G102G.

In one embodiment, the isolated variant of the present invention comprises or consists of an alteration at position 135 (using SEQ ID NO:3 for numbering). In an embodiment the alteration is a substitution of the amino acid at position 135 with Asn. For example, the isolated variants of the present invention comprise or consist of an alteration of H135N.

In one embodiment, the isolated variant of the present invention comprises or consists of an alteration at position 139 (using SEQ ID NO:3 for numbering). In an embodiment the alteration is a substitution of the amino acid at position 139 with Gly. For example, the isolated variants of the present invention comprise or consist of an alteration of S139G.

In one embodiment, the isolated variant of the present invention comprises or consists of an alteration at position 141 (using SEQ ID NO:3 for numbering). In an embodiment the alteration is a substitution of the amino acid at position 141 with Tyr. For example, the isolated variants of the present invention comprise or consist of an alteration of W141Y.

In one embodiment, the isolated variant of the present invention comprises or consists of an alteration at position 147 (using SEQ ID NO:3 for numbering). In an embodiment the alteration is a substitution of the amino acid at position 147 with Gly. For example, the isolated variants of the present invention comprise or consist of an alteration of T147G.

In one embodiment, the isolated variant of the present invention comprises or consists of an alteration at position 153 (using SEQ ID NO:3 for numbering). In an embodiment the alteration is a substitution of the amino acid at position 153 with Thr. For example, the isolated variants of the present invention comprise or consist of an alteration of R153T.

In one embodiment, the isolated variant of the present invention comprises or consists of an alteration at position 158 (using SEQ ID NO:3 for numbering). In an embodiment the alteration is a substitution of the amino acid at position 158 with Ser. For example, the isolated variants of the present invention comprise or consist of an alteration of A158S.

In one embodiment, the isolated variant of the present invention comprises or consists of an alteration at position 161 (using SEQ ID NO:3 for numbering). In an embodiment the alteration is a substitution of the amino acid at position 161 with Tyr. For example, the isolated variants of the present invention comprise or consist of an alteration of F161Y.

In one embodiment, the isolated variant of the present invention comprises or consists of an alteration at position 164 (using SEQ ID NO:3 for numbering). In an embodiment the alteration is a substitution of the amino acid at position 164 with Thr. For example, the isolated variants of the present invention comprise or consist of an alteration of K164T.

In one embodiment, the isolated variant of the present invention comprises or consists of an alteration at position 171 (using SEQ ID NO:3 for numbering). In an embodiment the alteration is a substitution of the amino acid at position 171 with Arg. For example, the isolated variants of the present invention comprise or consist of an alteration of A171R.

In one embodiment, the isolated variant of the present invention comprises or consists of an alteration at position 176 (using SEQ ID NO:3 for numbering). In an embodiment the alteration is a substitution of the amino acid at position 176 with Val. For example, the isolated variants of the present invention comprise or consist of an alteration of P176V.

In one embodiment, the isolated variant of the present invention comprises or consists of an alteration at position 178 (using SEQ ID NO:3 for numbering). In an embodiment the alteration is a substitution of the amino acid at position 178 with Gly. For example, the isolated variants of the present invention comprise or consist of an alteration of K178G.

In one embodiment, the isolated variant of the present invention comprises or consists of an alteration at position 183 (using SEQ ID NO:3 for numbering). In an embodiment the alteration is a substitution of the amino acid at position 183 with Gly. For example, the isolated variants of the present invention comprise or consist of an alteration of D183G.

In one embodiment, the isolated variant of the present invention comprises or consists of an alteration at position 185 (using SEQ ID NO:3 for numbering). In an embodiment the alteration is a substitution of the amino acid at position 185 with Pro. For example, the isolated variants of the present invention comprise or consist of an alteration of K185P.

In one embodiment, the isolated variant of the present invention comprises or consists of an alteration at position 186 (using SEQ ID NO:3 for numbering). In an embodiment the alteration is a substitution of the amino acid at position 186 with Tyr. For example, the isolated variants of the present invention comprise or consist of an alteration of T186Y.

In one embodiment, the isolated variant of the present invention comprises or consists of an alteration at position 193 (using SEQ ID NO:3 for numbering). In an embodiment the alteration is a substitution of the amino acid at position 193 with Ala. For example, the isolated variants of the present invention comprise or consist of an alteration of S193A.

In one embodiment, the isolated variant of the present invention comprises or consists of an alteration at position 195 (using SEQ ID NO:3 for numbering). In an embodiment the alteration is a substitution of the amino acid at position 195 with Ser. For example, the isolated variants of the present invention comprise or consist of an alteration of K195S.

In one embodiment, the isolated variant of the present invention comprises or consists of an alteration at position 196 (using SEQ ID NO:3 for numbering). In an embodiment the alteration is a substitution of the amino acid at position 196 with Gly. For example, the isolated variants of the present invention comprise or consist of an alteration of Y196G. The variant may further comprise an alteration of K197P.

In one embodiment, the isolated variant of the present invention comprises or consists of an alteration at position 197 (using SEQ ID NO:3 for numbering). In an embodiment the alteration is a substitution of the amino acid at position 197 with Pro. For example, the isolated variants of the present invention comprise or consist of an alteration of K197P. The variant may further comprise an alteration of Y196G.

In one embodiment, the isolated variant of the present invention comprises or consists of an alteration at position 198 (using SEQ ID NO:3 for numbering). In an embodiment the alteration is a substitution of the amino acid at position 198 with Asn or Phe. For example, the isolated variants of the present invention comprise or consist of an alteration of H198N or H198F.

In one embodiment, the isolated variant of the present invention comprise or consists of an alteration at position 203

(using SEQ ID NO:3 for numbering). In an embodiment the alteration is a substitution of the amino acid at position 203 with Asn. For example, the isolated variants of the present invention comprise or consist of an alteration of D203N.

In one embodiment, the isolated variants of the present invention comprises or consists of an alteration at position 206 (using SEQ ID NO:3 for numbering). In an embodiment the alteration is a substitution of the amino acid at position 19 with Ala or Ser. For example, the isolated variants of the present invention comprise or consist of an alteration of N206A or N206S.

In one embodiment, the isolated variants of the present invention comprises an amino acid sequence having a degree of amino acid sequence identity of at least 65%, at least 70%, at least 75%, at least 80%, at least 85%, at least 90%, at least 95%, at least 96%, at least 97%, at least 98%, or at least 99% to the amino acid sequence of a lysozyme belonging to family 25 of glycosyl hydrolases, preferably a fungal family 25 lysozyme.

In another embodiment, the isolated variants of the present invention comprise an amino acid sequence having a degree of amino acid sequence identity of at least 65%, at least 70%, at least 75%, at least 80%, at least 85%, at least 90%, at least 95%, at least 96%, at least 97%, at least 98%, or at least 99% to the amino acid sequence of a polypeptide corresponding to the mature peptide of SEQ ID NO:2.

In another embodiment, the variants comprise an amino acid sequence having a degree of amino acid sequence identity of at least 65%, at least 70%, at least 75%, at least 80%, at least 85%, at least 90%, at least 95%, at least 96%, at least 97%, at least 98%, or at least 99% to SEQ ID NO:3.

In another embodiment, the isolated variants of the present invention comprise an amino acid sequence of a polypeptide encoded by a polynucleotide that hybridizes under at least medium stringency conditions with (i) the mature polypeptide encoded by sequence of SEQ ID NO:1, (ii) the genomic DNA sequence comprising the mature polypeptide coding sequence of SEQ ID NO:1, or (iii) a full-length complementary strand of (i) or (ii).

In another embodiment, the isolated variants of the present invention comprise a polypeptide encoded by a polynucleotide comprising a nucleotide sequence having at least 65%, at least 70%, at least 75%, at least 80%, at least 85%, at least 90%, at least 95%, at least 96%, at least 97%, at least 98%, at least 99% or 100% identity with the mature polypeptide coding sequence of SEQ ID NO:1.

In an embodiment, the isolated variants further comprise aspartic acid at position 105 and glutamic acid at position 107 (using SEQ ID NO:3 for numbering). In another embodiment, the isolated variants further comprise aspartic acid at position 16, glutamine at position 191, tyrosine at position 145, tyrosine at position 69, aspartic acid at position 201, glycine at position 200, glycine at position 44, glycine at position 67, glycine at position 14 and/or histidine at position 70 (using SEQ ID NO:3 numbering).

In an embodiment, the present invention provides lysozyme variants having altered properties relative to the parent lysozyme. In one embodiment, the lysozyme variant has improved pH stability and/or activity at alkaline pH conditions (such as from pH 7.5 to 12, preferably from 8 to 11, more preferably from 8.5 to 10, even more preferably from 9 to 9.5), as compared to the parent lysozyme. Accordingly, the present invention provides a variant of a parent lysozyme, wherein the variant comprises or consists of an alteration at one or more positions selected from the group consisting of position number 102, 134, 108, 196, 197, 198, 56, 19, 120, 20, 135, and/or 203 (using SEQ ID NO:3 for numbering), and wherein the variant has increased stability and/or activity at alkaline pH as compared to the parent lysozyme. The following lysozyme variants are constructed to have improved pH stability and/or activity at an alkaline pH conditions (such as pH from pH 7.5 to 12, preferably from 8 to 11, more preferably from 8.5 to 10, even more preferably from 9 to 9.5) compared to the parent enzyme (using SEQ ID NO:3 for numbering):

| | |
|---|---|
| G102P; | Y134V; |
| G102P; | T108W; |
| T196G; | K197G; |
| Y196G; | K197P; |
| Y56W; | N19D; |
| H120Q; | H198N; |
| H198F; | H20W; |
| H20Y; and/or | H135N. |

The following combination of alterations is constructed to have improved pH stability and/or activity at alkaline pH conditions (from pH 7.5 to 12, preferably from 8 to 11, more preferably from 8.5 to 10, even more preferably from 9 to 9.5) compared to the parent enzyme (using SEQ ID NO:3 for numbering): G102P and Y134V and/or Y196G and K197P.

In one embodiment, the lysozyme variant has improved activity at alkaline pH conditions (such as, from pH 7.5 to 12, preferably from 8 to 11, more preferably from 8.5 to 10, even more preferably from 9 to 9.5), as compared to the parent lysozyme. An example of a lysozyme variant constructed to have improved activity at an alkaline pH (such as pH from pH 7.5 to 12, preferably from 8 to 11, more preferably from 8.5 to 10, even more preferably from 9 to 9.5) compared to the parent enzyme is D203N (using SEQ ID NO:3 for numbering).

In one embodiment, the lysozyme variant has improved pH stability at acidic pH conditions (such as, from pH 2 to 5.5, preferably from 2.5 to 5.25, more preferably from 3 to 5, even more preferably from 3.5 to 4), as compared to the parent lysozyme. Accordingly, the present invention provides a variant of a patent lysozyme, wherein the variant comprises or consists of an alteration at one or more positions selected from the group consisting of position number 161, 128, 131, 95, 203, 98, 112, 55, 32, 89, and/or 206 (using SEQ ID NO:3 for numbering), and wherein the variant has increased activity at acidic pH conditions as compared to the parent lysozyme. The following lysozyme variants are constructed to have improved pH stability at an acidic pH (such as from pH 2 to 5.5, preferably from 2.5 to 5.25, more preferably from 3 to 5, even more preferably from 3.5 to 4) compared to the parent enzyme (using SEQ ID NO:3 for numbering):

| | |
|---|---|
| F161Y; | H128R; |
| V131C; | D95G; |
| D203N; | R98G; |
| G112S; | H55N; |
| D32S; | N89T; |
| N206A; and/or | N206S. |

In one embodiment, the lysozyme variant has improved stability under conditions of acidic pH (such as, from pH 2 to 5.5, preferably from 2.5 to 5.25, more preferably from 3 to 5, even more preferably from 3.5 to 4), and in the presence of gastric proteases as compared to the parent lysozyme. In this connection gastric proteases is intended to mean proteases excreted by the organism into the gastrointestinal tract during digestion, such as trypsin, chymotrypsin and pepsin; or externally added proteases, such as proteases added to the feed e.g.

the commercially available protease sold under the name of ProAct© (Novozymes A/S), or any mixtures thereof. Accordingly, the present invention provides a variant of a patent lysozyme, wherein the variant comprises or consists of an alteration at one or more positions selected from the group consisting of position number 56, 131 and/or 161 (using SEQ ID NO:3 for numbering), and wherein the variant has increased stability at acidic pH conditions in the presence of one or more gastric proteases compared to the parent lysozyme. The lysozyme variants constructed to have improved stability at an acidic pH (such as from 2 to 5.5, preferably from 2.5 to 5.25, more preferably from 3 to 5, even more preferably from 3.5 to 4) in the presence of one or more gastric proteases (such as trypsin, chymotrypsin, pepsin and any mixtures thereof) compared to the parent enzyme includes variants comprising following substitutions (using SEQ ID NO:3 for numbering):

| | |
|---|---|
| Y56W; | V131C and/or |
| F161C. | |

In one embodiment, the lysozyme variant has improved activity at low temperatures (e.g. from 0° C. to 20° C., preferably from 2° C. to 18° C., preferably from 5° C. to 15° C., more preferably from 8° C. to 12° C., even most preferably from 10° C. to 15° C.) or moderate temperatures (e.g. from 15° C. to 45° C., preferably from 20° C. to 40° C., preferably from 22° C. to 35° C., most preferably from 25° C. to 30° C.,), as compared to the parent lysozyme. Accordingly, the present invention provides a variant of a parent lysozyme, wherein the variant comprises or consists of an alteration at one or more positions selected from the group consisting of position number 47, 111, 108, 45, 22, 110, 120, 147, 196, 49, 55 and/or 193, and wherein the variant has improved activity at a low temperature as compared to the parent lysozyme. The following variants are constructed to have improved activity at low temperatures (e.g. from 0° C. to 20° C., preferably from 2° C. to 18° C., preferably from 5° C. to 15° C., more preferably from 8° C. to 12° C., even most preferably from 10° C. to 15° C.) or moderate temperatures (e.g. from 15° C. to 45° C., preferably from 20° C. to 40° C., preferably from 22° C. to 35° C., most preferably from 25° C. to 30° C.), as compared to the parent lysozyme (using SEQ ID NO:3 for numbering):

| | |
|---|---|
| Y47F; | Y111F; |
| Y108F; | T45G; |
| K22G; | P110G; |
| H120A; | T147G; |
| Y196G; | D49A; |
| H55A; and/or | S193A. |

In one embodiment, the lysozyme variant has improved thermostability (such as, a temperature from 45° C. to 110° C., preferably from 50° C. to 100° C., more preferably from 60° C. to 90° C., even more preferably from 70° C. to 80° C.,), as compared to the parent lysozyme. Accordingly, the present invention provides a variant of a parent lysozyme, wherein the variant comprises or consists of an alteration at one or more positions selected from the group consisting of position number 121, 120, 185, 186, 176, 113, 122, 119, 35, 65, 139, 141, 153, 158, 171, 195, 76, 164, 30, 85, 178, 183, 186, 112, and/or 197 and wherein the variant has improved thermostability as compared to the parent lysozyme. The following variants are constructed to have improved thermostability (such as, a temperature from 45° C. to 110° C., preferably from 50° C. to 100° C., more preferably from 60° C. to 90° C., even more preferably from 70° C. to 80° C.), as compared to the parent lysozyme (using SEQ ID NO:3 for numbering):

| | |
|---|---|
| S121A; | H120P; |
| T186T; | A113P; |
| K185P; | P176V; |
| Q122A; | S119N; |
| Q35R; | L65I; |
| S139G; | W141Y; |
| R153T; | A158S; |
| A171R; | K195S; |
| K76S; | K164T; |
| K30Y; | F85Y; |
| K178C; | D183G; |
| Y186Y; | G112S; and/or |
| K197P. | |

Preferred variants having improved thermostability compared to the parent lysozyme include variants comprising following substitutions (Using SEQ ID NO: for numbering):

| | |
|---|---|
| N19D; | H20Y; |
| K22G; | T45G; |
| Y47F; | D49G; |
| H55A; | R98G; |
| A158S and/or | K164T. |

The variants comprising alterations at one or more of the above identified positions have an increased stability in detergent, preferably in liquid detergent as compared to the parent lysozyme.

The lysosyme variants of the present invention have antimicrobial activity and/or lysozyme activity. Lysozyme variants which are not capable of catalyzing the hydrolysis of 1,4-beta-linkages between N-acetylmuramic acid and N-acetyl-D-glucosamine residues in a peptidoglycan and between N-acetyl-D-glucosamine residues in chitodextrins may still have an antimicrobial effect since such inactive lysozyme variants can bind to the surface of the microorganism and potentially inhibit its growth. Such lysozyme variants may also be termed "bacteriostatics".

It is understood that the embodiment described above can be combined if desired, especially that the indicated positions and specific substitutions may be combined with the sequence identities of the variants.

Polynucleotides

The present invention also relates to isolated polynucleotides that encode variants of a parent lysozyme according to the present invention. In particular polynucleotides that encode a lysozyme variant as described in the variant section above, is encompassed by the present invention. Polynucleotides of the invention will hybridize to a denatured double-stranded DNA probe comprising either the full variant sequence corresponding to positions 1 to 705 of SEQ ID NO:1 or position 51 to 705 of SEQ ID NO:1 or 75 to 705 of SEQ ID NO:1 with proper sequence alterations corresponding to actual amino acid alterations in the variant or any probe comprising a variant subsequence thereof having a length of at least about 100 base pairs under at least medium stringency conditions, but preferably at high stringency conditions. The variant polynucleotides of the present invention may also comprise silent mutations in addition to the mutations giving rise to the amino acid alterations described in the variant section above. Silent mutations are mutations in the three-letter code which do not give rise to a change in the amino acid, e.g. GTT to GAT, which both code for valine.

The polynucleotides encoding the lysozyme variants of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having antimicrobial and/or lysozyme activity of the invention are then identified and isolated by, for example, hybridization or PCR.

Expression Vectors

The present invention also relates to expression vectors, in particular recombinant expression vectors, comprising a nucleic acid construct of the invention. Nucleic acid constructs of the invention comprise an isolated polynucleotide encoding a variant lysozyme of the present invention, preferably operably linked to one or more control sequences which direct the expression of the coding sequence in a suitable host cell under conditions compatible with the control sequences. In creating the expression vector, the coding sequence is located in the vector so that the coding sequence is operably linked with the appropriate control sequences for expression. The control sequences may either be provided by the vector or by the nucleic acid construct inserted into the vector.

The control sequence may be an appropriate promoter sequence, a nucleotide sequence which is recognized by a host cell for expression of a polynucleotide encoding a polypeptide of the present invention. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell. Such promoters are well known in the art. The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention; such terminators are well known in the art. The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention, such leader sequences are well known in the art. The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention. The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention. It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound.

An isolated polynucleotide encoding a variant lysozyme of the present invention may be manipulated in a variety of ways to provide for expression of the polypeptide. Manipulation of the polynucleotide sequence prior to insertion into a vector may be desirable or necessary depending on the expression vector. The techniques for modifying polynucleotide sequences utilizing recombinant DNA methods are well known in the art. Furthermore, tags which may aid purification or immobilization of the polypeptide may be added to the polypeptide. Such a tag may for example be a polyhistidine tag (His tag). Preferably, the tag located in the N-terminal or C-terminal of the polypeptide, and may be encoded by the vector. Alternatively, the tag may be located internally in the polypeptide, as long as it does not affect the functionality of the polypeptide.

The recombinant expression vector may be any vector (e.g. a plasmid, phagemid, phage or virus) that can be conveniently subjected to recombinant DNA procedures and can bring about the expression of the nucleotide sequence. The choice of the vector will typically depend on the compatibility of the vector with the host cell into which the vector is to be introduced.

The vectors may be linear or closed circular plasmids. The vector may be an autonomously replicating vector, i.e. a vector that exists as an extrachromosomal entity, the replication of which is independent of chromosomal replication, e.g. a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus lichenifonnis*, or markers that confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention may contain an element(s) that permits stable integration of the vector into the host cell's genome or autonomous replication of the vector in the cell independent of the genome.

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see for example Sambrook et al. (1989) supra).

In one embodiment of the present invention the plasmid vector may contain the following elements:
i) a signal peptide coding region (e.g. obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA), followed by a polynucleotide sequence encoding the mature lysozyme variant. This sequence may be preceded by and operably linked to:
ii) a DNA sequence comprising a mRNA stabilising segment (e.g. derived from the CryIIIa gene, as shown in WO 99/043835);
iii) a marker gene (e.g. a chloramphenicol resistance gene); and
iv) genomic DNA from *Bacillus subtilis* as 5' and 3' flanking segments upstream and downstream of the polynucleotide, respectively, to enable genomic integration by homologous recombination between the flanking segments and the *Bacillus* genome. The vectors described above may also be useful in the generation and screening of the variants using the previously described mutagenesis procedures.

Host Cells

The present invention also relates to a recombinant host cell comprising a polynucleotide encoding a variant lysozyme of the invention, which is advantageously used in the recombinant production of the polypeptides. A vector comprising a polynucleotide sequence of the present invention is introduced into a host cell so that the vector is maintained as a chromosomal integrant or as a self-replicating extra-chromosomal vector as described earlier.

The host cell may be a prokaryote such as bacterial cells, an archaea or a eukaryote such as fungal cells, plant cells, insect cells, or mammalian cells.

Useful prokaryotes are bacterial cells such as gram positive bacteria including, but not limited to, a *Bacillus* cell, e.g. *Bacillus alkalophilus*, *Bacillus amyloliquefaciens*, *Bacillus brevis*, *Bacillus circulans*, *Bacillus clausii*, *Bacillus coagulans*, *Bacillus halodurans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see for example Chang and Cohen (1979) *Molecular General Genetics* 168:111-115), using competent cells (see for example Young and Spizizin (1961) *Journal of Bacteriology* 81:823-829; or Dubnau and Davidoff-Abelson (1971) *Journal of Molecular Biology* 56:209-221), electroporation (see for example Shigekawa and Dower (1988) *Biotechniques* 6:742-751), or conjugation (see for example Koehler and Thorne (1987) *Journal of Bacteriology* 169:5771-5278).

In a preferred embodiment, the host cell is a fungal cell. "Fungi" as used herein includes the phyla Ascomycota, Basidiomycota, Chytridiomycota, and Zygomycota (as defined by Hawksworth et al. (1995) *Ainsworth and Bisby's Dictionary of The Fungi* (8th edition), CAB International, University Press, Cambridge, UK) as well as the Oomycota (as cited in Hawksworth et al. (1995) *Ainsworth and Bisby's Dictionary of The Fungi* (8th edition), CAB International, University Press, Cambridge, UK, page 171) and all mitosporic fungi (Hawksworth et al. (1995) *Ainsworth and Bisby's Dictionary of The Fungi* (8th edition), CAB International, University Press, Cambridge, UK). In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport (eds) (1980) *Soc. App. Bacteriol. Symposium Series* No. 9).

In an even more preferred embodiment, the yeast host cell is a *Candida*, *Hansenula*, *Kluyveromyces*, *Pichia*, *Saccharomyces*, *Schizosaccharomyces*, or *Yarrowia* cell. In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. Filamentous fungi include all filamentous forms of the subdivision Eumycota and Oomycota (as defined by Hawksworth et al. (1995) *Ainsworth and Bisby's Dictionary of The Fungi* (8th edition), CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. In contrast, vegetative growth by yeasts such as *Saccharomyces cerevisiae* is by budding of a unicellular thallus and carbon catabolism may be fermentative. In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*. In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium*

*roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (*Nirenberg* sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238023 and Yelton et al. (1984) *Proceedings of the National Academy of Sciences USA* 81:1470-1474. Suitable methods for transforming *Fusarium* species are described by Malardier et al. (1989) *Gene* 78:147-156 and WO 96/00787. Yeast may be transformed using the procedures described by Becker and Guarente, Abelson and Simon (editors) Guide to Yeast Genetics and Molecular *Biology, Methods in Enzymology* 194:182-187, Academic Press, Inc., New York; Ito et al. (1983) *Journal of Bacteriology* 153:163; and Hinnen et al. (1978) *Proceedings of the National Academy of Sciences USA* 75:1920.

A particular embodiment of the present invention is a recombinant host cell transformed with a polynucleotide encoding a variant lysozyme of the present invention. Preferably, such a host cell does not contain an inherent lysozyme encoding gene, or such a gene has been disrupted. Thereby the recombinant variant lysozyme is the only lysozyme produced by the recombinant host cell of the present invention.

Methods of Production

The present invention also relates to methods of producing a lysozyme variant, comprising: (a) cultivating a host cell of the present invention under conditions suitable for the expression of the variant; and (b) recovering the variant from the cultivation medium.

In the production methods of the present invention, the host cells are cultivated in a nutrient medium suitable for production of the lysozyme variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the polypeptide is secreted into the nutrient medium, the polypeptide can be recovered directly from the medium. If the polypeptide is not secreted, it can be recovered from cell lysates.

One embodiment of the present invention is a method of producing a variant of a parent lysozyme, wherein said variant has antimicrobial and/or lysozyme activity, said method comprising: a) culturing a cell under conditions suitable for expression of the variant, where said cell contains a polynucleotide sequence encoding a variant of a parent lysozyme in which said variant is altered in one or more (several) amino acid position(s) selected from the group consisting of positions: 47, 111, 108, 45, 22, 110, 120, 147, 196, 49, 55, 193 161, 128, 131, 95, 203, 98, 112, 55, 32, 89, 206 121, 120, 185, 186, 176, 113, 122, 119, 35, 65, 139, 141, 153, 158, 171, 195, 76, 164, 30, 85, 178, 183, 186, 112, 174, 187, 197, 102, 134, 108, 196, 197, 198, 56, 19, 120, 20, 135, and 203, and said polynucleotide sequence is prepared by mutagenesis of a parent polynucleotide sequence of SEQ ID NO:1, or a parent polynucleotide sequence having at least 65%, more preferably at least 70%, more preferably at least 75%, more preferably at least 80%, more preferably at least 85%, even more preferably at least 90%, most preferably at least 95% identity to the nucleotide sequence of SEQ ID NO:1; and b) recovering the lysozyme variant from the cultivation medium. In an alternative aspect, the lysozyme variant is not recovered, but rather a host cell of the present invention expressing a variant is used as a source of the variant.

The lysozyme variant may be detected using methods known in the art that are specific for the expressed polypeptides. These detection methods may include use of specific antibodies, formation of an enzyme product, or disappearance of an enzyme substrate. For example, an enzyme assay may be used to determine the activity of the variant lysozyme as described herein in the Examples.

The resulting lysozyme variant may be recovered by methods known in the art. For example, the polypeptide may be recovered from the nutrient medium by conventional procedures including, but not limited to, collection, centrifugation, filtration, extraction, spray-drying, evaporation, or precipitation.

A lysozyme variant of the present invention may be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction (see e.g. J.-C. Janson and Lars Ryden (editors) (1989) *Protein Purification* VCH Publishers, New York) to obtain substantially pure lysozyme variants.

Compositions

The present invention also relates to compositions comprising a variant lysozyme or a polypeptide having antimicrobial and/or lysozyme activity of the present invention and a carrier and/or an exhibient. Preferably, the compositions are enriched in such a variant or polypeptide. The term "enriched" indicates that the antimicrobial and/or lysozyme activity of the composition has been increased, e.g. with an enrichment factor of 1.1 or more. Preferably, the compositions are formulated to provide desirable characteristics such as low color, low odor and acceptable storage stability.

The composition may comprise a variant or polypeptide of the present invention as the major enzymatic component, e.g. a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The polypeptide compositions may be prepared in accordance with methods known in the art and may be in the form of a liquid, paste, gel or a dry formulation. For instance, the polypeptide may be formulated in the form of a granulate or a microgranulate. The variant or polypeptide to be included in the composition may be stabilized in accordance with methods known in the art. In a preferred embodiment the variant lysozyme is formulated in a liquid composition.

A preferred embodiment of the present invention is a feed composition comprising a lysozyme variant of the present invention. In particular a variant with improved stability at acidic pH and/or increased protease stability is preferred.

Detergent Compositions

The present invention also encompasses detergent compositions comprising a lysozyme variant of the present invention. In particular a variant with improved stability and/or activity at alkaline pH and/or a variant with improved activity at low or moderate temperature is preferred. The detergent composition may be adapted for specific uses such laundry, in particular household laundry, dish washing or hard surface cleaning.

The detergent composition typically comprises conventional detergent ingredients such as surfactants, builders, bleaches, enzymes and other ingredients.

In a preferred embodiment the detergent composition comprises a lysozyme and a protease.

The detergent composition can be in any form, such as a solid, liquid, paste, gel or any combination thereof. The composition may be in the form of a tablet, bar or pouch, including multi-compartment pouches. The composition can be in the form of a powder, for example a free-flowing powder, such as an agglomerate, spray-dried powder, encapsulate, extrudate, needle, noodle, flake, or any combination thereof.

Enzymes

In one aspect, the present invention provides a detergent additive comprising a lysozyme variant of the present invention. The detergent additive as well as the detergent composition may comprise one or more enzymes such as a protease, lipase, cutinase, amylase, carbohydrase, cellulase, pectinase, mannanase, arabinase, galactanase, xylanase, oxidase, e.g. a laccase, and/or peroxidase.

In general the properties of the selected enzyme(s) should be compatible with the selected detergent (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may for example be a metalloprotease (EC 3.4.17 or EC 3.4.24) or a serine protease (EC 3.4.21), preferably an alkaline microbial protease or a trypsin-like protease. Examples of alkaline proteases are subtilisins (EC 3.4.21.62), especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase®, Savinase®, Primase®, Duralase®, Esperase®, and Kannase® (Novozymes A/S), Maxatase®, Maxacal®, Maxapem®, Properase®, Purafect®, Purafect OxP®, FN2™, and FN3™ (Genencor International Inc.).

Protease enzymes may be incorporated into detergent compositions in accordance with the invention at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition Lipases: Suitable lipases include those of bacterial or fungal origin. Chemically or genetically modified mutants of such lipases are included in this connection. The lipase may for example be triacylglycerol lipase (EC3.1.1.3), phospholipase A2 (EC 3.1.1.4), Lysophospholipase (EC 3.1.1.5), Monoglyceride lipase (EC 3.1.1.23), galactolipase (EC 3.1.1.26), phospholipase A1 (EC 3.1.1.32), Lipoprotein lipase (EC 3.1.1.34). Examples of useful lipases include a Humicola lanuginosa lipase, e.g. as described in EP 258 068 and EP 305 216; a Rhizomucor miehei lipase, e.g. as described in EP 238 023 or from H. insolens as described in WO 96/13580; a Candida lipase, such as a C. antarctica lipase, e.g. the C. antarctica lipase A or B described in EP 214 761; a Pseudomonas lipase, such as one of those described in EP 721 981 (e.g. a lipase obtainable from a Pseudomonas sp. SD705 strain having deposit accession number FERM BP-4772), in PCT/JP96/00426, in PCT/JP96/00454 (e.g. a P. solanacearum lipase), in EP 571 982 or in WO 95/14783 (e.g. a P. mendocina lipase), a P. alcaligenes or P. pseudoalcaligenes lipase, e.g. as described in EP 218 272, a P. cepacia lipase, e.g. as described in EP 331 376, a P. stutzeri lipase, e.g. as disclosed in GB 1,372,034, or a P. fluorescens lipase; a Bacillus lipase, e.g. a B. subtilis lipase (Dartois et al. (1993) Biochemica et Biophysica Acta 1131:253-260), a B. stearothermophilus lipase (JP 64/744992) and a B. pumilus lipase (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. A preferred lipase variant is that of Humicola lanuginosa DSM 4109 as described in WO 00/60063. Especially preferred are the variants disclosed in the Example in WO 00/60063 with improved first wash performance., i.e., T231R+N233R; G91A+D96W+E99K+G263Q+L264A+I265T+G266D+T267A+L269N+R209P+T231R+N233R; N33Q+D96S+T231R+N233R+Q249R; E99N+N101S+T231R+N233R+Q249R; E99N+N101S+T231R+N233R+Q249R.

Suitable commercially available lipases include Lipex®, Lipolase® and Lipolase Ultra®, Lipolex®, Lipoclean® (available from Novozymes A/S), M1 Lipase™ and Lipomax™ (available from Genencor Inc.) and Lipase P "Amano" (available from Amano Pharmaceutical Co. Ltd.). Commercially available cutinases include Lumafast™ from Genencor Inc.

The lipases are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition.

Cutinases: Potentially useful types of cutinases include (EC 3.1.1.74), e.g. a cutinase derived from Pseudomonas mendocina as described in WO 88/09367, or a cutinase derived from Fusarium solani pisi (described e.g. in WO 90/09446). Due to the lipolytic activity of cutinases they may be effective against the same stains as lipases. Commercially available cutinases include Lumafast™ from Genencor Inc.

The cutinases are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition.

Carbohydrases: Carbohydrases covers glycoside hydrolases (EC 3.2.1.-) and polysaccharide lyases (EC 4.2.2.-). Glycoside hydrolases catalyze the hydrolysis of the glycosidic bond between two or more carbohydrates or between a carbohydrate and a non-carbohydrate moiety. Polysaccharide lyases catalyze the cleavage of polysaccharide chains by a beta elimination mechanism resulting in a double bond of the newly formed reducing end. Carbohydrases include for example amylases, hemicellulases, pectinases and cellulases described in more detail below. Other carbohydrases may be xanthanases or pullulanases.

Suitable xanthanases include those of bacterial or fungal origin. Chemically or genetically modified mutants are included. Sources of xanthanases are for example described in Cadmus et al. (1988) *J of Industrial Microbiology and Biotechnology* 4:127-133; EP0030393; and Hashimoto et al. (1998) *Appl Environ Microbiol.* 64:3765-3768.

Suitable pullulanases include those of bacterial or fungal origin. Chemically or genetically modified mutants are included. Sources of pullulanase are for example Dextrozyme® and Promozyme® D2 (Novozymes A/S).

Amylases: Amylases comprise e.g. alpha-amylases (EC 3.2.1.1), beta-amylases (EC 3.2.1.2) and/or glucoamylases (EC 3.2.1.3) of bacterial or fungal origin. Chemically or genetically modified mutants of such amylases are included in this connection. Alpha-amylases are preferred in relation to the present invention. Relevant alpha-amylases include, for example, α-amylases obtainable from *Bacillus* species, in particular a special strain of *B. licheniformis*, described in more detail in GB 1296839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Further examples of useful amylases are the alpha-amylases derived from *Bacillus* sp. strains NCIB 12289, NCIB 12512, NCIB 12513 and DSM 9375; the alpha-amylases shown in SEQ ID NO 1 and 2 of WO 95/26397 (hereby incorporated by reference); the AA560 alpha-amylase derived from *Bacillus* sp. DSM 12649 disclosed as SEQ ID NO:2 in WO 00/60060 (hereby incorporated by reference); and the variants of the AA560 alpha-amylase, including the AA560 variant disclosed in Examples 7 and 8 (hereby incorporated by reference).

Relevant commercially available amylases include Natalase®, Stainzyme®, Duramyl®, Termamyl®, Termamyl™ Ultra, Fungamyl® and BAN® (all available from Novozymes A/S, Bagsvaerd, Denmark), and Rapidase® and Maxamyl® P (available from DSM, Holland) and Purastar®, Purastar OxAm and Powerase™ (available from Danisco A/S).

Other useful amylases are CGTases (cyclodextrin glucanotransferases, EC 2.4.1.19), e.g. those obtainable from species of *Bacillus, Thermoanaerobactor* or *Thermoanaerobacterium*.

The amylases are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition.

Hemicellulases: Suitable hemicellulases include enzymes with xylanolytiactivity, arabinolytic activity, galactolytic activity and/or mannolytic activity. The hemi-cellulases of the present invention may for example be selected from xylanases (EC 3.2.1.8, EC 3.2.1.32, and EC 3.2.1.136), xyloglucanases (EC 3.2.1.4 and EC 3.2.1.151), arabinofuranosidases (EC 3.2.1.55), acetylxylan esterases (EC EC 3.1.1.72), glucuronidases (EC 3.2.1.31, EC 3.2.1.56, 3.2.1.128 and 3.2.1.139), glucanohydrolase (EC 3.2.1.11, EC 3.2.1.83 and EC 3.2.1.73), ferulic acid esterases (EC 3.1.1.73), coumaric acid esterases (EC 3.1.1.73), mannanases (EC 3.2.1.25; EC 3.2.1.78 and EC 3.2.1.101), arabinosidase (EC 3.2.1.88), arabinanases (EC 3.2.1.99), galactanases (EC 3.2.1.89, EC 3.2.1.23 and 3.2.1.164) and lichenases (EC 3.2.1.73). This is, however, not to be considered as an exhausting list.

Mannananase is a preferred hemicellulase in relation to the present invention. Suitable mannanases include those of bacterial or fungal origin. Chemically or genetically modified mutants are included. In a preferred embodiment the mannanase is derived from a strain of the genus *Bacillus*, especially *Bacillus* sp. 1633 disclosed in positions 31-330 of SEQ ID NO:2 or in SEQ ID NO:5 of WO 99/64619 (hereby incorporated by reference) or *Bacillus agaradhaerens*, for example from the type strain DSM 8721. A suitable commercially available mannanase is Mannaway® produced by Novozymes A/S or Purabrite™ produced by Genencor a Danisco division.

Xylanase is a preferred hemicellulase in relation to the present invention. A suitable commercially available xylanase is Pulpzyme® HC (available from Novozymes A/S).

The hemicellulases are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition.

Pectinases: Suitable pectinolytic enzymes include those described in WO 99/27083, WO 99/27084, WO 00/55309 and WO 02/092741.

Suitable pectate lyases include those of bacterial or fungal origin. Chemically or genetically modified mutants are included. In a preferred embodiment the pectate lyase is derived from a strain of the genus *Bacillus*, especially a strain of *Bacillus subtilis*, especially *Bacillus subtilis* DSM14218 disclosed in SEQ ID NO:2 or a variant thereof disclosed in Example 6 of WO 02/092741 (hereby incorporated by reference) or a variant disclosed in WO 03/095638 (hereby incorporated by reference). Alternatively the pectate lyase is derived from a strain of *Bacillus licheniformis*, especially the pectate lyases disclosed as SEQ ID NO:8 in WO 99/27083 (hereby incorporated by reference) or variants thereof as described in WO 02/06442.

Suitable commercially available pectate lyases are Pectaway® or Pectawash® produced by Novozymes A/S.

The pectinolytic enzymes are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition.

Cellulases: Suitable cellulases include complete cellulases or mono-component endoglucanases of bacterial or fungal origin. Chemically or genetically modified mutants are included. The cellulase may for example be a mono-component or a mixture of mono-component endo-1,4-beta-glucanase often just termed "endoglucanases" (EC 3.2.1.4). Some xyloglucanases may also have endoglucanases activity and are also considered as suitable cellulases in the present invention. Suitable cellulases are disclosed in U.S. Pat. No. 4,435,307, which discloses fungal cellulases produced from *Humicola insolens*. Especially suitable cellulases are the cellulases having textile care benefits. Examples of such cellulases are cellulases described in European patent application No. 0 495 257.

Suitable mono-component endoglucanases may be obtained from one or more of the following species *Exidia glandulosa, Crinipellis scabella, Fomes fomentarius, Spongipellis* sp., *Rhizophlyctis rosea, Rhizomucor pusillus, Phycomyces nitens,* and *Chaetostylum fresenii, Diplodia gossypina, Microsphaeropsis* sp., *Ulospora bilgramii, Aureobasidium* sp., *Macrophomina phaseolina, Ascobolus stictoides, Saccobolus dilutellus, Peziza, Penicillium verruculosum, Penicillium chrysogenum,* and *Thermomyces verrucosus, Trichoderma reesei* aka *Hypocrea jecorina, Diaporthe syngenesia, Colletotrichum lagenarium, Xylaria hypoxylon, Nigrospora* sp., *Nodulisporum* sp., and *Poronia punctata, Cylindrocarpon* sp., *Nectria pinea, Volutella colletotrichoides, Sordaria fimicola, Sordaria macrospora, Thielavia thermophila, Syspastospora boninensis, Cladorrhinum foecundissimum, Chaetomium murorum, Chaetomium virescens, Chaetomium brasiliensis, Chaetomium cunicolorum, Myceliophthora thermophila, Gliocladium catenulatum, Scytalidium thermophila, Acremonium* sp *Fusarium solani, Fusarium anguioides, Fusarium poae, Fusarium oxysporum* ssp. *lycopersici, Fusarium oxysporum* ssp. *passiflora, Humicola nigrescens, Humicola grisea, Fusarium oxysporum, Thielavia terrestris* or *Humicola insolens*. One preferred endoglucanase is disclosed in WO 96/29397 as SEQ ID NO:9 (hereby incorporated by reference) or an enzyme with at least 70% identity thereto and variants thereof as disclosed in Example 1 of WO 98/12307. Another preferred endoglucanase is disclosed in WO 91/017243 (SEQ ID NO:2) or endoglucanases variants as disclosed in WO 94/007998.

Endoglucanases with an anti-redeposition effect may be obtained from fungal endoglucanases lacking a carbohydrate-binding module (CBM) from a number of bacterial sources. Some sources are *Humicola insolens, Bacillus* sp. deposited as DSM 12648, *Bacillus* sp. KSMS237 deposited as FERM P-16067, *Panibacillus polymyxa*, and *Panibacillus pabuli*. Specific anti-redeposition endoglucanase are disclosed in WO 91/17244 (FIG. 14) (hereby incorporated by reference), WO 04/053039 (SEQ ID NO:2) (hereby incorporated by reference), JP 2000210081 (position 1 to 824 of SEQ ID NO:1) (hereby incorporated by reference).

Xyloglucanases with an anti-redeposition effect may be obtained from a number of bacterial sources. Some sources are *Bacillus licheniformis, Bacillus* agaradhaerens (WO 99/02663), *Panibacillus polymyxa*, and *Panibacillus pabuli* (WO01/62903). Suitable variants of xyloglucasnes are also described in PCT/EP2009/056875. A commercially available xyloglucanase is Whitezyme® (Novozymes A/S).

Commercially available cellulases include Celluclas® produced from *Trichoderma reesei*, Celluzyme® produced from *Humicola insolens*. Commercially available endoglucanases are Carezyme®, Renozyme®, Endolase® and Celluclean® (Novozymes A/S), and KAC-500(B)™ (Kao Corporation) and Clazinase™, Puradax™ EG L and Puradax HA (Danisco A/S).

Cellulases are normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.5% of enzyme protein by weight of the composition, even more preferably at a level of from 0.001% to 0.2% of enzyme protein by weight of the composition.

Peroxidases/Oxidases: Suitable peroxidases/oxidases include those of plant, bacterial or fungal origin. Chemically modified or protein engineered mutants are included. Examples of useful oxidases are laccases (EC 1.10.3.2). Examples of useful peroxidases include catalases (EC 1.11.1.6) and peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

Arylesterases: Suitable arylesterases include those of plant, bacterial or fungal origin. Chemically modified or protein engineered mutants are included. Examples of useful arylesterase are for example obtained from *M. Smegmatis* as described in WO 05/056782.

Surfactants

Typically, the detergent composition comprises (by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branced-chain, linear-chain and random chain alkyl sulfates or fatty alcohol sulfates or primary alcohol sulfates or alkyl benzenesulfonates such as LAS and LAB or phenylalknesulfonates or alkenyl sulfonates or alkenyl benzenesulfonates or alkyl ethoxysulfates or fatty alcohol ether sulfates or alpha-olefin sulfonate or dodecenyl/tetradecnylsuccinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylaes, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/l to 10 g/l detergent composition. Many suitable surface active compounds are available and fully described in the literature, for example, in "Surface-Active Agents and Detergents", Volumes 1 and 11, by Schwartz, Perry and Berch.

Builders

The main role of a builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and buffer the pH of the wash water to a level of 9.5 to 11. The buffering capacity is also termed "reserve alkalinity", and should preferably be greater than 4.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. Builders include, but are not limited to, the alkali metal, ammonium and alkanolammonium salts of polyphosphates (e.g. tripolyphosphate STPP), alkali metal silicates, alkaline earth and alkali metal carbonates, aluminosilicate builders (e.g. zeolite) and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA may also contribute to the buffering capacity in liquid detergents.

Bleaches

The detergent compositions of the present invention may comprise one or more bleaching agents. In particular powdered detergents may comprise one or more bleaching agents. Suitable bleaching agents include other photobleaches, preformed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches, for example Vitamin K3;

(2) preformed peracids: suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO2008/007319 (hereby incorporated by reference). Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants: The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents: The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent: The detergent compositions of the present invention will preferably also contain additional components that may tint articles being cleaned, such as fluorescent whitening agent or optical brighteners. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of:

4,4'-bis-(2-diethanolamino-4-anilino-s-triazin-6-ylamino) stilbene-2,2'-disulphonate,
4,4'-bis-(2,4-dianilino-s-triazin-6-ylamino) stilbene-2,2'-disulphonate,
4,4'-bis-(2-anilino-4(N-methyl-N-2-hydroxy-ethylamino)-s-triazin-6-ylamino)stilbene-2,2'-disulphonate,
4,4'-bis-(4-phenyl-2,1,3-triazol-2-yl)stilbene-2,2'-disulphonate,
4,4'-bis-(2-anilino-4(1-methyl-2-hydroxy-ethylamino)-s-triazin-6-ylamino) stilbene-2,2'-disulphonate and,
2-(stilbyl-4"-naptho-1.,2':4,5)-1,2,3-trizole-2"-sulphonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate.

Also preferred are fluorescent whitening agents is the commercially available Parawhite KX, supplied by Paramount Minerals and Chemicals, Mumbai, India.

Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Fabric hueing agents: The detergent compositions of the present invention may also include fabric hueing agents such as dyes or pigments which when formulated in detergent compositions can deposit onto a fabric when said fabric is contacted with a wash liquor comprising said detergent compositions, thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 05/03274, WO 05/03275, WO 05/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers: The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 09/087,523 (hereby incorporated by reference). Furthermore random graft co-polymers are suitable soil release polymers Suitable graft co-polymers are described in more detail in WO 07/138,054, WO 06/108856 and WO 06/113314 (hereby incorporated by reference). Other soil release polymers are substituted polysaccharide structures especially substituted cellulosic structures such as modified cellulose derivitaives such as those described in EP 1867808 or WO 03/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents: The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-amino-functional solvent; and d) from about 5% to about 20%, by weight of the composition, of a performance additive selected from chelants, soil release polymers, enzymes and mixtures thereof; wherein the compact fluid laundry detergent composition comprises at least one of:
(i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (iii) both (i) and (ii). All the ingredients are described in WO 07/130,562 hereby incorporated by reference in its entirety further polymers useful in detergent formulations are described in WO 07/149,806, which is hereby incorporated by reference in its entirety.

In another aspect the detergent is a compact granular (powdered) detergent comprising a) at least about 10%, preferably from 15 to 60% by weight of the composition, of surfactant selected from anionic surfactants, non ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeiolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c) from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

Uses

A lysozyme variant, or a composition thereof, of the present invention may be used in several applications to degrade a material comprising a peptidoglycan or a chitodextrin by treating the material with the polypeptide or composition thereof (see for example Proctor and Cunningham, (1988) *Critical Reviews in Food Science and Nutrition* 26:359-395; Carini et al. (1985) *Microbiol. Alimen. Nutr.* 3:299-320; Hughey and Johnson (1987) *Appl. Environ. Microbiol.* 53:2165-2170; Cunningham et al. (1991) *World's Poultry Science Journal* 47:141-163).

Examples of preferred uses of the lysozyme variants or compositions thereof of the present invention are given below. The dosage of the lysozyme variant and other conditions under which the lysozyme variants is used may be determined on the basis of methods known in the art.

The variant lysozymes of the present invention may be used as antimicrobial agents. One aspect of the present invention is a method for reducing microbial contamination, comprising treating a microbial contaminated surface with a lysozyme variant of the present invention.

To assess whether a lysozyme variant of the present invention is capable of acting as an antimicrobial agent it can be tested in a turbidity assay. In this assay it is tested whether the lysozyme is capable of degrading microbial cells e.g. a dried substrate of *Exiguobacterium undae* cells (isolated from a smelly sock) or *Clostridium perfringens* cells dissolved in buffer or detergent, and thereby reducing the optical density (OD) at for example 540 nm, when compared to a microbial suspension only treated with buffer.

The variant lysozyme is preferably incorporated into and/or used together with detergent compositions as described above.

When washing is performed repeatedly at temperatures below 60° C. there is an increased risk of malodour in the washing machine (laundry as well as dishwashing) and on the textiles washed in the machine. This malodour is likely to be caused by microbial organisms such as bacteria, fungi, algae or other unicellular organisms growing in the washing machine. The present invention provides a method of reducing microbial contamination on a surface, such as a textile garment or hard surface such as metal, plastic or rubber parts in a washing machine, bathroom tiles, floors, table tops, drains, sinks and washbasin, by treating the microbial contaminated surface with a lysozyme variant or lyzysyme variant composition of the present invention. Such a treatment is also expected to reduce the malodour on textiles and hard surfaces containing microbial contamination.

The reduction of microbial contamination can be assessed in several ways, for example by letting a panel assess whether the smell has been decreased, alternatively a sample may be taken from the surface and cultivated to assess whether the microbial count has been reduced as a result of the treatment compared to a treatment without lysozyme.

Furthermore, the invention relates to a process for laundering of fabrics comprising treating fabrics with a washing solution containing a detergent composition and a lysozyme variant or a lysozyme variant composition of the invention. The laundering treatment can for example be carried out in a machine washing process or in a manual washing process. The washing solution can for example be an aqueous washing solution containing the detergent composition and with a pH between 3 and 12, preferably between pH 7 and 12, more preferably between pH 8 and 10.

The fabrics subjected to the methods of the present invention may be conventional washable laundry, for example household laundry. Preferably, the major part of the laundry is garments and fabrics, including knits, wovens, denims, yarns, and towelling, made from cotton, cotton blends or natural or manmade cellulosics (e.g. originating from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell).

The lysozyme variant of the invention may also be used in animal feed. In an embodiment, the present invention provides a method for preparing an animal feed composition comprising adding a lysozyme variant of the present invention to one or more animal feed ingredients. Preferably, the animal feed does not contain antibiotics.

The lysozyme variants of the present invention may for example be used to stabilize the healthy microflora of animals, in particular livestock such as, but not limited to, cattle, dear, goats, pigs, poultry, rabbits and sheep, but also in fish by suppressing growth/intestinal colonization of pathogens such as *Clostridium perfringens, Escherichia coli, Salmonella*, such as *Salmonella typhimurium* and *Salmonella Mbandaka*, and *Camplylobacter* sp. In a preferred embodiment, the lysozyme variant replaces antibiotics in animal diets. Especially variants with increased stability at acidic pH and improved stability towards proteases are suitable for feed applications since they can survive the passage through the digestive tract. In a preferred embodiment a lysozyme variant is applied to chicken and has anti-microbal activity against *Clostridium perfringens*. In a further embodiment a lysozyme variant of the present invention is used as a feed additive, where it may provide a positive effect on the microbial balance of the chicken digestive tract and in this way improve animal performance.

Lysozyme variants may also be used in animal feed as feed enhancing enzymes that improve feed digestibility to increase the efficiency of its utilization according to WO 00/21381 and WO 04/026334.

The lysozyme variants may be used for disinfection and for preventing or removing biofilm on a surface according to U.S. Pat. No. 6,777,223.

The lysozyme variants may also be used to selectively inhibit the uncontrolled growth of *Clostridium tyrobutyricum* during the maturation of cheeses, in particular those made from pressed and cooked curds, e.g. Swiss Cheese, Parmesan, Edam, Gouda, Cheddar, and many others.

The lysozyme variants may also be used in oral care. For example, lysozyme can be used alone or in combination with other enzymes or even antimicrobial peptides in toothpaste or other oral care products. The polypeptides may be introduced into the oral cavity or applied to an article that is to be introduced into the oral cavity. See for example WO 08/124, 764.

The lysozyme variants may also be used in topical treatment of dystrophic and inflammatory lesions of the skin and soft tissues. See for example Palmieri and Boraldi (1977) *Arch. Sci. Med.* (Torino) 134:481-485.

The lysozyme variants may also be used in skin care. For example, the polypeptide is applied to the skin of a patient suffering from a skin infection, such as acne. The lysozyme variants may also be used in a wound dressing, which is applied to wounded skin, for example, to aid in healing of the wound. See for example U.S. Application No. 20080254079.

The lysozyme variants may also be used in lipstick, lip balm, lip gel, or lip gloss. For example, such products can be used for treatment of a localized lip infection, for example, a cold sore. See for example U.S. Application No. 20080254079.

The lysozyme variants may also be used in the treatment of bronchopulmonary diseases.

The present invention is further described by the following examples that should not be construed as limiting the scope of the invention.

EXAMPLES

Materials and Methods

Turbidity Assay

The activity of Lysozyme was determined by measuring the decrease (drop) in absorbance/optical density of a solution of resuspended dried cells of *Exiguobacterium undae* measured in a spectrophotometer at 540 nm.

Preparation of Dried Cells of *Exiguobacterium Undae* (The Substrate)

A culture of *E. undae* (DSM14481) was grown in 100 mL LB medium (Fluka 51208, 25 g/L) in a 500 mL shake-flask at 30° C., 250 rpm overnight. The overnight culture was then centrifuged at 20° C., 5000 g for 10 minutes, and the pellet was washed two times in sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour before the weight of the cells was determined. The dried cells were stored at −20° C. Before use the cells were resuspended in Universal buffer at pH 6 to a concentration of 0.5 mg cells/mL and the optical density (OD) at 540 nm was measured. The cell suspension was then adjusted so the cell concentration equaled an OD540=1.0. The adjusted cell suspension was then stored cold before use. Resuspended cells should be used within 4 hours.

Measurement of Lysozyme Antimicrobial Activity in the Turbidity Assay

The lysozyme sample to be measured was diluted to a concentration of 100-200 mg enzyme protein/L in Universal buffer (see below) at pH 6, and kept on ice until use. In a 96 well microtiterplate (Nunc) 200 μL of the substrate was added to each well, and the plate was incubated at 37° C. for 5 minutes in a PowerWaveX spectrophotometer (Bio-Tek Instruments INC). Following the incubation the absorbance of each well was measured at 540 nm (start value). To start the activity measurement 20 μL of the diluted lysozyme samples was added to the 200 μL substrate in each well and kinetic measurement of absorbance at 540 nm was initiated for minimum 30 minutes up to 24 hours at 37° C. The measured absorbance at 540 nm was monitored for each well and over time a drop in absorbance was seen if the lysozyme had antimicrobial activity. The larger the drop in absorbance was the larger was the lysozyme antimicrobial activity.

Preparation of Universal Buffer Stock

Stock:

| | | |
|---|---|---|
| 100 mM Succinic acid | 118.09 g/mol | 5.90 g |
| 100 mM HEPES | 238.3 g/mol | 11.9 g |
| 100 mM CHES | 207.29 g/mol | 10.4 g |
| 100 mM CAPS | 221.31 g/mol | 11.1 g |
| 150 mM NaCl | 58.44 g/mol | 4.38 g |

Mix in 500 mL water. Adjust pH with HCl or NaOH to pH 6. Dilute buffer 10 times before use.

In order to compare results from the turbidity assay the samples to be compared should preferably be tested in the same experimental run using the same buffer and substrate batch.

Variations in the Lysozyme Antimicrobial Activity in the Turbidity Assay

The assay described above, is the preferred standard microbial activity test for the present invention. However, for lysozyme variants which are generated to achieve an improved property, the assay may be adapted.

To test improved thermal activity the incubation temperature can be increased to the desired temperature, e.g. from 45° C. to 110° C. If the temperature exceeds 50° C., the sample must be incubated in a external heat-source instead of directly in the spectrophotometer measurements are then performed by measuring a start value and an end value.

To test improved activity at low or moderate temperatures the incubation temperature can be changed to the desired temperature, e.g. from 0° C. to 40° C.

To test improved temperature stability the lysozyme sample may be pre-incubated at a desired temperature, e.g. 45° C. to 110° C. for 30 min to 24 hours, and then cooled down to the temperature of the assay described above before measuring the activity.

To test improved pH activity the pH may be increased to for example pH 7.5 to 12 or decreased pH for example from 2 to 5.5.

To test improved pH stability the lysozyme sample may be pre-incubated at a desired pH for 30 min to 24 h, and then returned to the pH of the assay described above before measuring the activity.

To test increased resistance to protease degradation the lysozyme sample may be pre-incubated with pepsin at 0.5 to 2 mg/ml, preferably from 1 to 1.5 mg/ml or with a serine-proteases such as 10 mg/L Savinase at 25-40° C. for 30 min to 24 h prior to conducting the assay described above.

The temperature and pH optimum of a lysozyme may also be assessed using the turbidity assay. For temperature optimum assessment the assay is run in a range of temperatures, for example from 5° C. to 80° C., while the pH is maintained at 6. For pH optimum the pH of the assay is varied over a range, for example pH 2 to 12 while the temperature is maintained at 37° C.

Example 1

Generation of Variants

Using the methods described above following variants of A fumigates lyzozyle (SEQ ID NO: 2) was prepared

| | |
|---|---|
| N19D, | H20W, |
| H20Y, | K22G, |
| K30Y, | Q35R, |
| T45G, | Y47F, |
| D49G, | H55A, |
| Y56W, | L65I, |
| K76S, | F85Y, |
| N89S, | D95G, |
| R98G, | G102P + Y134V, |
| Y108F, | Y111F, |
| H120Q, | V131C, |
| H136N, | S139G, |
| W141Y, | T147G, |
| R153T, | A158S, |
| F161Y, | K164T, |
| A171R, | K178G, |
| D183G, | T186Y + W187Y, |
| S193A, | K195S, |
| Y196G + K197P, | H198F, |
| D203N, | N206A, |
| N206S, | E107A, |
| D105A. | |

Example 2

Stability at Low pH in Gastric Juice

Measurement of Lysozyme Stability to pH 2 and Pepsin Incubation

To measure lysozyme stability under simulated stomach conditions we incubated wt lysozyme as well as selected variants in artificial gastric juice (0.01 M HCl, 0.1 M NaCl, 1 mg/ml pepsin). Lysozyme samples were diluted to a concentration of 50 mg enzyme protein/L in milliQ water. In a 96 well microtiterplate (Nunc) 162 µL of artificial gastric juice was added to each well together with 18 µL lysozyme sample at t=0 min. Samples were incubated for 1 hour at 37° C., 350 rpm in an Eppendorf termomixer. Each lysozyme was tested in triplicate. To stop the stomach incubation at t=60 min 20 µL citric acid $Na_2PO_4$ buffer solution pH 6.8 (Prepared by mixing 22.75 ml 0.1 M citric acid with 77.25 ml 0.2 M $Na_2PO_4$) was added to each well. Microtitre wells without lysozyme were used as negative controls and wells with citric acid $Na_2PO_4$ buffer solution pH 6.8 added at t=0 min before addition of lysozyme was used as positive controls.

To measure residual lysozyme activity 20 µL E. undae suspension was added to each well and OD 540 nm was measured each minute for 1 hour at 37° C. in a Sunrise spectrophotometer (Tecan). OD 540 nm measurements at t=60 min were used for calculations. Lysozyme residual activity in percent was calculated as Lysozyme residual activity=((OD (540 nm) negative control−OD (540 nm) gastric test)/OD (540 nm) positive control)*100%

Results

Lysozyme wt and selected variants were tested for stability towards incubation in artificial gastric juice. Residual activities of the tested variants are shown in table 1. 3 out of 7 variants had improved stability compared to the wt.

TABLE 1

Residual activity of lysozyme variant incubated in artificial gastric juice.

| Variant | Residual activity % |
|---|---|
| Y56W | 98 |
| V131C | 81 |
| F161C | 51 |
| Wildtype | 40 |
| D95G | 38 |
| R98G | 15 |
| D203N | 3 |
| N206A | 0 |

Example 3

Thermostability of Variants

Measurement of Lysozyme Thermostability

Purified samples lysozyme and variants were suspended to a concentration of 10 ppm in 40× diluted buffer originally consisting of 11.8 g succinic acid; 23.8 g HEPES; 20.8 g CHES; 22.2 g CAPS and 8.76 g NaCl pr. L. Buffer pH was adjusted to pH 6 with HCl or NaOH prior to use. Lysozyme thermostability was tested by incubation of purified lysozyme and variants thereof in a Veriti thermal Cycler (Applied Biosystems) for 10 min at 90° C. Simultaneously, control samples were incubated on ice. Immediately after incubation samples were put on ice, substrate added (substrate was prepared as described above). Residual activity was essentially assessed as described above except that activity was measured for 20 minutes.

Results Thermostability

Lysozyme wt and selected variants were tested for thermostability. Residual activities of the tested variants relative to WT are shown in table 2. 10 variants had relative residual activities greater than 5% and may therefore be considered as having enhanced thermostability in comparison to WT.

TABLE 2

Residual activity of lysozyme variants relative to WT after heating

| Variant Mutations | Relative residual activity % |
|---|---|
| N19D | 15 |
| H20Y | 37 |
| K22G | 26 |
| T45G | 21 |
| Y47F | 18 |
| D49G | 14 |
| H55A | 20 |
| R98G | 9 |
| G102P + Y134V | −5 |

TABLE 2-continued

Residual activity of lysozyme variants relative to WT after heating

| Variant Mutations | Relative residual activity % |
|---|---|
| Y111F | −1 |
| H120Q | −6 |
| H136N | 2 |
| S139G | −10 |
| R153T | 4 |
| A158S | 11 |
| K164T | 10 |
| A171R | −11 |
| K178G | −5 |
| S193A | −3 |
| H198F | −9 |
| D203N | −13 |
| N206A | −4 |
| E107A | 3 |

The invention claimed is:

1. An isolated lysozyme variant of a parent lysozyme, comprising an amino acid alteration at one or more positions selected from the group consisting of
19, 20, 22, 30, 32, 35, 45, 47, 49, 55, 56, 76, 89, 98, 102, 108, 110, 111, 112, 113, 119, 120, 121, 131, 134, 135, 147, 153, 158, 161, 164, 171, 178, 183, 185, 186, 187, 193, 195, 196, 198, 203, and 206,
wherein SEQ ID NO: 3 is used for numbering, the lysozyme variant is at least 90% identical to the mature polypeptide of SEQ ID NO: 2 or to the polypeptide of SEQ ID NO: 3, and the lysozyme variant has antimicrobial activity.

2. The lysozyme variant of claim 1, which is at least 95% identical to the mature polypeptide of SEQ ID NO: 2 or to the polypeptide of SEQ ID NO: 3.

3. The lysozyme variant of claim 2, which comprises a substitution at position 18.

4. The lysozyme variant of claim 2, which comprises a substitution at position 19.

5. The lysozyme variant of claim 2, which comprises a substitution at position 20.

6. The lysozyme variant of claim 2, which comprises a substitution at position 22.

7. The lysozyme variant of claim 2, which comprises a substitution at position 45.

8. The lysozyme variant of claim 2, which comprises a substitution at position 49.

9. The lysozyme variant of claim 2, which comprises a substitution at position 55.

10. The lysozyme variant of claim 2, which comprises a substitution at position 56.

11. The lysozyme variant of claim 10, which comprises Y56W.

12. The lysozyme variant of claim 2, which comprises a substitution at position 131.

13. The lysozyme variant of claim 12, which comprises V131C.

14. The lysozyme variant of claim 2, which comprises a substitution at position 161.

15. A detergent composition comprising the lysozyme variant of claim 2 and a surfactant.

16. A feed composition comprising the lysozyme variant of claim 2 and a feed component.

17. A method for reducing microbial contamination, comprising treating a microbial contaminated surface with a lysozyme variant of claim 2.

18. An isolated polynucleotide encoding the lysozyme variant of claim 2.

19. A recombinant host cell comprising an expression vector comprising the polynucleotide of claim 18.

20. A method of producing a lysozyme variant, comprising:
   (a) culturing a host cell of claim 19 under conditions suitable for expression of the variant; and
   (b) recovering the lysozyme variant from the cultivation medium.

21. An isolated lysozyme variant of a parent lysozyme, comprising an amino acid alteration at one or more positions selected from the group consisting of
   85, 128, and 174,
wherein SEQ ID NO: 3 is used for numbering, the lysozyme variant is at least 90% identical to the mature polypeptide of SEQ ID NO: 2 or to the polypeptide of SEQ ID NO: 3, and the lysozyme variant has antimicrobial activity.

22. The lysozyme variant of claim 21, which is at least 95% identical to the mature polypeptide of SEQ ID NO: 2 or to the polypeptide of SEQ ID NO: 3.

23. A detergent composition comprising the lysozyme variant of claim 22 and a surfactant.

24. A feed composition comprising the lysozyme variant of claim 22 and a feed component.

25. A method for reducing microbial contamination, comprising treating a microbial contaminated surface with a lysozyme variant of claim 22.

26. An isolated polynucleotide encoding the lysozyme variant of claim 22.

27. A recombinant host cell comprising an expression vector comprising the polynucleotide of claim 25.

28. A method of producing a lysozyme variant, comprising:
   (a) culturing a host cell of claim 27 under conditions suitable for expression of the variant; and
   (b) recovering the lysozyme variant from the cultivation medium.

* * * * *

UNITED STATES PATENT AND TRADEMARK OFFICE
CERTIFICATE OF CORRECTION

PATENT NO. : 8,865,637 B2  
APPLICATION NO. : 13/521538  
DATED : October 21, 2014  
INVENTOR(S) : Leonardo De Maria Page 1 of 1

It is certified that error appears in the above-identified patent and that said Letters Patent is hereby corrected as shown below:

On the Title page, please amend the row beginning with item (73), delete "Novozymes Als" and insert --Novozymes A/S--.

On the Title page, in the row beginning with item (56), under "FOREIGN PATENT DOCUMENTS":

Delete "WO    20041017988" and insert --WO    2004/017988--

Delete "WO    20041026334" and insert --WO    2004/026334--

Delete "WO    20051080559" and insert --WO    2005/080559--

Delete "WO    20081124764" and insert --WO    2008/124764--

Signed and Sealed this  
Third Day of March, 2015

Michelle K. Lee  
*Deputy Director of the United States Patent and Trademark Office*

SEQUENCE LISTING

<160> NUMBER OF SEQ ID NOS: 13

<210> SEQ ID NO 1
<211> LENGTH: 705
<212> TYPE: DNA
<213> ORGANISM: Aspergillus fumigatus

<400> SEQUENCE: 1

```
atgaagttct ctatcgttgc cattgccact attgccggcc tggcttcggc cctcccagt      60
caacccgaag cccgcgcaac cactgtccag ggcttcgaca tctccaacca ccagaagagc    120
gtcaactttg aagctgccaa gaaggatggc gcgcagttcg tgatgatcaa ggctactgaa    180
ggcacgacct acaaagacac cgtcttcaac tcgcactaca ctggcgccac caaggccggc    240
cttctccgtg gcggatacca ttttgccgc cctgacaagt ccacgggcag cacgcaagcc     300
aaattcttcc tgaagaacgg cggcggatgg agcgacgata accgcacact gcccgggatg    360
ctggatatcg agtacaaccc ctacgagcg acatgttatg gctgagcca ttcccagatg      420
gtcgcttgga tccacgattt tgtcaacgag taccatcatg cgacgagtcg gtggcccatg    480
atctacacca ctgcagactg gtggaatcgc tgcacgggca atgctaaggg cttcggcgac    540
aagtgtcccc tggtgctggc ggcgtatagc agctctcctc ccaagacgat tccaggtgac    600
tggaagacat ggacaatctg gcagaattcg gacaagtata gcatggagg agactcggac     660
aaattcaatg gcccgatgac ccagttgagg aagttagcca gtggt                    705
```

<210> SEQ ID NO 2
<211> LENGTH: 235
<212> TYPE: PRT
<213> ORGANISM: Aspergillus fumigatus

<400> SEQUENCE: 2

```
Met Lys Phe Ser Ile Val Ala Ile Ala Thr Ile Ala Gly Leu Ala Ser
 1               5                  10                  15

Ala Leu Pro Ser Gln Pro Glu Ala Arg Ala Thr Thr Val Gln Gly Phe
                20                  25                  30

Asp Ile Ser Asn His Gln Lys Ser Val Asn Phe Glu Ala Ala Lys Lys
            35                  40                  45

Asp Gly Ala Gln Phe Val Met Ile Lys Ala Thr Glu Gly Thr Thr Tyr
        50                  55                  60

Lys Asp Thr Val Phe Asn Ser His Tyr Thr Gly Ala Thr Lys Ala Gly
 65                  70                  75                  80

Leu Leu Arg Gly Gly Tyr His Phe Ala Arg Pro Asp Lys Ser Thr Gly
                85                  90                  95

Ser Thr Gln Ala Lys Phe Phe Leu Lys Asn Gly Gly Gly Trp Ser Asp
```

```
                    100                 105                 110
Asp Asn Arg Thr Leu Pro Gly Met Leu Asp Ile Glu Tyr Asn Pro Tyr
                115                 120                 125
Gly Ala Thr Cys Tyr Gly Leu Ser His Ser Gln Met Val Ala Trp Ile
                130                 135                 140
His Asp Phe Val Asn Glu Tyr His His Ala Thr Ser Arg Trp Pro Met
145                 150                 155                 160
Ile Tyr Thr Thr Ala Asp Trp Trp Asn Arg Cys Thr Gly Asn Ala Lys
                165                 170                 175
Gly Phe Gly Asp Lys Cys Pro Leu Val Leu Ala Ala Tyr Ser Ser Ser
                180                 185                 190
Pro Pro Lys Thr Ile Pro Gly Asp Trp Lys Thr Trp Thr Ile Trp Gln
                195                 200                 205
Asn Ser Asp Lys Tyr Lys His Gly Gly Asp Ser Asp Lys Phe Asn Gly
                210                 215                 220
Pro Met Thr Gln Leu Arg Lys Leu Ala Ser Gly
225                 230                 235

<210> SEQ ID NO 3
<211> LENGTH: 218
<212> TYPE: PRT
<213> ORGANISM: Aspergillus fumigatus

<400> SEQUENCE: 3

Leu Pro Ser Gln Pro Glu Ala Arg Ala Thr Thr Val Gln Gly Phe Asp
1               5                   10                  15
Ile Ser Asn His Gln Lys Ser Val Asn Phe Glu Ala Ala Lys Lys Asp
                20                  25                  30
Gly Ala Gln Phe Val Met Ile Lys Ala Thr Glu Gly Thr Thr Tyr Lys
                35                  40                  45
Asp Thr Val Phe Asn Ser His Tyr Thr Gly Ala Thr Lys Ala Gly Leu
                50                  55                  60
Leu Arg Gly Gly Tyr His Phe Ala Arg Pro Asp Lys Ser Thr Gly Ser
65                  70                  75                  80
Thr Gln Ala Lys Phe Phe Leu Lys Asn Gly Gly Gly Trp Ser Asp Asp
                85                  90                  95
Asn Arg Thr Leu Pro Gly Met Leu Asp Ile Glu Tyr Asn Pro Tyr Gly
                100                 105                 110
Ala Thr Cys Tyr Gly Leu Ser His Ser Gln Met Val Ala Trp Ile His
                115                 120                 125
Asp Phe Val Asn Glu Tyr His His Ala Thr Ser Arg Trp Pro Met Ile
                130                 135                 140
Tyr Thr Thr Ala Asp Trp Trp Asn Arg Cys Thr Gly Asn Ala Lys Gly
145                 150                 155                 160
Phe Gly Asp Lys Cys Pro Leu Val Leu Ala Ala Tyr Ser Ser Ser Pro
                165                 170                 175
Pro Lys Thr Ile Pro Gly Asp Trp Lys Thr Trp Thr Ile Trp Gln Asn
                180                 185                 190
Ser Asp Lys Tyr Lys His Gly Gly Asp Ser Asp Lys Phe Asn Gly Pro
                195                 200                 205
Met Thr Gln Leu Arg Lys Leu Ala Ser Gly
                210                 215

<210> SEQ ID NO 4
<211> LENGTH: 309
```

<212> TYPE: PRT
<213> ORGANISM: Aspergillus fumigatus

<400> SEQUENCE: 4

```
Met Lys Phe Ser Ile Val Ala Ile Ala Thr Ile Ala Gly Leu Ala Ser
1               5                   10                  15

Ala Leu Pro Ser Gln Pro Glu Ala Arg Ala Thr Thr Val Gln Gly Phe
            20                  25                  30

Asp Ile Ser Asn His Gln Lys Ser Val Asn Phe Glu Ala Ala Lys Lys
        35                  40                  45

Asp Gly Ala Gln Phe Val Met Ile Lys Ala Thr Glu Gly Thr Thr Tyr
    50                  55                  60

Lys Asp Thr Val Phe Asn Ser His Tyr Thr Gly Ala Thr Lys Ala Gly
65                  70                  75                  80

Leu Leu Arg Gly Gly Tyr His Phe Ala Arg Pro Asp Lys Ser Thr Gly
                85                  90                  95

Ser Thr Gln Ala Lys Phe Phe Leu Lys Asn Gly Gly Gly Trp Ser Asp
            100                 105                 110

Asp Asn Arg Thr Leu Pro Gly Met Leu Asp Ile Glu Tyr Asn Pro Tyr
        115                 120                 125

Gly Ala Thr Cys Tyr Gly Leu Ser His Ser Gln Met Val Ala Trp Ile
    130                 135                 140

His Asp Phe Val Asn Glu Tyr His His Ala Thr Ser Arg Trp Pro Met
145                 150                 155                 160

Ile Tyr Thr Thr Ala Asp Trp Trp Asn Arg Cys Thr Gly Asn Ala Lys
                165                 170                 175

Gly Phe Gly Asp Lys Cys Pro Leu Val Leu Ala Ala Tyr Ser Ser Ser
            180                 185                 190

Pro Pro Lys Thr Ile Pro Gly Asp Trp Lys Lys Trp Thr Ile Trp Gln
        195                 200                 205

Asn Ser Asp Lys Tyr Lys His Gly Gly Asp Ser Asp Lys Phe Asn Gly
    210                 215                 220

Pro Met Thr Gln Leu Arg Lys Met Pro Ser Lys Pro Leu Ala Asp His
225                 230                 235                 240

Pro Ile Gln Pro Lys Lys Val His Gly Val Thr Arg Asp Asp Ala Pro
                245                 250                 255

Ile Asp Asp Tyr Glu Asn Ala Ile Arg Ser Lys Gln Gln Glu Glu Glu
            260                 265                 270

Pro Ser Asp Arg Gly Glu Asp Ala Pro Ser His Phe Gly Thr Ser Thr
        275                 280                 285

Arg His Lys Gly Val Arg Thr Arg Ser His Gly Ser Glu Asn Arg Ser
    290                 295                 300

Thr Thr Gly Arg Val
305
```

<210> SEQ ID NO 5
<211> LENGTH: 235
<212> TYPE: PRT
<213> ORGANISM: Aspergillus fischerianus

<400> SEQUENCE: 5

```
Met Lys Phe Ser Ile Ala Ala Ile Ala Thr Ile Ala Gly Leu Ala Ser
1               5                   10                  15

Ala Leu Pro Ser Gln Pro Glu Ala Arg Ala Thr Thr Ile Gln Gly Phe
            20                  25                  30
```

```
Asp Ile Ser Asn His Gln Lys Ser Val Asn Phe Glu Ala Lys Lys
             35                  40                  45

Asp Gly Ala Gln Phe Val Met Ile Lys Thr Thr Glu Gly Thr Thr Tyr
 50                  55                  60

Lys Asp Thr Val Phe Asn Ser His Tyr Thr Gly Ala Thr Lys Ala Gly
 65                  70                  75                  80

Leu Leu Arg Gly Gly Tyr His Phe Ala Arg Pro Asp Lys Ser Thr Gly
                 85                  90                  95

Ser Thr Gln Ala Lys Phe Phe Leu Lys Asn Gly Gly Trp Ser Asn
                100                 105                 110

Asp Asn Arg Thr Leu Pro Gly Met Leu Asp Ile Glu Tyr Asn Pro Tyr
            115                 120                 125

Gly Ala Thr Cys Tyr Gly Leu Ser His Ser Gln Met Val Ala Trp Ile
130                 135                 140

His Asp Phe Val Asp Glu Tyr His His Ala Thr Ser Arg Trp Pro Met
145                 150                 155                 160

Ile Tyr Thr Thr Ala Asp Trp Trp Asn Arg Cys Thr Gly Asn Ala Lys
                165                 170                 175

Gly Phe Gly Asp Lys Cys Pro Leu Val Leu Ala Ala Tyr Ser Ser Ser
            180                 185                 190

Pro Pro Lys Thr Ile Pro Gly Asp Trp Lys Thr Trp Thr Ile Trp Gln
        195                 200                 205

Asn Ser Asp Lys Tyr Glu His Gly Gly Asp Ser Asp Lys Phe Asn Gly
    210                 215                 220

Pro Met Thr Gln Leu Arg Lys Leu Ala Ser Gly
225                 230                 235

<210> SEQ ID NO 6
<211> LENGTH: 235
<212> TYPE: PRT
<213> ORGANISM: Aspergillus clavatus

<400> SEQUENCE: 6

Met Lys Leu Ser Ile Ala Val Thr Ala Thr Ile Ala Ala Leu Ala Ser
 1               5                  10                  15

Ala Leu Pro Ser Gln Ser Glu Ala His Ala Ser Thr Val Gln Gly Phe
                 20                  25                  30

Asp Ile Ser Asn His Gln Lys Thr Val Asp Phe Glu Ala Ala Lys Lys
             35                  40                  45

Asp Gly Ala Gln Phe Val Met Ile Lys Ala Thr Glu Gly Thr Thr Tyr
 50                  55                  60

Lys Asp Thr Thr Phe Asn Ser His Tyr Thr Gly Ala Thr Lys Ala Gly
 65                  70                  75                  80

Leu Ile Arg Gly Gly Tyr His Phe Ala Arg Pro Asp Lys Ser Ser Gly
                 85                  90                  95

Ser Thr Gln Ala Thr Tyr Phe Val Lys Asn Gly Gly Trp Ser Asp
                100                 105                 110

Asp Lys Met Thr Leu Pro Gly Met Leu Asp Ile Glu Tyr Asn Pro Tyr
            115                 120                 125

Gly Ala Thr Cys Tyr Gly Leu Ser His Ser Ala Met Val Ser Trp Ile
130                 135                 140

Lys Glu Phe Val Asp Glu Tyr His Ser Ala Thr Lys Arg Tyr Pro Met
145                 150                 155                 160

Ile Tyr Thr Thr Ala Asp Trp Trp Asn Arg Cys Thr Gly Asn Ala Lys
                165                 170                 175
```

```
Gly Phe Gly Asp Lys Cys Pro Leu Val Leu Ala Ala Tyr Ser Ser Thr
            180                 185                 190

Ala Pro Lys Thr Ile Pro Gly Asp Trp Lys Thr Trp Thr Ile Trp Gln
            195                 200                 205

Asp Ser Asp Lys Tyr Lys His Gly Gly Asp Ser Asp Lys Phe Asn Gly
210                 215                 220

Pro Met Thr Gln Leu Lys Lys Leu Ala Ser Gly
225                 230                 235

<210> SEQ ID NO 7
<211> LENGTH: 230
<212> TYPE: PRT
<213> ORGANISM: Aspergillus oryzae

<400> SEQUENCE: 7

Met Lys Leu Ala Asn Leu Ala Leu Ser Ala Thr Ala Gly Leu Ser Leu
1               5                   10                  15

Lys Ala Thr Ser Glu Thr Val Gln Gly Phe Asp Ile Ser Asn His Gln
            20                  25                  30

Ala Thr Val Asp Phe Lys Ala Ala Tyr Asn Asp Gly Ala Arg Phe Val
        35                  40                  45

Met Ile Lys Ala Thr Glu Gly Thr Thr Phe Thr Asp Lys Val Phe Ser
    50                  55                  60

Ser His Tyr Gln Gly Ala Thr Asp Ala Gly Leu Ile Arg Gly Gly Tyr
65                  70                  75                  80

His Phe Ala Leu Pro Asp Ser Ser Gly Ala Glu Gln Ala Glu Phe
                85                  90                  95

Phe Leu Lys Asn Gly Gly Gly Trp Ser Lys Asp Gly Ile Thr Leu Pro
            100                 105                 110

Gly Met Leu Asp Ile Glu Tyr Asn Pro Tyr Gly Ala Thr Cys Tyr Asp
        115                 120                 125

Lys Ser Ala Glu Asp Met Val Ala Trp Ile Lys Asp Phe Val Asp Thr
    130                 135                 140

Tyr Gln Lys Ala Thr Gly Val Tyr Pro Leu Ile Tyr Ser Thr Ala Asp
145                 150                 155                 160

Trp Trp Lys Thr Cys Thr Gly Asn Ala Gly Gly Phe Gly Ser Thr Cys
                165                 170                 175

Pro Leu Val Leu Ala Ala Tyr Ser Asp Ser Ala Pro Ser Thr Ile Pro
            180                 185                 190

Gly Asp Trp Ala Thr Tyr Thr Ile Trp Gln Asn Ser Asp Ser Tyr Lys
        195                 200                 205

His Gly Gly Asp Ser Asp Ile Phe Asn Gly Gly Tyr Glu Gln Leu Gln
    210                 215                 220

Lys Ile Ala Lys Ala Glu
225                 230

<210> SEQ ID NO 8
<211> LENGTH: 233
<212> TYPE: PRT
<213> ORGANISM: Aspergillus terreus

<400> SEQUENCE: 8

Met Lys Leu Asn Asn Leu Ala Leu Ser Val Ala Gly Ala Ala Leu Thr
1               5                   10                  15

Leu Ala Leu Glu Ala His Ala Asp Thr Val Gln Gly Phe Asp Ile Ser
            20                  25                  30
```

Asn His Gln Gly Ser Val Asp Phe Ala Ala Ala Tyr Asn Ala Gly Ala
            35                   40                  45

Arg Phe Val Met Ile Lys Ser Ser Glu Gly Thr Ser Tyr Ser Asp Pro
        50                  55                  60

Ser Phe Ser Ser His Tyr Thr Gly Ala Thr Asp Ala Gly Phe Ile Arg
65                  70                  75                  80

Gly Gly Tyr His Phe Ala Leu Pro Asp Ala Ser Ser Ala Ala Asp Gln
                85                  90                  95

Val Ser Tyr Phe Ile Ser His Gly Gly Gly Trp Ser Lys Asp Gly Ile
            100                 105                 110

Thr Leu Pro Gly Met Leu Asp Ile Glu Tyr Asn Pro Tyr Gly Asp Thr
        115                 120                 125

Cys Tyr Gly Leu Ser Ala Ser Asp Met Val Ala Trp Ile Gln Glu Phe
130                 135                 140

Val Asp Glu Tyr His Ser Ala Thr Gly Val Tyr Pro Met Leu Tyr Thr
145                 150                 155                 160

Thr Ala Asp Trp Trp Ser Thr Cys Thr Gly Asn Ala Ser Gly Phe Gly
                165                 170                 175

Asp Lys Cys Pro Leu Val Leu Ala Ala Tyr Ser Ser Ser Ala Pro Ser
            180                 185                 190

Thr Ile Pro Gly Asp Trp Ala Thr Tyr Thr Met Trp Gln Asn Ser Asp
        195                 200                 205

Ser Tyr Glu Tyr Gly Gly Asp Ser Asp Ile Phe Asn Gly Pro Phe Glu
210                 215                 220

Ser Leu Gln Lys Ile Ala Asn Ala Ala
225                 230

<210> SEQ ID NO 9
<211> LENGTH: 227
<212> TYPE: PRT
<213> ORGANISM: Aspergillus fischerianus

<400> SEQUENCE: 9

Met Met Leu Asp Leu Lys Gln Val Ala Ala Val Leu Leu Ala Ser Ala
1               5                   10                  15

Ser Leu Ala Gln Ala Thr Val Gln Gly Phe Asp Ile Ser His Tyr Gln
            20                  25                  30

Ala Asn Val Asn Phe Ala Ala Ala Tyr Asn Ser Gly Ala Arg Phe Val
        35                  40                  45

Met Ile Lys Ala Thr Glu Ser Thr Thr Tyr Thr Asp Pro Ala Phe Ser
    50                  55                  60

Ser His Tyr Thr Gly Ala Thr Asn Ala Gly Phe Ile Arg Gly Gly Tyr
65                  70                  75                  80

His Phe Ala Ile Pro Asn Asp Ser Ser Gly Ala Ala Gln Ala Lys Tyr
                85                  90                  95

Phe Leu Ala His Gly Gly Gly Trp Ser Asn Asp Gly Ile Thr Leu Pro
            100                 105                 110

Gly Met Leu Asp Ile Glu Tyr Asn Pro Tyr Gly Ala Thr Cys Tyr Gly
        115                 120                 125

Leu Ser Ala Ser Gln Met Val Ser Trp Ile Ser Asp Phe Val Asn Thr
130                 135                 140

Tyr Lys Ser Ser Thr Gly Arg Tyr Pro Met Ile Tyr Thr Thr Ala Asp
145                 150                 155                 160

Trp Trp Asn Thr Cys Thr Gly Asn Ser Lys Ser Phe Thr Glu Cys Pro

```
                    165                 170                 175
Leu Val Leu Ala Arg Tyr Ser Ser Val Gly Thr Ile Pro Gly Gly
            180                 185                 190

Trp Pro Tyr Gln Ser Phe Trp Gln Asn Ser Asp Ser Tyr Thr Tyr Gly
        195                 200                 205

Gly Asp Ser Asp Ile Trp Asn Gly Ser Leu Asn Asn Leu Lys Thr Phe
    210                 215                 220

Ala Lys Gly
225

<210> SEQ ID NO 10
<211> LENGTH: 228
<212> TYPE: PRT
<213> ORGANISM: Aspergillus fumigatus

<400> SEQUENCE: 10

Met Met Leu Leu Asp Leu Lys Gln Val Ala Ala Val Leu Leu Ala Ser
1               5                   10                  15

Ala Ser Leu Ala Gln Ala Ala Val Gln Gly Phe Asp Ile Ser His Tyr
            20                  25                  30

Gln Ser Asn Val Asn Phe Ala Ala Ala Tyr Asn Ser Gly Ala Arg Phe
        35                  40                  45

Val Met Ile Lys Ala Thr Glu Ser Thr Thr Tyr Thr Asp Pro Ser Phe
    50                  55                  60

Ser Ser His Tyr Thr Gly Ala Thr Asn Ala Gly Phe Ile Arg Gly Gly
65                  70                  75                  80

Tyr His Phe Ala Ile Pro Asn Ala Ser Ser Gly Ala Ala Gln Ala Lys
                85                  90                  95

Tyr Phe Leu Ala His Gly Gly Gly Trp Ser Asn Asp Gly Ile Thr Leu
            100                 105                 110

Pro Gly Met Leu Asp Ile Glu Tyr Asn Pro Tyr Gly Ala Thr Cys Tyr
        115                 120                 125

Gly Leu Ser Ala Ser Gln Met Val Ser Trp Ile Ser Asp Phe Val Asn
    130                 135                 140

Thr Tyr Lys Ser Ser Thr Gly Arg Tyr Pro Met Ile Tyr Thr Thr Ala
145                 150                 155                 160

Asp Trp Trp Asn Thr Cys Thr Gly Asn Ser Lys Ser Phe Thr Asp Cys
                165                 170                 175

Pro Leu Val Leu Ala Arg Tyr Ser Ser Val Gly Thr Ile Pro Gly
            180                 185                 190

Gly Trp Pro Tyr Gln Ser Phe Trp Gln Asn Ser Asp Ser Tyr Thr Tyr
        195                 200                 205

Gly Gly Asp Ser Glu Ile Trp Asn Gly Ser Leu Asp Asn Leu Lys Lys
    210                 215                 220

Phe Ala Lys Gly
225

<210> SEQ ID NO 11
<211> LENGTH: 241
<212> TYPE: PRT
<213> ORGANISM: Aspergillus clavatus

<400> SEQUENCE: 11

Met Ser Gln Asn His Pro Gln Thr Ala Lys Phe Lys Met Met Phe Asn
1               5                   10                  15

Leu Lys Gln Thr Ala Ala Val Leu Leu Ala Ser Ala Ser Met Ala Gln
```

```
                    20                  25                  30
Ala Ala Val Gln Gly Phe Asp Ile Ser Asn Tyr Gln Ser Ser Val Asn
                35                  40                  45

Phe Ala Ser Ala Tyr Ser Ser Gly Ala Arg Phe Val Met Ile Lys Ala
     50                  55                  60

Thr Glu Gly Thr Thr Tyr Thr Asp Pro Thr Phe Ser Ser His Tyr Ile
 65                  70                  75                  80

Gly Ala Thr Asn Ala Gly Leu Ile Arg Gly Gly Tyr His Phe Ala Ile
                 85                  90                  95

Pro Ser Ser Ser Gly Ala Thr Gln Ala Lys Tyr Phe Ile Ser His
                100                 105                 110

Gly Gly Gly Trp Ser Ala Asp Gly Ile Thr Leu Pro Gly Met Leu Asp
            115                 120                 125

Ile Glu Tyr Asn Pro Tyr Gly Ala Thr Cys Tyr Gly Leu Ser Ala Ser
        130                 135                 140

Gln Met Val Ala Trp Ile Lys Asp Phe Ala Asn Thr Tyr Lys Ala Ser
145                 150                 155                 160

Val Gly Arg Tyr Pro Met Ile Tyr Thr Thr Asn Asp Trp Trp Asn Thr
                165                 170                 175

Cys Thr Gly Asn Ser Gln Ala Phe Thr Asp Cys Pro Leu Val Leu Ala
                180                 185                 190

Arg Tyr Ser Ser Ala Gly Thr Ile Pro Gly Gly Trp Pro Tyr Gln
            195                 200                 205

Ser Phe Trp Gln Asn Ser Asp Ser Tyr Thr Tyr Gly Gly Asp Ser Asp
        210                 215                 220

Ile Trp Asn Gly Ser Leu Asp Asn Leu Lys Lys Phe Ala Ala Thr Ala
225                 230                 235                 240

Ala

<210> SEQ ID NO 12
<211> LENGTH: 222
<212> TYPE: PRT
<213> ORGANISM: Aspergillus terreus

<400> SEQUENCE: 12

Met Lys Thr Ile Ile Ser Phe Leu Ala Ala Gly Val Ala His Ala
 1               5                  10                  15

Ala Val Gln Gly Phe Asp Ile Ser His Tyr Gln Ser Ser Val Asn Tyr
                 20                  25                  30

Ala Gly Ala Tyr Asn Ser Gly Ala Arg Phe Val Met Ile Lys Ala Thr
             35                  40                  45

Glu Gly Thr Thr Tyr Thr Asp Pro Ser Phe Ser Thr His Tyr Thr Gly
     50                  55                  60

Ala Thr Asn Ala Gly Leu Ile Arg Gly Gly Tyr His Phe Ala Arg Pro
 65                  70                  75                  80

Asp Thr Ser Ser Gly Ala Val Gln Ala Asn Tyr Phe Leu Lys His Gly
                 85                  90                  95

Gly Gly Trp Thr Ser Asp Gly Ile Thr Leu Pro Gly Met Leu Asp Ile
            100                 105                 110

Glu Tyr Asn Pro Tyr Gly Ala Thr Cys Tyr Gly Leu Ser Ala Ser Ser
        115                 120                 125

Met Val Ser Trp Ile Ser Asp Phe Val Glu Thr Tyr Lys Ser Ala Val
    130                 135                 140

Gly Arg Tyr Pro Met Ile Tyr Thr Thr Ala Asn Trp Trp Ser Thr Cys
```

```
145                 150                 155                 160
Thr Gly Asn Ser Ala Ala Phe Thr Asp Cys Pro Leu Val Leu Ala Arg
                165                 170                 175

Tyr Ser Ser Val Gly Thr Ile Pro Gly Gly Trp Pro Tyr Gln Ser
            180                 185                 190

Ile Trp Gln Asn Ser Asp Ser Tyr Ala Tyr Gly Gly Asp Ser Asp Ile
                195                 200                 205

Trp Asn Gly Asp Glu Ala Gly Leu Ser Arg Phe Ala Lys Gly
    210                 215                 220

<210> SEQ ID NO 13
<211> LENGTH: 227
<212> TYPE: PRT
<213> ORGANISM: Penicillium marneffei

<400> SEQUENCE: 13

Met Asn Met Leu Val Ser Thr Leu Ala Val Ser Ala Ser Leu Phe Gly
1               5                   10                  15

Leu Ala Lys Ala Thr Val Gln Gly Phe Asp Ile Ser Ser Tyr Gln Pro
                20                  25                  30

Asn Val Asn Phe Asn Ala Ala Tyr Ser Ala Gly Ala Arg Phe Val Ile
            35                  40                  45

Ile Lys Ala Thr Glu Gly Thr Thr Tyr Ile Asp Ser Thr Phe Ser Asn
50                  55                  60

His Tyr Ile Gly Ala Thr Asn Ala Gly Phe Ile Arg Gly Gly Tyr His
65                  70                  75                  80

Phe Ala His Pro Ser Val Ser Ser Gly Ala Thr Gln Ala Lys Tyr Phe
                85                  90                  95

Ile Ala His Gly Gly Gly Trp Ser Gly Asp Gly Ile Thr Leu Pro Gly
            100                 105                 110

Met Leu Asp Ile Glu Tyr Asn Pro Asn Gly Ala Thr Cys Tyr Gly Leu
            115                 120                 125

Ser Ala Ser Gln Met Val Ser Trp Ile His Asp Phe Val Asn Thr Tyr
    130                 135                 140

Tyr Ala Ser Glu Gly Val Tyr Pro Met Ile Tyr Thr Thr Asn Asp Trp
145                 150                 155                 160

Trp Thr Thr Cys Thr Gly Asp Ser Thr Ala Phe Ser Thr Thr Cys Pro
                165                 170                 175

Leu Val Leu Ala Arg Tyr Ala Ser Ser Pro Gly Thr Ile Pro Gly Gly
            180                 185                 190

Trp Gly Tyr Gln Thr Ile Trp Gln Asn Thr Asp Ser Tyr Ala Tyr Gly
            195                 200                 205

Gly Asp Ser Asp Val Phe Asn Gly Ala Leu Ser Gln Leu Lys Ala Ile
    210                 215                 220

Ala Leu Gly
225
```